US012414686B2

(12) United States Patent
Ayvali et al.

(10) Patent No.: US 12,414,686 B2
(45) Date of Patent: Sep. 16, 2025

(54) ENDOSCOPIC ANATOMICAL FEATURE TRACKING

(71) Applicant: Auris Health, Inc., Santa Clara, CA (US)

(72) Inventors: Elif Ayvali, Redwood City, CA (US); Menglong Ye, Mountain View, CA (US); Bulat Ibragimov, Copenhagen (DK); David Burdick Berman, Millbrae, CA (US)

(73) Assignee: Auris Health, Inc., Santa Clara, CA (US)

( * ) Notice: Subject to any disclaimer, the term of this patent is extended or adjusted under 35 U.S.C. 154(b) by 69 days.

(21) Appl. No.: 18/221,333

(22) Filed: Jul. 12, 2023

(65) Prior Publication Data
US 2023/0363635 A1 Nov. 16, 2023

Related U.S. Application Data

(62) Division of application No. 17/208,874, filed on Mar. 22, 2021, now Pat. No. 11,737,663.
(Continued)

(51) Int. Cl.
*A61B 34/30* (2016.01)
*A61B 1/00* (2006.01)
(Continued)

(52) U.S. Cl.
CPC .......... *A61B 1/307* (2013.01); *A61B 1/00045* (2013.01); *A61B 1/045* (2013.01);
(Continued)

(58) Field of Classification Search
CPC ......... A61B 34/30; A61B 34/25; A61B 90/00; A61B 90/37; A61B 19/203; A61B 19/5244; A61B 1/00; A61B 1/045
See application file for complete search history.

(56) References Cited

U.S. PATENT DOCUMENTS 631,949 A 8/1899 Carlson
639,109 A 12/1899 Staeckig et al.
(Continued)

FOREIGN PATENT DOCUMENTS

CN 1364275 A 8/2002
CN 1511249 A 7/2004
(Continued)

OTHER PUBLICATIONS

EP Search Report for Appl. No. 21782289.9, dated Mar. 8, 2024, 9 pages.
(Continued)

*Primary Examiner* — Vi X Nguyen
(74) *Attorney, Agent, or Firm* — Paradice & Li LLP

(57) ABSTRACT

A method of localizing a target anatomy involves advancing a ureteroscope to a target calyx of a kidney of a patient through at least a portion of a urinary tract of the patient, determining a positional offset between one or more position sensors associated with the ureteroscope and a target papilla of the kidney that is at least partially exposed within the target calyx, and determining a percutaneous access target based at least in part on one or more of a present position of the one or more position sensors or the positional offset.

18 Claims, 20 Drawing Sheets

Related U.S. Application Data

(60) Provisional application No. 63/001,870, filed on Mar. 30, 2020.

(51) Int. Cl.
  *A61B 1/045* (2006.01)
  *A61B 1/307* (2006.01)
  *A61B 90/00* (2016.01)
  *A61B 34/00* (2016.01)
  *A61B 34/20* (2016.01)

(52) U.S. Cl.
  CPC ...... *A61B 90/37* (2016.02); *A61B 2034/2051* (2016.02); *A61B 34/25* (2016.02)

(56) References Cited

U.S. PATENT DOCUMENTS

| | | |
|---|---|---|
| 646,291 A | 3/1900 | Krueger |
| 4,644,237 A | 2/1987 | Frushour et al. |
| 4,745,908 A | 5/1988 | Wardle |
| 4,748,969 A | 6/1988 | Wardle |
| 5,194,791 A | 3/1993 | Cull |
| 5,199,417 A | 4/1993 | Muller et al. |
| 5,251,611 A | 10/1993 | Zehel et al. |
| 5,273,025 A | 12/1993 | Sakiyama et al. |
| 5,280,781 A | 1/1994 | Oku |
| 5,408,263 A | 4/1995 | Kikuchi et al. |
| 5,526,812 A | 6/1996 | Dumoulin et al. |
| 5,550,953 A | 8/1996 | Seraji |
| 5,669,876 A | 9/1997 | Schechter et al. |
| 5,672,877 A | 9/1997 | Liebig et al. |
| 5,769,086 A | 6/1998 | Ritchart et al. |
| 5,831,614 A | 11/1998 | Tognazzini et al. |
| 5,876,325 A | 3/1999 | Mizuno et al. |
| 5,899,851 A | 5/1999 | Koninckx |
| 5,935,075 A | 8/1999 | Casscells et al. |
| 6,004,016 A | 12/1999 | Spector |
| 6,038,467 A | 3/2000 | Bliek et al. |
| 6,047,080 A | 4/2000 | Chen et al. |
| 6,059,718 A | 5/2000 | Taniguchi et al. |
| 6,063,095 A | 5/2000 | Wang et al. |
| 6,167,292 A | 12/2000 | Badano et al. |
| 6,198,974 B1 | 3/2001 | Webster, Jr. |
| 6,203,493 B1 | 3/2001 | Ben-Haim |
| 6,246,200 B1 | 6/2001 | Blumenkranz et al. |
| 6,246,784 B1 | 6/2001 | Summers et al. |
| 6,246,898 B1 | 6/2001 | Vesely et al. |
| 6,332,089 B1 | 12/2001 | Acker et al. |
| 6,425,865 B1 | 7/2002 | Salcudean et al. |
| 6,459,926 B1 | 10/2002 | Nowlin et al. |
| 6,466,198 B1 | 10/2002 | Feinstein |
| 6,490,467 B1 | 12/2002 | Bucholz et al. |
| 6,553,251 B1 | 4/2003 | Lähdesmäki |
| 6,665,554 B1 | 12/2003 | Charles et al. |
| 6,690,963 B2 | 2/2004 | Ben-Haim et al. |
| 6,690,964 B2 | 2/2004 | Bieger et al. |
| 6,755,797 B1 | 6/2004 | Stouffer |
| 6,812,842 B2 | 11/2004 | Dimmer |
| 6,837,846 B2 | 1/2005 | Jaffe et al. |
| 6,899,672 B2 | 5/2005 | Chin et al. |
| 6,926,709 B2 | 8/2005 | Bieger et al. |
| 7,130,700 B2 | 10/2006 | Gardeski et al. |
| 7,131,117 B2 | 10/2006 | Mills et al. |
| 7,180,976 B2 | 2/2007 | Wink et al. |
| 7,197,354 B2 | 3/2007 | Sobe |
| 7,206,627 B2 | 4/2007 | Abovitz et al. |
| 7,233,820 B2 | 6/2007 | Gilboa |
| 7,386,339 B2 | 6/2008 | Strommer et al. |
| 7,607,440 B2 | 10/2009 | Coste-Maniere et al. |
| 7,756,563 B2 | 7/2010 | Higgins et al. |
| 7,763,015 B2 | 7/2010 | Cooper et al. |
| 7,772,541 B2 | 8/2010 | Froggatt et al. |
| 7,850,642 B2 | 12/2010 | Moll et al. |
| 7,901,348 B2 | 3/2011 | Soper et al. |
| 7,963,288 B2 | 6/2011 | Rosenberg et al. |
| 8,021,325 B2 | 9/2011 | Zinger et al. |
| 8,021,326 B2 | 9/2011 | Moll et al. |
| 8,155,403 B2 | 4/2012 | Tschirren et al. |
| 8,190,238 B2 | 5/2012 | Moll et al. |
| 8,298,135 B2 | 10/2012 | Ito et al. |
| 8,317,746 B2 | 11/2012 | Sewell et al. |
| 8,335,557 B2 | 12/2012 | Maschke |
| 8,348,931 B2 | 1/2013 | Cooper et al. |
| 8,376,934 B2 | 2/2013 | Takahashi et al. |
| 8,394,054 B2 | 3/2013 | Wallace et al. |
| 8,396,595 B2 | 3/2013 | Dariush |
| 8,442,618 B2 | 5/2013 | Strommer et al. |
| 8,460,236 B2 | 6/2013 | Roelle et al. |
| 8,469,945 B2 | 6/2013 | Schena |
| 8,498,691 B2 | 7/2013 | Moll et al. |
| 8,506,555 B2 | 8/2013 | Morales |
| 8,554,368 B2 | 10/2013 | Fielding et al. |
| 8,652,030 B2 | 2/2014 | Matsuura et al. |
| 8,720,448 B2 | 5/2014 | Reis et al. |
| 8,738,181 B2 | 5/2014 | Greer et al. |
| 8,821,376 B2 | 9/2014 | Tolkowsky |
| 8,827,948 B2 | 9/2014 | Romo et al. |
| 8,858,424 B2 | 10/2014 | Hasegawa et al. |
| 8,894,610 B2 | 11/2014 | Macnamara et al. |
| 8,929,631 B2 | 1/2015 | Pfister et al. |
| 8,945,095 B2 | 2/2015 | Blumenkranz et al. |
| 9,014,851 B2 | 4/2015 | Wong et al. |
| 9,023,060 B2 | 5/2015 | Cooper et al. |
| 9,084,623 B2 | 7/2015 | Gomez et al. |
| 9,125,639 B2 | 9/2015 | Mathis et al. |
| 9,129,417 B2 | 9/2015 | Zheng et al. |
| 9,138,129 B2 | 9/2015 | Diolaiti |
| 9,173,713 B2 | 11/2015 | Hart et al. |
| 9,183,354 B2 | 11/2015 | Baker et al. |
| 9,186,046 B2 | 11/2015 | Ramamurthy et al. |
| 9,199,372 B2 | 12/2015 | Henderson et al. |
| 9,226,796 B2 | 1/2016 | Bowling et al. |
| 9,256,940 B2 | 2/2016 | Carelsen et al. |
| 9,259,274 B2 | 2/2016 | Prisco |
| 9,272,416 B2 | 3/2016 | Hourtash et al. |
| 9,289,578 B2 | 3/2016 | Walker et al. |
| 9,302,702 B1 | 4/2016 | Schepmann et al. |
| 9,314,306 B2 | 4/2016 | Yu |
| 9,345,456 B2 | 5/2016 | Tsonton et al. |
| 9,358,682 B2 | 6/2016 | Morales |
| 9,452,276 B2 | 9/2016 | Duindam et al. |
| 9,459,087 B2 | 10/2016 | Dunbar et al. |
| 9,504,604 B2 | 11/2016 | Alvarez |
| 9,522,034 B2 | 12/2016 | Johnson et al. |
| 9,547,908 B1 | 1/2017 | Kim et al. |
| 9,561,083 B2 | 2/2017 | Yu et al. |
| 9,603,668 B2 | 3/2017 | Weingarten et al. |
| 9,622,827 B2 | 4/2017 | Yu et al. |
| 9,629,595 B2 | 4/2017 | Walker et al. |
| 9,629,682 B2 | 4/2017 | Wallace et al. |
| 9,636,184 B2 | 5/2017 | Lee et al. |
| 9,668,768 B2 | 6/2017 | Piron et al. |
| 9,675,422 B2 | 6/2017 | Hourtash et al. |
| 9,710,921 B2 | 7/2017 | Wong et al. |
| 9,713,509 B2 | 7/2017 | Schuh et al. |
| 9,717,563 B2 | 8/2017 | Tognaccini et al. |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,782,229 B2 | 10/2017 | Crawford et al. |
| 9,788,910 B2 | 10/2017 | Schuh |
| 9,789,608 B2 | 10/2017 | Itkowitz et al. |
| 9,839,481 B2 | 12/2017 | Blumenkranz et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |

(56) References Cited

U.S. PATENT DOCUMENTS

| | | |
|---|---|---|
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,123,755 B2 | 11/2018 | Walker et al. |
| 10,130,345 B2 | 11/2018 | Wong et al. |
| 10,130,427 B2 | 11/2018 | Tanner et al. |
| 10,136,950 B2 | 11/2018 | Schoenefeld |
| 10,136,959 B2 | 11/2018 | Mintz et al. |
| 10,143,360 B2 | 12/2018 | Roelle et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni |
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,251,713 B2 | 4/2019 | Morales et al. |
| 10,271,915 B2 | 4/2019 | Diolaiti et al. |
| 10,278,778 B2 | 5/2019 | State et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,342,410 B2 | 7/2019 | Schwartz et al. |
| 10,383,765 B2 | 8/2019 | Alvarez et al. |
| 10,398,518 B2 | 9/2019 | Yu et al. |
| 10,405,939 B2 | 9/2019 | Romo |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer et al. |
| 10,454,347 B2 | 10/2019 | Covington et al. |
| 10,464,209 B2 | 11/2019 | Ho et al. |
| 10,470,830 B2 | 11/2019 | Hill et al. |
| 10,482,599 B2 | 11/2019 | Mintz et al. |
| 10,489,913 B2 | 11/2019 | Shi |
| 10,492,741 B2 | 12/2019 | Walker et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan et al. |
| 10,531,864 B2 | 1/2020 | Wong et al. |
| 10,539,478 B2 | 1/2020 | Lin et al. |
| 10,543,048 B2 | 1/2020 | Noonan |
| 10,555,775 B2 | 2/2020 | Hoffman et al. |
| 10,555,778 B2 | 2/2020 | Ummalaneni |
| 10,575,906 B2 | 3/2020 | Wu |
| 10,582,907 B2 | 3/2020 | Chen et al. |
| 10,583,271 B2 | 3/2020 | Bogusky |
| 10,631,949 B2 | 4/2020 | Schuh et al. |
| 10,639,109 B2 | 5/2020 | Bovay et al. |
| 10,646,291 B2 | 5/2020 | Turner |
| 10,779,711 B2 | 9/2020 | Schena |
| 10,918,307 B2 | 2/2021 | Olson et al. |
| 11,135,023 B2 | 10/2021 | Larkin et al. |
| 11,172,895 B2 | 11/2021 | Dickhans et al. |
| 11,298,195 B2 | 4/2022 | Ye et al. |
| 11,311,343 B2 | 4/2022 | Lwin et al. |
| 2001/0000040 A1 | 3/2001 | Adams et al. |
| 2001/0021843 A1 | 9/2001 | Bosselmann et al. |
| 2001/0039421 A1 | 11/2001 | Heilbrun et al. |
| 2002/0035330 A1 | 3/2002 | Cline et al. |
| 2002/0065455 A1 | 5/2002 | Ben-Haim et al. |
| 2002/0077533 A1 | 6/2002 | Bieger et al. |
| 2002/0082612 A1 | 6/2002 | Moll et al. |
| 2002/0120188 A1 | 8/2002 | Brock et al. |
| 2002/0128535 A1 | 9/2002 | Kikuchi et al. |
| 2002/0161280 A1 | 10/2002 | Chatenever et al. |
| 2002/0173878 A1 | 11/2002 | Watanabe et al. |
| 2003/0045778 A1 | 3/2003 | Ohline et al. |
| 2003/0105603 A1 | 6/2003 | Hardesty |
| 2003/0125622 A1 | 7/2003 | Schweikard et al. |
| 2003/0158628 A1 | 8/2003 | Matsuoka et al. |
| 2003/0181809 A1 | 9/2003 | Hall et al. |
| 2003/0182091 A1 | 9/2003 | Kukuk |
| 2003/0195664 A1 | 10/2003 | Nowlin et al. |
| 2003/0199765 A1 | 10/2003 | Stetten et al. |
| 2003/0209096 A1 | 11/2003 | Pandey et al. |
| 2004/0047044 A1 | 3/2004 | Dalton |
| 2004/0072066 A1 | 4/2004 | Cho et al. |
| 2004/0176751 A1 | 9/2004 | Weitzner et al. |
| 2004/0186349 A1 | 9/2004 | Ewers et al. |
| 2004/0249267 A1 | 12/2004 | Gilboa |
| 2004/0257021 A1 | 12/2004 | Chang et al. |
| 2004/0263535 A1 | 12/2004 | Birkenbach et al. |
| 2004/0267477 A1 | 12/2004 | Scott et al. |
| 2005/0027397 A1 | 2/2005 | Niemeyer |
| 2005/0043718 A1 | 2/2005 | Madhani et al. |
| 2005/0060006 A1 | 3/2005 | Pflueger et al. |
| 2005/0065400 A1 | 3/2005 | Banik et al. |
| 2005/0080333 A1 | 4/2005 | Piron et al. |
| 2005/0085714 A1 | 4/2005 | Foley et al. |
| 2005/0107679 A1 | 5/2005 | Geiger et al. |
| 2005/0107917 A1 | 5/2005 | Smith et al. |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0193451 A1 | 9/2005 | Quistgaard et al. |
| 2005/0203382 A1 | 9/2005 | Govari et al. |
| 2005/0222554 A1 | 10/2005 | Wallace et al. |
| 2005/0234293 A1 | 10/2005 | Yamamoto et al. |
| 2005/0256398 A1 | 11/2005 | Hastings et al. |
| 2005/0261551 A1 | 11/2005 | Couvillon, Jr. et al. |
| 2005/0272975 A1 | 12/2005 | McWeeney et al. |
| 2006/0004286 A1 | 1/2006 | Chang et al. |
| 2006/0015096 A1 | 1/2006 | Hauck et al. |
| 2006/0025668 A1 | 2/2006 | Peterson et al. |
| 2006/0041293 A1 | 2/2006 | Mehdizadeh et al. |
| 2006/0058617 A1 | 3/2006 | Sano et al. |
| 2006/0058643 A1 | 3/2006 | Florent et al. |
| 2006/0079745 A1 | 4/2006 | Viswanathan |
| 2006/0084860 A1 | 4/2006 | Geiger et al. |
| 2006/0095066 A1 | 5/2006 | Chang et al. |
| 2006/0098851 A1 | 5/2006 | Shoham et al. |
| 2006/0149134 A1 | 7/2006 | Soper et al. |
| 2006/0161136 A1 | 7/2006 | Anderson et al. |
| 2006/0167440 A1 | 7/2006 | Cooper et al. |
| 2006/0173290 A1 | 8/2006 | Lavallee et al. |
| 2006/0178556 A1 | 8/2006 | Hasser et al. |
| 2006/0184016 A1 | 8/2006 | Glossop |
| 2006/0200026 A1 | 9/2006 | Wallace et al. |
| 2006/0200049 A1 | 9/2006 | Leo et al. |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2006/0287769 A1 | 12/2006 | Yanagita et al. |
| 2007/0013336 A1 | 1/2007 | Nowlin et al. |
| 2007/0032826 A1 | 2/2007 | Schwartz |
| 2007/0043455 A1 | 2/2007 | Viswanathan et al. |
| 2007/0055128 A1 | 3/2007 | Glossop |
| 2007/0055144 A1 | 3/2007 | Neustadter et al. |
| 2007/0073136 A1 | 3/2007 | Metzger |
| 2007/0083193 A1 | 4/2007 | Werneth et al. |
| 2007/0123748 A1 | 5/2007 | Meglan |
| 2007/0135886 A1 | 6/2007 | Maschke |
| 2007/0142971 A1 | 6/2007 | Schena et al. |
| 2007/0150155 A1 | 6/2007 | Kawai et al. |
| 2007/0156019 A1 | 7/2007 | Larkin et al. |
| 2007/0161857 A1 | 7/2007 | Durant et al. |
| 2007/0167743 A1 | 7/2007 | Honda et al. |
| 2007/0167801 A1 | 7/2007 | Webler et al. |
| 2007/0173694 A1 | 7/2007 | Tsuji et al. |
| 2007/0208252 A1 | 9/2007 | Makower |
| 2007/0232856 A1 | 10/2007 | Ueno et al. |
| 2007/0249911 A1 | 10/2007 | Simon |
| 2007/0253599 A1 | 11/2007 | White et al. |
| 2007/0269001 A1 | 11/2007 | Maschke |

(56) References Cited

U.S. PATENT DOCUMENTS

| | | |
|---|---|---|
| 2007/0287992 A1 | 12/2007 | Diolaiti et al. |
| 2007/0293721 A1 | 12/2007 | Gilboa |
| 2007/0299353 A1 | 12/2007 | Harlev et al. |
| 2008/0027313 A1 | 1/2008 | Shachar |
| 2008/0046122 A1 | 2/2008 | Manzo et al. |
| 2008/0071140 A1 | 3/2008 | Gattani et al. |
| 2008/0079421 A1 | 4/2008 | Jensen |
| 2008/0081982 A1 | 4/2008 | Simon et al. |
| 2008/0103389 A1 | 5/2008 | Begelman et al. |
| 2008/0108870 A1 | 5/2008 | Wiita et al. |
| 2008/0118118 A1 | 5/2008 | Berger |
| 2008/0118135 A1 | 5/2008 | Averbuch et al. |
| 2008/0123921 A1 | 5/2008 | Gielen et al. |
| 2008/0140087 A1 | 6/2008 | Barbagli |
| 2008/0147089 A1 | 6/2008 | Loh et al. |
| 2008/0159653 A1 | 7/2008 | Dunki-Jacobs et al. |
| 2008/0161681 A1 | 7/2008 | Hauck |
| 2008/0183064 A1 | 7/2008 | Chandonnet et al. |
| 2008/0183068 A1 | 7/2008 | Carls et al. |
| 2008/0183073 A1 | 7/2008 | Higgins et al. |
| 2008/0183188 A1 | 7/2008 | Carls et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218588 A1 | 9/2008 | Stetten |
| 2008/0218743 A1 | 9/2008 | Stetten et al. |
| 2008/0218770 A1 | 9/2008 | Moll et al. |
| 2008/0231221 A1 | 9/2008 | Ogawa |
| 2008/0243142 A1 | 10/2008 | Gildenberg |
| 2008/0249640 A1 | 10/2008 | Vittor et al. |
| 2008/0255505 A1 | 10/2008 | Carlson et al. |
| 2008/0262297 A1 | 10/2008 | Gilboa et al. |
| 2008/0275349 A1 | 11/2008 | Halperin et al. |
| 2008/0287963 A1 | 11/2008 | Rogers et al. |
| 2008/0300478 A1 | 12/2008 | Zuhars et al. |
| 2008/0306490 A1 | 12/2008 | Lakin et al. |
| 2008/0312501 A1 | 12/2008 | Hasegawa et al. |
| 2008/0312771 A1 | 12/2008 | Sugiura |
| 2009/0005768 A1 | 1/2009 | Sharareh et al. |
| 2009/0030307 A1 | 1/2009 | Govari et al. |
| 2009/0048611 A1 | 2/2009 | Funda et al. |
| 2009/0054729 A1 | 2/2009 | Mori et al. |
| 2009/0062611 A1 | 3/2009 | Toyama |
| 2009/0062813 A1 | 3/2009 | Prisco et al. |
| 2009/0076476 A1 | 3/2009 | Barbagli et al. |
| 2009/0076534 A1 | 3/2009 | Shelton et al. |
| 2009/0149867 A1 | 6/2009 | Glozman et al. |
| 2009/0184825 A1 | 7/2009 | Anderson |
| 2009/0198298 A1 | 8/2009 | Kaiser et al. |
| 2009/0227861 A1 | 9/2009 | Ganatra et al. |
| 2009/0228020 A1 | 9/2009 | Wallace et al. |
| 2009/0245600 A1 | 10/2009 | Hoffman et al. |
| 2009/0248036 A1 | 10/2009 | Hoffman et al. |
| 2009/0256905 A1 | 10/2009 | Tashiro |
| 2009/0259099 A1 | 10/2009 | Zhou et al. |
| 2009/0259230 A1 | 10/2009 | Khadem et al. |
| 2009/0262109 A1 | 10/2009 | Markowitz et al. |
| 2009/0287354 A1 | 11/2009 | Choi |
| 2009/0292166 A1 | 11/2009 | Ito et al. |
| 2009/0295797 A1 | 12/2009 | Sakaguchi |
| 2009/0324161 A1 | 12/2009 | Prisco |
| 2009/0326318 A1 | 12/2009 | Tognaccini et al. |
| 2010/0008555 A1 | 1/2010 | Trumer et al. |
| 2010/0030061 A1 | 2/2010 | Canfield et al. |
| 2010/0030115 A1 | 2/2010 | Fujimoto et al. |
| 2010/0039506 A1 | 2/2010 | Sarvestani et al. |
| 2010/0041949 A1 | 2/2010 | Tolkowsky |
| 2010/0054536 A1 | 3/2010 | Huang et al. |
| 2010/0069920 A1 | 3/2010 | Naylor et al. |
| 2010/0076263 A1 | 3/2010 | Tanaka et al. |
| 2010/0082041 A1 | 4/2010 | Prisco |
| 2010/0121138 A1 | 5/2010 | Goldenberg et al. |
| 2010/0121139 A1 | 5/2010 | OuYang et al. |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0168918 A1 | 7/2010 | Zhao et al. |
| 2010/0198170 A1 | 8/2010 | Umeda et al. |
| 2010/0204713 A1 | 8/2010 | Morales |
| 2010/0225209 A1 | 9/2010 | Goldberg et al. |
| 2010/0228266 A1 | 9/2010 | Hourtash |
| 2010/0234856 A1 | 9/2010 | Stoianovici et al. |
| 2010/0234857 A1 | 9/2010 | Itkowitz et al. |
| 2010/0240989 A1 | 9/2010 | Stoianovici et al. |
| 2010/0256812 A1 | 10/2010 | Tsusaka et al. |
| 2010/0290530 A1 | 11/2010 | Huang et al. |
| 2010/0292565 A1 | 11/2010 | Meyer et al. |
| 2010/0298641 A1 | 11/2010 | Tanaka |
| 2010/0328455 A1 | 12/2010 | Nam et al. |
| 2011/0009880 A1 | 1/2011 | Prisco et al. |
| 2011/0015484 A1 | 1/2011 | Alvarez et al. |
| 2011/0021926 A1 | 1/2011 | Spencer et al. |
| 2011/0054303 A1 | 3/2011 | Barrick et al. |
| 2011/0082366 A1 | 4/2011 | Scully et al. |
| 2011/0082462 A1 | 4/2011 | Suarez et al. |
| 2011/0092808 A1 | 4/2011 | Shachar et al. |
| 2011/0137122 A1 | 6/2011 | Kawai |
| 2011/0153252 A1 | 6/2011 | Govari et al. |
| 2011/0160570 A1 | 6/2011 | Kariv et al. |
| 2011/0184238 A1 | 7/2011 | Higgins et al. |
| 2011/0196199 A1 | 8/2011 | Donhowe et al. |
| 2011/0218676 A1 | 9/2011 | Okazaki |
| 2011/0234780 A1 | 9/2011 | Ito et al. |
| 2011/0238082 A1 | 9/2011 | Wenderow et al. |
| 2011/0245665 A1 | 10/2011 | Nentwick |
| 2011/0248987 A1 | 10/2011 | Mitchell |
| 2011/0249016 A1 | 10/2011 | Zhang et al. |
| 2011/0257480 A1 | 10/2011 | Takahashi et al. |
| 2011/0258842 A1 | 10/2011 | Dukesherer et al. |
| 2011/0270084 A1 | 11/2011 | Choi et al. |
| 2011/0276179 A1 | 11/2011 | Banks et al. |
| 2011/0277775 A1 | 11/2011 | Holop et al. |
| 2011/0319910 A1 | 12/2011 | Roelle et al. |
| 2012/0000427 A1 | 1/2012 | Nilsson |
| 2012/0046521 A1 | 2/2012 | Hunter et al. |
| 2012/0046522 A1 | 2/2012 | Naito |
| 2012/0056986 A1 | 3/2012 | Popovic |
| 2012/0059249 A1 | 3/2012 | Verard et al. |
| 2012/0062714 A1 | 3/2012 | Liu et al. |
| 2012/0065481 A1 | 3/2012 | Hunter et al. |
| 2012/0069167 A1 | 3/2012 | Liu et al. |
| 2012/0071752 A1 | 3/2012 | Sewell et al. |
| 2012/0071782 A1 | 3/2012 | Dutta et al. |
| 2012/0071822 A1 | 3/2012 | Romo et al. |
| 2012/0071894 A1 | 3/2012 | Tanner et al. |
| 2012/0082351 A1 | 4/2012 | Higgins et al. |
| 2012/0120305 A1 | 5/2012 | Takahashi |
| 2012/0123441 A1 | 5/2012 | Au et al. |
| 2012/0130217 A1 | 5/2012 | Kauphusman et al. |
| 2012/0136372 A1 | 5/2012 | Girbau et al. |
| 2012/0165656 A1 | 6/2012 | Montag et al. |
| 2012/0191079 A1 | 7/2012 | Moll et al. |
| 2012/0209069 A1 | 8/2012 | Popovic et al. |
| 2012/0209293 A1 | 8/2012 | Carlson et al. |
| 2012/0215094 A1 | 8/2012 | Rahimian et al. |
| 2012/0219185 A1 | 8/2012 | Hu et al. |
| 2012/0221007 A1 | 8/2012 | Batten et al. |
| 2012/0239060 A1 | 9/2012 | Orban, III |
| 2012/0253276 A1 | 10/2012 | Govari et al. |
| 2012/0283745 A1 | 11/2012 | Goldberg et al. |
| 2012/0283747 A1 | 11/2012 | Popovic |
| 2012/0289777 A1 | 11/2012 | Chopra et al. |
| 2012/0289783 A1 | 11/2012 | Duindam et al. |
| 2012/0302869 A1 | 11/2012 | Koyrakh et al. |
| 2012/0328077 A1 | 12/2012 | Bouvier |
| 2013/0018306 A1 | 1/2013 | Ludwin |
| 2013/0060146 A1 | 3/2013 | Yang et al. |
| 2013/0085330 A1 | 4/2013 | Ramamurthy et al. |
| 2013/0090530 A1 | 4/2013 | Ramamurthy et al. |
| 2013/0102846 A1 | 4/2013 | Sjostrom et al. |
| 2013/0123580 A1 | 5/2013 | Peters et al. |
| 2013/0131503 A1 | 5/2013 | Schneider et al. |
| 2013/0144116 A1 | 6/2013 | Cooper et al. |
| 2013/0165854 A1 | 6/2013 | Sandhu et al. |

(56) References Cited

U.S. PATENT DOCUMENTS

| | | |
|---|---|---|
| 2013/0165945 A9 | 6/2013 | Roelle et al. |
| 2013/0204124 A1 | 8/2013 | Duindam et al. |
| 2013/0209208 A1 | 8/2013 | Bailey et al. |
| 2013/0218005 A1 | 8/2013 | Desai et al. |
| 2013/0225942 A1 | 8/2013 | Holsing et al. |
| 2013/0243153 A1 | 9/2013 | Sra et al. |
| 2013/0246334 A1 | 9/2013 | Ahuja et al. |
| 2013/0259315 A1 | 10/2013 | Angot et al. |
| 2013/0274783 A1 | 10/2013 | Wynberg |
| 2013/0303891 A1 | 11/2013 | Chopra |
| 2013/0303892 A1 | 11/2013 | Zhao et al. |
| 2013/0325030 A1 | 12/2013 | Hourtash et al. |
| 2013/0345718 A1 | 12/2013 | Crawford et al. |
| 2014/0001235 A1 | 1/2014 | Shelton, IV |
| 2014/0051049 A1 | 2/2014 | Jarc et al. |
| 2014/0051985 A1 | 2/2014 | Fan et al. |
| 2014/0058406 A1 | 2/2014 | Tsekos et al. |
| 2014/0107390 A1 | 4/2014 | Brown et al. |
| 2014/0114180 A1 | 4/2014 | Jain et al. |
| 2014/0135985 A1 | 5/2014 | Coste-Maniere et al. |
| 2014/0142591 A1 | 5/2014 | Alvarez et al. |
| 2014/0148808 A1 | 5/2014 | Inkpen et al. |
| 2014/0163664 A1 | 6/2014 | Goldsmith |
| 2014/0180063 A1 | 6/2014 | Zhao et al. |
| 2014/0222207 A1 | 8/2014 | Bowling et al. |
| 2014/0235943 A1 | 8/2014 | Paris et al. |
| 2014/0243801 A1 | 8/2014 | Fanelli et al. |
| 2014/0243849 A1 | 8/2014 | Saglam et al. |
| 2014/0257333 A1 | 9/2014 | Blumenkranz et al. |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan et al. |
| 2014/0276937 A1 | 9/2014 | Wong et al. |
| 2014/0277333 A1 | 9/2014 | Lewis et al. |
| 2014/0296655 A1 | 10/2014 | Akhbardeh et al. |
| 2014/0296657 A1 | 10/2014 | Izmirli et al. |
| 2014/0296870 A1 | 10/2014 | Stern et al. |
| 2014/0309527 A1 | 10/2014 | Namati et al. |
| 2014/0309625 A1 | 10/2014 | Okamoto et al. |
| 2014/0316420 A1 | 10/2014 | Ballard et al. |
| 2014/0343416 A1 | 11/2014 | Panescu et al. |
| 2014/0343569 A1 | 11/2014 | Turner |
| 2014/0350391 A1 | 11/2014 | Prisco et al. |
| 2014/0357984 A1 | 12/2014 | Wallace et al. |
| 2014/0364739 A1 | 12/2014 | Liu et al. |
| 2014/0364870 A1 | 12/2014 | Alvarez et al. |
| 2015/0025549 A1 | 1/2015 | Kilroy et al. |
| 2015/0045675 A1 | 2/2015 | Chernomorsky |
| 2015/0051482 A1 | 2/2015 | Liu et al. |
| 2015/0054929 A1 | 2/2015 | Ito et al. |
| 2015/0057498 A1 | 2/2015 | Akimoto et al. |
| 2015/0073266 A1 | 3/2015 | Brannan et al. |
| 2015/0073267 A1 | 3/2015 | Brannan et al. |
| 2015/0088161 A1 | 3/2015 | Hata et al. |
| 2015/0104284 A1 | 4/2015 | Riedel et al. |
| 2015/0119628 A1 | 4/2015 | Bharat et al. |
| 2015/0119645 A1 | 4/2015 | Baldwin |
| 2015/0141808 A1 | 5/2015 | Elhawary et al. |
| 2015/0141858 A1 | 5/2015 | Razavi et al. |
| 2015/0142013 A1 | 5/2015 | Tanner et al. |
| 2015/0150635 A1 | 6/2015 | Kilroy et al. |
| 2015/0150636 A1 | 6/2015 | Hagn et al. |
| 2015/0202015 A1 | 7/2015 | Elhawary et al. |
| 2015/0223725 A1 | 8/2015 | Engel et al. |
| 2015/0223832 A1 | 8/2015 | Swaney et al. |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265087 A1 | 9/2015 | Messick, Jr. |
| 2015/0265359 A1 | 9/2015 | Camarillo |
| 2015/0265368 A1 | 9/2015 | Chopra et al. |
| 2015/0265807 A1 | 9/2015 | Park et al. |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0297299 A1 | 10/2015 | Yeung et al. |
| 2015/0311838 A1 | 10/2015 | Moule et al. |
| 2015/0313503 A1 | 11/2015 | Seibel et al. |
| 2015/0342695 A1 | 12/2015 | He et al. |
| 2015/0359597 A1 | 12/2015 | Gombert et al. |
| 2016/0000302 A1 | 1/2016 | Brown et al. |
| 2016/0000414 A1 | 1/2016 | Brown et al. |
| 2016/0000495 A1 | 1/2016 | Elliott et al. |
| 2016/0000520 A1 | 1/2016 | Lachmanovich et al. |
| 2016/0001038 A1 | 1/2016 | Romo et al. |
| 2016/0005168 A1 | 1/2016 | Merlet |
| 2016/0005220 A1 | 1/2016 | Weingarten et al. |
| 2016/0005576 A1 | 1/2016 | Tsukamoto |
| 2016/0008033 A1 | 1/2016 | Hawkins et al. |
| 2016/0016319 A1 | 1/2016 | Remirez et al. |
| 2016/0045269 A1 | 2/2016 | Elhawary et al. |
| 2016/0051221 A1 | 2/2016 | Dickhans et al. |
| 2016/0066794 A1 | 3/2016 | Klinder et al. |
| 2016/0073928 A1 | 3/2016 | Soper et al. |
| 2016/0075030 A1 | 3/2016 | Takahashi et al. |
| 2016/0081568 A1 | 3/2016 | Kolberg et al. |
| 2016/0100772 A1 | 4/2016 | Ikuma et al. |
| 2016/0111192 A1 | 4/2016 | Suzara |
| 2016/0128781 A1 | 5/2016 | Blohm et al. |
| 2016/0128992 A1 | 5/2016 | Hudson et al. |
| 2016/0135908 A1 | 5/2016 | Takahashi et al. |
| 2016/0166320 A1 | 6/2016 | Ciulla et al. |
| 2016/0183841 A1 | 6/2016 | Duindam et al. |
| 2016/0199134 A1 | 7/2016 | Brown et al. |
| 2016/0206389 A1 | 7/2016 | Miller et al. |
| 2016/0213432 A1 | 7/2016 | Flexman et al. |
| 2016/0228032 A1 | 8/2016 | Walker et al. |
| 2016/0249990 A1 | 9/2016 | Glozman et al. |
| 2016/0270865 A1 | 9/2016 | Landey et al. |
| 2016/0278865 A1 | 9/2016 | Capote et al. |
| 2016/0287053 A1 | 10/2016 | Miura et al. |
| 2016/0287111 A1 | 10/2016 | Jacobsen et al. |
| 2016/0287279 A1 | 10/2016 | Bovay et al. |
| 2016/0287346 A1 | 10/2016 | Hyodo et al. |
| 2016/0314710 A1 | 10/2016 | Jarc et al. |
| 2016/0331469 A1 | 11/2016 | Hall et al. |
| 2016/0338787 A1 | 11/2016 | Popovic et al. |
| 2016/0346038 A1 | 12/2016 | Helgeson et al. |
| 2016/0346924 A1 | 12/2016 | Hasegawa et al. |
| 2016/0354057 A1 | 12/2016 | Hansen et al. |
| 2016/0360947 A1 | 12/2016 | Iida et al. |
| 2016/0360949 A1 | 12/2016 | Hyodo et al. |
| 2016/0372743 A1 | 12/2016 | Cho et al. |
| 2017/0000574 A1 | 1/2017 | Itkowitz et al. |
| 2017/0007337 A1 | 1/2017 | Dan |
| 2017/0023423 A1 | 1/2017 | Jackson et al. |
| 2017/0055851 A1 | 3/2017 | Al-Ali et al. |
| 2017/0056215 A1 | 3/2017 | Nagesh et al. |
| 2017/0068796 A1 | 3/2017 | Passerini et al. |
| 2017/0071456 A1 | 3/2017 | Ratnakar |
| 2017/0079725 A1 | 3/2017 | Hoffman et al. |
| 2017/0079726 A1 | 3/2017 | Hoffman et al. |
| 2017/0084027 A1 | 3/2017 | Mintz et al. |
| 2017/0095299 A1 | 4/2017 | Hendrick et al. |
| 2017/0100197 A1 | 4/2017 | Zubiate et al. |
| 2017/0106904 A1 | 4/2017 | Hanson et al. |
| 2017/0119412 A1 | 5/2017 | Noonan et al. |
| 2017/0119474 A1 | 5/2017 | Kronman |
| 2017/0119481 A1* | 5/2017 | Romo ............... A61B 1/00096 |
| 2017/0135710 A1 | 5/2017 | Hasegawa et al. |
| 2017/0135718 A1 | 5/2017 | Lyons |
| 2017/0135833 A1 | 5/2017 | Syed |
| 2017/0143442 A1 | 5/2017 | Tesar et al. |
| 2017/0165503 A1 | 6/2017 | Hautvast et al. |
| 2017/0181809 A1 | 6/2017 | Panescu et al. |
| 2017/0189118 A1 | 7/2017 | Chopra et al. |
| 2017/0189131 A1 | 7/2017 | Weir |
| 2017/0202624 A1 | 7/2017 | Atarot et al. |
| 2017/0202627 A1 | 7/2017 | Sramek et al. |
| 2017/0209073 A1 | 7/2017 | Sramek et al. |
| 2017/0209162 A1 | 7/2017 | Sperry et al. |
| 2017/0215808 A1 | 8/2017 | Shimol et al. |
| 2017/0215969 A1 | 8/2017 | Zhai et al. |

(56) References Cited

U.S. PATENT DOCUMENTS

| | | |
|---|---|---|
| 2017/0231647 A1 | 8/2017 | Saunders et al. |
| 2017/0238807 A9 | 8/2017 | Vertikov |
| 2017/0245854 A1 | 8/2017 | Zemlok et al. |
| 2017/0245885 A1 | 8/2017 | Lenker et al. |
| 2017/0251988 A1 | 9/2017 | Weber et al. |
| 2017/0258366 A1 | 9/2017 | Tupin, Jr. et al. |
| 2017/0280978 A1 | 10/2017 | Yamamoto et al. |
| 2017/0281049 A1 | 10/2017 | Yamamoto et al. |
| 2017/0290631 A1 | 10/2017 | Lee et al. |
| 2017/0296032 A1 | 10/2017 | Li |
| 2017/0296202 A1 | 10/2017 | Brown |
| 2017/0303889 A1 | 10/2017 | Grim et al. |
| 2017/0303941 A1 | 10/2017 | Eisner |
| 2017/0304015 A1 | 10/2017 | Tavallaei et al. |
| 2017/0325715 A1 | 11/2017 | Mehendale et al. |
| 2017/0325896 A1 | 11/2017 | Donhowe et al. |
| 2017/0326337 A1 | 11/2017 | Romoscanu et al. |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360508 A1 | 12/2017 | Germain et al. |
| 2018/0025666 A1 | 1/2018 | Ho et al. |
| 2018/0036033 A1 | 2/2018 | Ignagni et al. |
| 2018/0055576 A1 | 3/2018 | Koyrakh et al. |
| 2018/0055582 A1 | 3/2018 | Krimsky |
| 2018/0064498 A1 | 3/2018 | Kapadia et al. |
| 2018/0098690 A1 | 4/2018 | Iwaki |
| 2018/0098817 A1 | 4/2018 | Nichogi |
| 2018/0169671 A1 | 6/2018 | Winter et al. |
| 2018/0199999 A1 | 7/2018 | Syverson et al. |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0250083 A1 | 9/2018 | Schuh et al. |
| 2018/0263568 A1 | 9/2018 | Yi et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289394 A1 | 10/2018 | Shah |
| 2018/0289431 A1 | 10/2018 | Draper et al. |
| 2018/0296281 A1 | 10/2018 | Yeung et al. |
| 2018/0308247 A1 | 10/2018 | Gupta |
| 2018/0325499 A1 | 11/2018 | Landey et al. |
| 2018/0333044 A1 | 11/2018 | Jenkins |
| 2018/0338799 A1 | 11/2018 | Hladio et al. |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000568 A1 | 1/2019 | Connolly et al. |
| 2019/0000576 A1 | 1/2019 | Mintz et al. |
| 2019/0046814 A1 | 2/2019 | Senden et al. |
| 2019/0066314 A1 | 2/2019 | Abhari et al. |
| 2019/0083183 A1 | 3/2019 | Moll et al. |
| 2019/0083187 A1 | 3/2019 | Danitz et al. |
| 2019/0086349 A1 | 3/2019 | Nelson et al. |
| 2019/0110839 A1 | 4/2019 | Rafii-Tari et al. |
| 2019/0125164 A1 | 5/2019 | Roelle et al. |
| 2019/0139216 A1 | 5/2019 | Georgescu et al. |
| 2019/0151148 A1 | 5/2019 | Alvarez et al. |
| 2019/0167366 A1 | 6/2019 | Ummalaneni et al. |
| 2019/0167367 A1 | 6/2019 | Walker et al. |
| 2019/0175009 A1 | 6/2019 | Mintz et al. |
| 2019/0175062 A1 | 6/2019 | Rafii-Tari et al. |
| 2019/0175799 A1* | 6/2019 | Hsu .................. A61B 10/0283 |
| 2019/0183585 A1 | 6/2019 | Rafii-Tari et al. |
| 2019/0183587 A1 | 6/2019 | Rafii-Tari et al. |
| 2019/0201106 A1 | 7/2019 | Siemionow et al. |
| 2019/0209252 A1 | 7/2019 | Walker et al. |
| 2019/0216548 A1 | 7/2019 | Ummalaneni |
| 2019/0216576 A1 | 7/2019 | Eyre et al. |
| 2019/0223974 A1 | 7/2019 | Romo et al. |
| 2019/0228525 A1 | 7/2019 | Mintz et al. |
| 2019/0246882 A1 | 8/2019 | Graetzel et al. |
| 2019/0262084 A1 | 8/2019 | Roh et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata et al. |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan et al. |
| 2019/0298460 A1 | 10/2019 | Al-Jadda et al. |
| 2019/0298465 A1 | 10/2019 | Chin et al. |
| 2019/0328213 A1 | 10/2019 | Landey et al. |
| 2019/0336238 A1 | 11/2019 | Yu et al. |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000530 A1 | 1/2020 | DeFonzo et al. |
| 2020/0000533 A1 | 1/2020 | Schuh et al. |
| 2020/0008874 A1 | 1/2020 | Barbagli et al. |
| 2020/0022767 A1 | 1/2020 | Hill et al. |
| 2020/0038123 A1 | 2/2020 | Graetzel et al. |
| 2020/0039086 A1 | 2/2020 | Meyer et al. |
| 2020/0046434 A1 | 2/2020 | Graetzel et al. |
| 2020/0054405 A1 | 2/2020 | Schuh et al. |
| 2020/0054408 A1 | 2/2020 | Schuh et al. |
| 2020/0060516 A1 | 2/2020 | Baez, Jr. |
| 2020/0078103 A1 | 3/2020 | Duindam et al. |
| 2020/0085516 A1 | 3/2020 | DeFonzo et al. |
| 2020/0093549 A1 | 3/2020 | Chin et al. |
| 2020/0093554 A1 | 3/2020 | Schuh et al. |
| 2020/0100845 A1 | 4/2020 | Julian |
| 2020/0100853 A1 | 4/2020 | Ho et al. |
| 2020/0100855 A1 | 4/2020 | Leparmentier et al. |
| 2020/0101264 A1 | 4/2020 | Jiang |
| 2020/0107894 A1 | 4/2020 | Wallace et al. |
| 2020/0121502 A1 | 4/2020 | Kintz |
| 2020/0146769 A1 | 5/2020 | Eyre et al. |
| 2020/0155084 A1 | 5/2020 | Walker et al. |
| 2020/0170630 A1 | 6/2020 | Wong et al. |
| 2020/0170720 A1 | 6/2020 | Ummalaneni |
| 2020/0171660 A1 | 6/2020 | Ho et al. |
| 2020/0188043 A1 | 6/2020 | Yu et al. |
| 2020/0197112 A1 | 6/2020 | Chin et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0237458 A1 | 7/2020 | DeFonzo et al. |
| 2020/0246591 A1 | 8/2020 | Bogusky |
| 2020/0261172 A1 | 8/2020 | Romo et al. |
| 2020/0268459 A1 | 8/2020 | Noonan |
| 2020/0268460 A1 | 8/2020 | Tse et al. |
| 2020/0281787 A1 | 9/2020 | Ruiz |
| 2020/0297437 A1 | 9/2020 | Schuh et al. |
| 2020/0305922 A1 | 10/2020 | Yan et al. |
| 2020/0305983 A1 | 10/2020 | Yampolsky et al. |
| 2020/0305989 A1 | 10/2020 | Schuh et al. |
| 2020/0315717 A1 | 10/2020 | Bovay et al. |
| 2020/0315723 A1 | 10/2020 | Hassan et al. |
| 2020/0323596 A1 | 10/2020 | Moll et al. |
| 2020/0330167 A1 | 10/2020 | Romo et al. |
| 2021/0196312 A1 | 7/2021 | Plewe et al. |
| 2021/0196399 A1 | 7/2021 | Plewe |
| 2022/0296312 A1 | 9/2022 | Ye et al. |
| 2022/0371202 A1 | 11/2022 | Schoessler et al. |

FOREIGN PATENT DOCUMENTS

| | | |
|---|---|---|
| CN | 1846181 A | 10/2006 |
| CN | 1857877 A | 11/2006 |
| CN | 101147676 A | 3/2008 |
| CN | 101222882 A | 7/2008 |
| CN | 102316817 A | 1/2012 |
| CN | 101325920 B | 2/2012 |
| CN | 102341057 A | 2/2012 |

(56) References Cited

FOREIGN PATENT DOCUMENTS

| | | |
|---|---|---|
| CN | 102458295 A | 5/2012 |
| CN | 102973317 A | 3/2013 |
| CN | 103565529 A | 2/2014 |
| CN | 103705307 A | 4/2014 |
| CN | 103735313 A | 4/2014 |
| CN | 102458295 B | 6/2014 |
| CN | 103930063 A | 7/2014 |
| CN | 102711586 B | 6/2015 |
| CN | 103767659 B | 6/2015 |
| CN | 105030331 A | 11/2015 |
| CN | 105208960 A | 12/2015 |
| CN | 105511881 A | 4/2016 |
| CN | 105559850 A | 5/2016 |
| CN | 105559886 A | 5/2016 |
| CN | 106097353 A | 11/2016 |
| CN | 104758066 B | 5/2017 |
| CN | 107028659 A | 8/2017 |
| CN | 103813748 B | 4/2018 |
| CN | 107997778 A | 5/2018 |
| CN | 108348139 A | 7/2018 |
| CN | 108430373 A | 8/2018 |
| CN | 104931059 B | 9/2018 |
| CN | 104684502 B | 10/2018 |
| CN | 109753866 A | 5/2019 |
| CN | 106821498 B | 2/2020 |
| DE | 102013100605 A1 | 7/2014 |
| EP | 0347098 B1 | 2/1996 |
| EP | 1250986 A2 | 10/2002 |
| EP | 1566150 A2 | 8/2005 |
| EP | 1800593 A1 | 6/2007 |
| EP | 2158834 A1 | 3/2010 |
| EP | 2392435 A2 | 12/2011 |
| EP | 3025630 A1 | 6/2016 |
| EP | 2470089 B1 | 8/2018 |
| JP | 2011088260 A | 5/2011 |
| JP | 2016526958 A | 9/2016 |
| JP | 2016529999 A | 9/2016 |
| JP | 2019505245 A | 2/2019 |
| JP | 2019508072 A | 3/2019 |
| JP | 2021525584 A | 9/2021 |
| KR | 20140009359 A | 1/2014 |
| KR | 20180084751 A | 7/2018 |
| RU | 2569699 C2 | 11/2015 |
| WO | 200156457 A1 | 8/2001 |
| WO | 2004029782 A2 | 4/2004 |
| WO | 2005078128 A1 | 8/2005 |
| WO | 2006079108 A1 | 7/2006 |
| WO | 2006122061 A1 | 11/2006 |
| WO | 2007041094 A1 | 4/2007 |
| WO | 2007120952 A2 | 10/2007 |
| WO | 2009097461 A1 | 8/2009 |
| WO | 2009120940 A2 | 10/2009 |
| WO | 2010127162 A1 | 11/2010 |
| WO | 2011002215 A3 | 4/2011 |
| WO | 2011132409 A1 | 10/2011 |
| WO | 2012044334 A2 | 4/2012 |
| WO | 2012082719 A1 | 6/2012 |
| WO | 2014114551 A1 | 7/2014 |
| WO | 2014186715 A1 | 11/2014 |
| WO | 2015023665 A1 | 2/2015 |
| WO | 2015089013 A1 | 6/2015 |
| WO | 2015142957 A1 | 9/2015 |
| WO | 2016142693 A1 | 9/2016 |
| WO | 2017036774 A1 | 3/2017 |
| WO | 2017048194 A1 | 3/2017 |
| WO | 2017053698 A1 | 3/2017 |
| WO | 2017066108 A1 | 4/2017 |
| WO | 2017075085 A1 | 5/2017 |
| WO | 2017075574 A1 | 5/2017 |
| WO | 2017146890 A1 | 8/2017 |
| WO | 2017167754 A1 | 10/2017 |
| WO | 2018098477 A1 | 5/2018 |
| WO | 2018144636 A1 | 8/2018 |
| WO | 2018160288 A1 | 9/2018 |
| WO | 2019174953 A1 | 9/2019 |
| WO | 2019210322 A1 | 10/2019 |
| WO | 2021198906 A1 | 10/2021 |

OTHER PUBLICATIONS

Non-Final Rejection for U.S. Appl. No. 17/208,874, dated Feb. 2, 2022, 8 pages.
Notice of Allowance for U.S. Appl. No. 17/208,874 dated Apr. 13, 2023, 8 pages.
Search Report for appl No. PCTIB2021052625, dated Jul. 2, 2021, 5 pages.
Written Opinion for appl No. PCTIB2021052625, dated Jul. 2, 2021, 6 pages.
Office Action from Japanese Patent Application No. 2022-559640, issued on Oct. 15, 2024, pp. 1-11.
Al-Ahmad et al., dated 2005, Early experience with a computerized robotically controlled catheter system, Journal of Interventional Cardiac Electrophysiology, 12:199-202, 4 pages.
Blankenstein, Jun. 2008, Dynamic Registration and High Speed Visual Servoing in Robot-Assisted Surgery, Katholieke Universiteit Leuven, Leuven, Belgium, 96 pages.
Ciuti et al, 2012, Intra-Operative Monocular 3D Reconstruction for Image-Guided Navigation in Active Locomotion Capsule Endoscopy. Biomedical Robotics And Biomechatronics (Biorob), 4th IEEE Ras & Embs International Conference on IEEE, 7 pages.
Darwiche, 2015, Operative technique and early experience for robotic assisted laparoscopic nephroureterectomy (RALNU) using da Vinci XI, SpringerPlus, 4:298, 5 pages.
Fallavoliita et al., 2010, Acquiring Multiview C-Arm Images to Assist Cardiac Ablation Procedures, EURASIP Journal on Image and Video Processing, vol. 2010, Article ID 871408, pp. 1-10.
Final Rejection for U.S. Appl. No. 17/120,790, dated Aug. 27, 2021, 8 pages.
Gutierrez et al., Mar. 2008, A Practical Global Distortion Correction Method for an Image Intensifier Based X-Ray Fluoroscopy System, Med. Phys, 35(3):997-1007, 11 pages.
Haigron et al., 2004, Depth-map-based scene analysis for active navigation in virtual angioscopy, IEEE Transactions on Medical Imaging, 23( 11 ): 1380-1390, 11 pages.
Hansen Medical, Inc. 2005, System Overview, product brochure, 2 pp., dated as available at http://hansenmedical.com/system.aspx on Jul. 14, 2006 (accessed Jun. 25, 2019 using the internet archive way back machine).
Hansen Medical, Inc. Bibliography, product brochure, 1 p., dated as available athttp://hansenmedical.com/bibliography.aspx on Jul. 14, 2006 (accessed Jun. 25, 2019 using the internet archive way back machine).
Hansen Medical, Inc. dated 2007, Introducing the Sensei Robotic Catheter System, product brochure, 10 pages.
Hansen Medical, Inc. dated 2009, Sensei X Robotic Catheter System, product brochure, 2 pp.
Hansen Medical, Inc. Technology Advantages, product brochure, 1 p., dated as available at http://hansenmedical.com/advantages.aspx on Jul. 13, 2006 (accessed Jun. 25, 2019 using the internet archive way back machine).
He, Kaiming, Georgia Gkioxari, Piotr Dollár, and Ross Girshick. "Mask R-cnn." In Computer Vision (ICCV), 2017 IEEE International Conference on. IEEE, 2017. 12 pages.
International Preliminary Report on Patentability and Written Opinion for Appl. No. PCT/IB2020/061908, dated Jul. 5, 2022, 7 pages.
International search report and written opinion dated Dec. 18, 2019 for PCT/US2019/53600, 9 pages.
Kiraly et al, 2002, Three-dimensional Human Airway Segmentation Methods for Clinical Virtual Bronchoscopy, Acad Radio!, 9:1153-1168, 16 pages.
Kiraly et al., Sep. 2004, Three-dimensional path planning for virtual bronchoscopy, IEEE Transactions on Medical Imaging, 23(9):1365-1379, 15 pages.
Konen et al., 1998, The VN-project endoscopic image processing for neurosurgery, Computer Aided Surgery, 3:1-6 , 6 pages.

(56) References Cited

OTHER PUBLICATIONS

Kukuk, Oct. 5, 2001, TBNA-protocols: Guiding TransBronchial Needle Aspirations Without a Computer in the Operating Room, MICCAI 2001, 2208:997-1006.
Kumar et al., 2014, Stereoscopic visualization of laparoscope image using depth information from 3D model, Computer methods and programs in biomedicine 113(3):862-868, 7 pages.
Lawton et al., 1999, Ribbons and groups: A thin rod theory for catheters and filaments, J. Phys. A., 1999, 32:1709-1735, 27 pages.
Livatino et al., 2015, Stereoscopic visualization and 3-D technologies in medical endoscopic teleoperation, IEEE, 11 pages.
Luo et al., 2010, Modified hybrid bronchoscope tracking based on sequential monte carlo sampler: Dynamic phantom validation, Asian Conference on Computer Vision. Springer, Berlin, Heidelberg, 13 pages.
Marrouche et al., dated May 6, 2005, AB32-1, Preliminary human experience using a novel robotic catheter remote control, Heart Rhythm, 2(5):S63, 1 page.
Mayo Clinic, Robotic Surgery, https://www.mayoclinic.org/tests-procedures/robotic-surgery/about/pac- 20394974?p=1, downloaded from the internet on Jul. 12, 2018, 2 pgs.
Mourgues et al., 2002, Flexible calibration of actuated stereoscopic endoscope for overlay in robot 672 assisted surgery, International Conference on Medical Image Computing and Computer-Assisted Intervention. SprinQer, Berlin, HeidelberQ, 10 pages.
Nadeem et al., 2016, Depth Reconstruction and Computer-Aided Polyp Detection in Optical Colonoscopy Video Frames, arXiv preprint arXiv:1609.01329, 12 pages.
Zhou et al., 2010, Synthesis of stereoscopic views from monocular endoscopic videos, Compute Vision and Pattern Recognition Workshops (CVPRW), 2010 IEEE Computer Society Conference on IEE, 8 pages.
Non Final Rejection for U.S. Appl. No. 17/120,790, dated May 20, 2021, 13 pages.
Notice of Allowance for U.S. Appl. No. 17/120,790, dated Dec. 8, 2021, 8 pages.
Notice of Allowance for U.S. Appl. No. 17/120,790, dated Jan. 18, 2022, 5 pages.
Oh et al., dated May 2005, P5-75, Novel robotic catheter remote control system: safety and accuracy in delivering RF Lesions in all 4 cardiac chambers, Heart Rhythm, 2(5):S277-S278.
Point Cloud, Sep. 10, 2010, Wikipedia, 2 pp.
Racadio et al., Dec. 2007, Live 3D guidance in the interventionail radiology suite, AJR, 189:W357-W364, 8 pages.
Reddy et al., May 2005, P1-53. Porcine pulmonary vein ablation using a novel robotic catheter control system and real-time integration of CT imaging with electroanatomical mapping, Hearth Rhythm, 2(5):S121, 1 page.
Sasaki, 2017, Laparoscopic hemicolectomy for a patient with situs inversus totalis: a case report, Int. J. Surg. Case Rep. 41 :93-96, 4 pages.
Sato et al., 2016, Techniques of stapler-based navigational thoracoscopic segmentectomy using virtual assisted lung mapping (VAL-MAP), Journal of Thoracic Disease, 8(Suppl 9):S716.
Shen et al., 2015, Robust camera localisation with depth reconstruction for bronchoscopic navigation. International Journal of Computer Assisted Radiology and Surgery, 10(6):801-813, 13 pages.
Shi et al., Sep. 14-18, 2014, Simultaneous catheter and environment modeling for trans-catheter aortic valve implantation, IEEE/RSJ International Conference on Intelligent Robots and Systems, pp. 2024-2202.
Slepian, dated 2010, Robotic Catheter Intervention: the Hansen Medical Sensei Robot Catheter System, PowerPoint presentation, 28 pages.
Solheim et ai., May 14, 2009, Navigated resection of giant intracranial meningiomas based on intraoperative 30 ultrasound, Acta Neurochir, 151:1143-1151.
Solomon et al., Dec. 2000, Three-dimensional CT-Guided Bronchoscopy With a Real-Time Electromagnetic Position Sensor a Comparison of Two Image Registration Methods, Chest, 118(6):1783-1787.
Song et al., 2012, Autonomous and stable tracking of endoscope instrument tools with monocular camera, Advanced Intelligent Mechatronics (AIM), 2012 IEEE-ASME International Conference on.IEEE, 6 pages.
Vemuri et al., Dec. 2015, Inter-operative biopsy site relocations in endoluminal surgery, IEEE Transactions on Biomedical Engineering, Institute of Electrical and Electronics Engineers, < 10 .1109/T8ME 2015.2503981 >, 13 pages.
Verdaasdonk et al., Jan. 23, 2012, Effect of Microsecond Pulse Length and Tip Shape on Explosive Bubble Formation of 2.78 µm Er,Cr;YSGG and 2.94 µm Er:YAG laser, Proceedings of SPIE, vol. 8221, 12, 1 pages.
Wilson et al., 2008, A Buyer's Guide to Electromagnetic Tracking Systems for Clinical Applications, Proc. of SPCI, 6918:691828-1, 12 pages.
Yip et al., 2012, Tissue tracking and registration for image-guided surgery, IEEE transactions on medical imaging 31 (11 ):2169-2182, 14 pages.
Examination Report from European Patent Application No. 21782289. 9, mailed on Dec. 10, 2024, pp. 1-3.
CN Office Action for Appl. No. 202080091098X, dated Feb. 22, 2023, 16 pages.
CN 2nd Office Action for Appl. No. 202080091098, dated Sep. 14, 2023, 7 pages.
EP Search Report for Appl. No. 20910116.1, dated Dec. 4, 2023, 9 pages.
CN Office Action for Appl. No. 202080091098.X, dated Jan. 26, 2024, 8 pages.
International Search Report and Written Opinion, dated Mar. 11, 2021, for PCT/IB2020/061908, 10-pages.
JP Examination Report for Application No. 2022-540385, dated Aug. 28, 2024, 37—pages with translation.
EP Examination Report for Appl. No. 20910116.1, dated Aug. 16, 2024, 4 pages.
JP Office Action for Application No. 2022-540385, dated Sep. 24, 2024, 11—pages with translation.
Non-Final Office Action from U.S. Appl. No. 17/716,962, dated Nov. 7, 2024, 9 pages.
International Search Report and Written Opinion from PCT Application No. PCT/IB2025/052948, dated Jun. 27, 2025, 12 pages.

\* cited by examiner

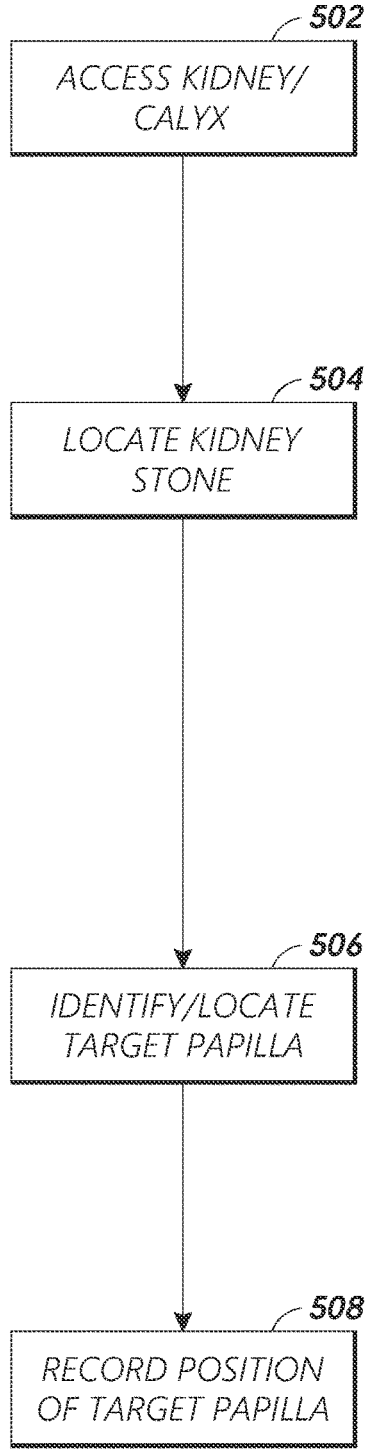
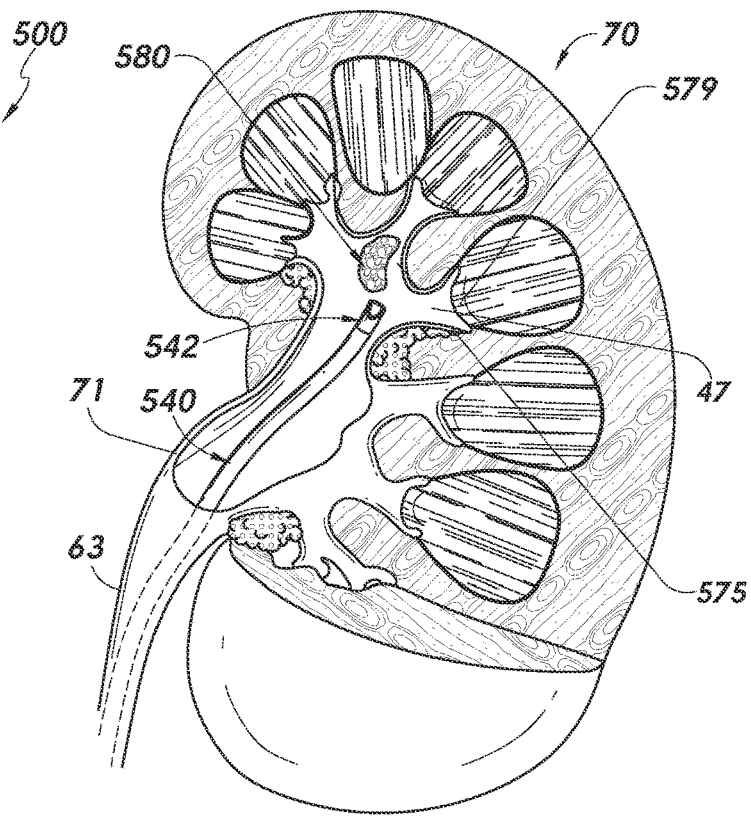
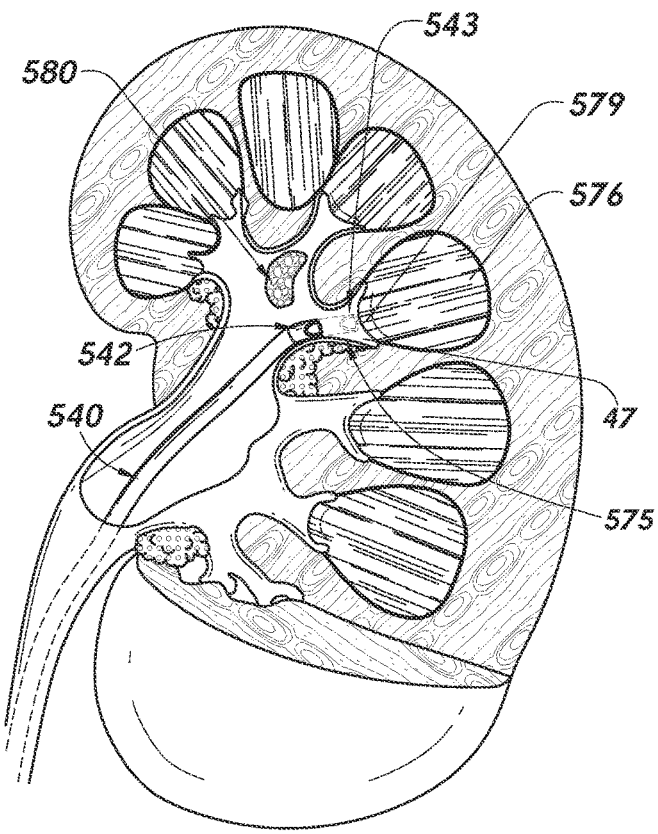
FIG. 5-1
FIG. 6-1

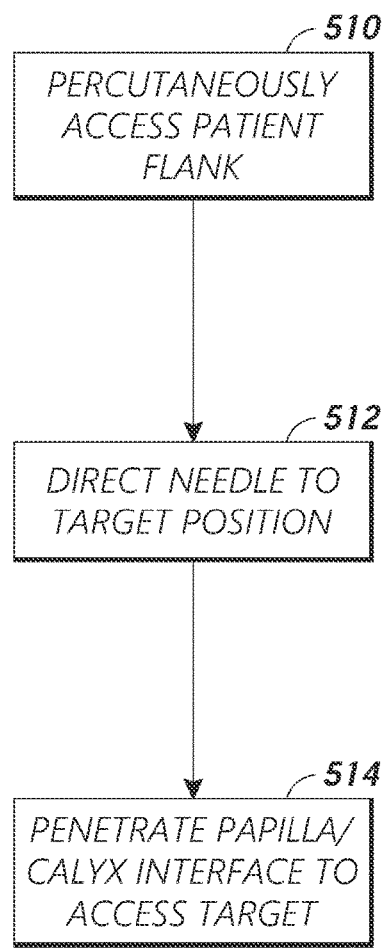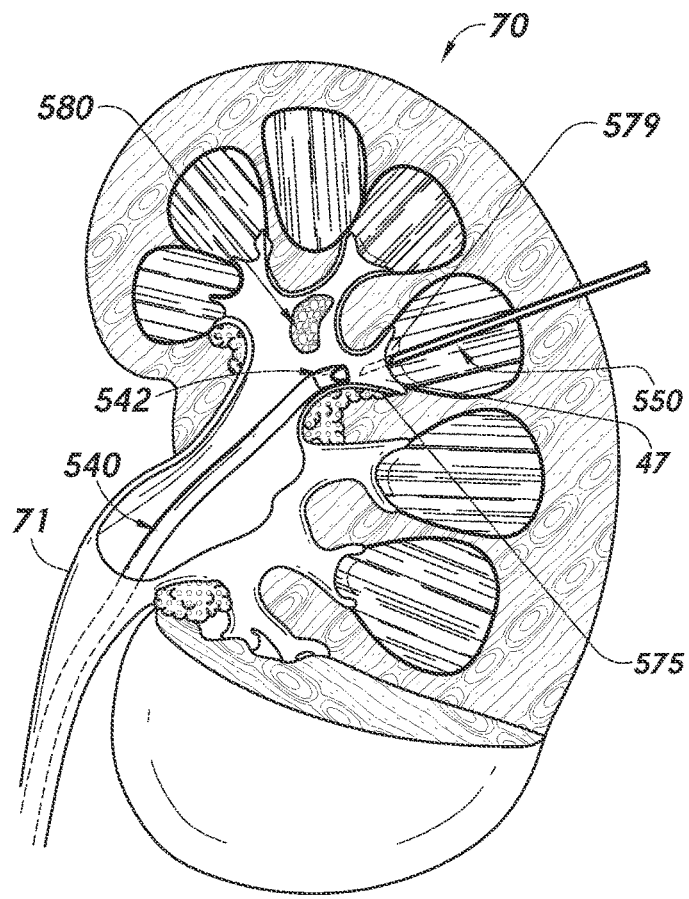
FIG. 5-2
FIG. 6-2

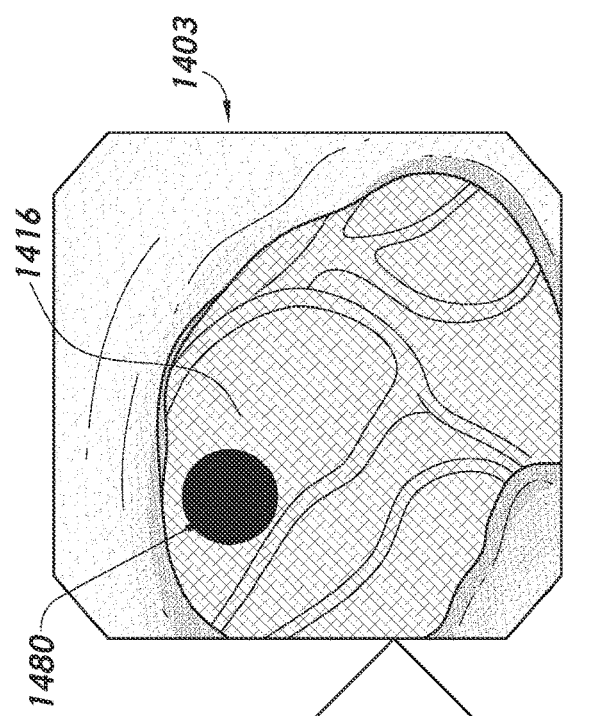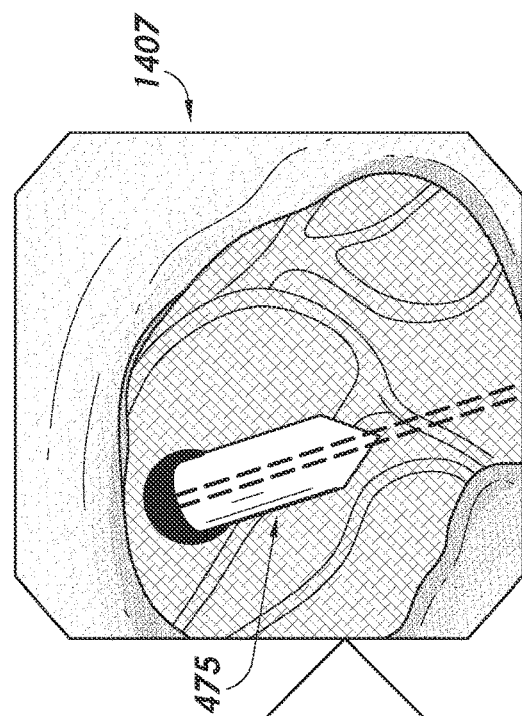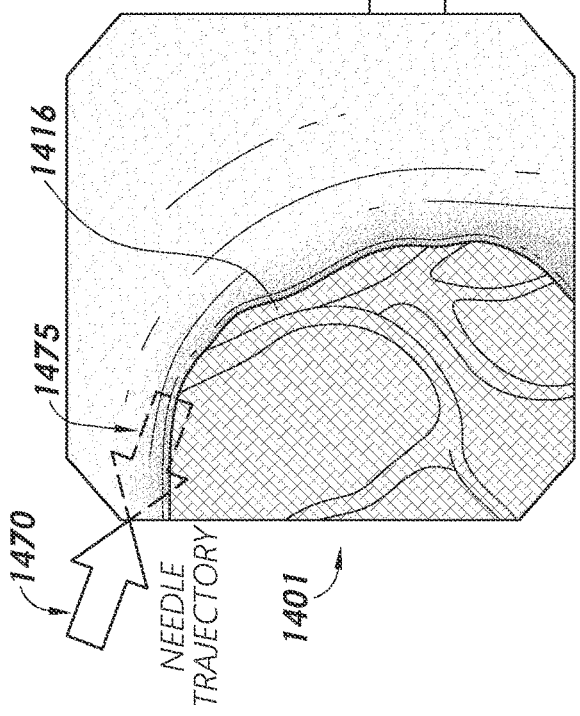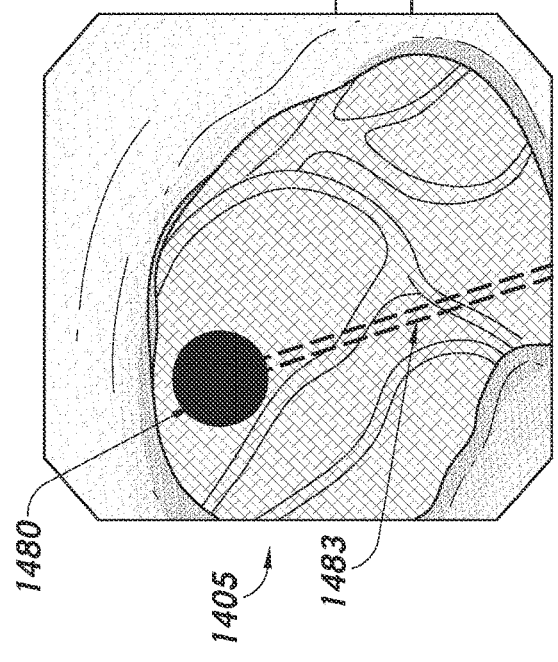
FIG. 14-1
FIG. 14-2

ENDOSCOPIC ANATOMICAL FEATURE TRACKING

RELATED APPLICATION(S)

This application is a divisional of U.S. patent application Ser. No. 17/208,874, filed Mar. 22, 2021, now U.S. Pat. No. 11,737,663, and entitled "TARGET ANATOMICAL FEATURE LOCALIZATION," which claims priority to U.S. Provisional Application No. 63/001,870, filed Mar. 30, 2020, and entitled "TARGET ANATOMICAL FEATURE LOCALIZATION," the disclosures of which are hereby incorporated by reference in their entirety.

BACKGROUND

Field

The present disclosure relates to the field of medical procedures.

Description of Related Art

Various medical procedures involve the use of one or more scope and/or percutaneous access instruments. The improper positioning or advancement of such devices can result in certain physiological and procedural complications.

SUMMARY

Described herein are systems, devices, and methods to facilitate the identification, tracking, and targeting of various anatomical features based on certain sensor- and/or image-based position information, which may be obtained using, for example, a scope device or other medical instrument. Target anatomical feature localization in accordance with aspects of the present disclosure can facilitate the targeting of the anatomical feature(s) in connection with a medical procedure, such as nephroscopy or other procedure accessing of the renal anatomy, for example.

In some implementations, the present disclosure relates to a method of localizing a target papilla. The method comprises advancing a ureteroscope to a target calyx of a kidney of a patient through at least a portion of a urinary tract of the patient, determining a positional offset between one or more position sensors associated with the ureteroscope and a target papilla of the kidney that is at least partially exposed within the target calyx, and determining a percutaneous access target based at least in part on one or more of a present position of the one or more position sensors and the offset.

The method can further comprise advancing a percutaneous access instrument to the target calyx by targeting the percutaneous access target. In some embodiments, the method further comprises contacting the target papilla with the ureteroscope, recording a position of the ureteroscope associated with said contacting, retracting the ureteroscope away from the target papilla, and parking the ureteroscope at an offset position associated with the positional offset. The positional offset can indicate, for example, at least five degrees of freedom.

In some implementations, the present disclosure relates to a method of positioning a surgical instrument. The method comprises advancing a medical instrument to a treatment site of a patient, the medical instrument comprising a camera, generating real-time video of the treatment site using the camera of the medical instrument, displaying a user interface including the real-time video in a window of the user interface, and projecting an anatomical feature targeting icon at a center of the window of the user interface.

The targeting icon can include any type of form or shape, or combination thereof, including crosshairs. The method can further comprise manipulating the medical instrument to center the targeting icon over a representation of a target anatomical feature in the real-time video. For example, the method may comprise projecting one or more bounding features in the window of the user interface about the center of the window, wherein the one or more bounding features have a size that is independent of a position of the medical instrument. In some embodiments, the method further comprises manipulating the medical instrument to fit the representation of the target anatomical feature within the one or more bounding features. Manipulating the medical instrument to fit the representation of the target anatomical feature within the one or more bounding features can involve retracting the medical instrument away from the target anatomical feature such that the representation of the target anatomical feature shrinks in the window of the user interface. In some embodiments, the one or more bounding features have an at least partial box form.

The method can further comprise receiving sensor data indicating a three-dimensional position of a percutaneous access needle within an electromagnetic field, determining a position of a distal end of the needle relative to the camera based at least in part on the sensor data, and displaying a needle-projection icon in the window of the user interface that indicates a position of the distal end of the needle relative to the real-time video. Some embodiments involve the presentation of one or more icons representing a projected needle entry point into the target anatomical feature (e.g., papilla). For example, the indicator(s) can represent the location of the needle to provide situational awareness and/or information about the needle trajectory by displaying where the needle will enter from. The needle-projection/trajectory indicator(s) can display the needle orientation as a line-type form/shape. For example, one or both of the proximal and distal points of the needle can be projected and/or connected with a line-type representation.

The method can further comprise determining that the position of the distal end of the needle is outside of the window of the user interface, wherein the needle-projection icon indicates a direction of the position of the distal end of the needle relative to the window. In some embodiments, the method further comprises manipulating the medical instrument to center the needle-projection icon in the window of the user interface. In some embodiments, the method further comprises calibrating a sensor associated with the needle in an image space of the camera. The method can comprise modifying a form of the needle-projection icon in response to approximation of the distal end of the needle to the medical instrument.

The size of the needle-projection icon can be changed/modified based on a determined needle projection/prediction accuracy. In cases where there is substantial anatomical motion, which may result in needle-projection error, the needle-projection icon can be presented with a relatively larger size to represent a relatively larger determined error with respect to the needle projection/trajectory. In some embodiments, a form of the needle-projection icon indicates a distance of the distal end of the needle from the medical instrument.

In some implementations, the present disclosure relates to a method of targeting an anatomical feature. The method comprises advancing an endoscope into a target anatomical lumen of a patient, the endoscope comprising a position sensor associated with a distal end portion of the endoscope, recording position data associated with a plurality of positions of the endoscope within the target anatomical lumen using the position sensor, estimating a surface of the target anatomical lumen based at least in part on the position data, and determining an axis of the target anatomical lumen based at least in part on the estimated surface of the target anatomical lumen.

The method can further comprise targeting the target anatomical lumen with a percutaneous access needle based at least in part on the determined axis of the target anatomical lumen. For example, targeting the target anatomical lumen can involve advancing a percutaneous access needle along a path that is substantially parallel to the determines axis of the target anatomical lumen. In some embodiments, the position sensor is an electromagnetic sensor device, and recording the position data is performed using an electromagnetic field generator disposed at least partially external to the patient.

In some embodiments, estimating the surface of the target anatomical lumen can involve interpolating the position data. Determining the axis of the target anatomical lumen can involve determining a plurality of surface normal vectors associated with the estimated surface of the target anatomical lumen. For example, the method can comprise averaging the plurality of surface normal vectors. In some embodiments, determining the axis of the target anatomical lumen is based at least in part on one or more of a map of the target anatomical lumen and a trajectory of the endoscope.

In some implementations, the present disclosure relates to a medical system comprising an endoscope configured to access a target anatomical lumen of a patient, the endoscope having a camera and an electromagnetic position sensor associated with a distal end thereof, a communication interface configured to receive video data from the endoscope, an electronic display device, and control circuitry communicatively coupled to the communication interface and the electronic display device. The control circuitry is configured to receive, from the endoscope of the communication interface, real-time video data of a treatment site internal to the patient, cause a user interface to be displayed on the electronic display, the user interface including the real-time video in a window of the user interface, and cause an anatomical feature targeting icon to be displayed at a center of the window of the user interface. The targeting icon can include, for example, crosshairs and/or the like.

The control circuitry can be further configured to cause one or more bounding features to be displayed in the window of the user interface about the center of the window. A size of the one or more bounding features relative to a representation of a target anatomical feature in the real-time video can be based on a distance of the target anatomical feature from the camera of the endoscope. In some embodiments, the one or more bounding features have an at least partial box form.

The control circuitry can be further configured to receive sensor data indicating a three-dimensional position of a percutaneous access needle within an electromagnetic field, determine a position of a distal end of the needle relative to the endoscope based at least in part on the sensor data, and cause a needle-projection icon to be displayed in the window of the user interface. The needle-projection icon can indicate a position of the distal end of the needle relative to the real-time video.

In some implementations, the present disclosure relates to a computing device comprising an endoscope interface and control circuitry comprising one or more processors and one or more data storage devices. The control circuitry is configured to receive position data from an endoscope disposed within a target anatomical lumen of a patient, the position data indicating a plurality of positions of a position sensor associated with a distal end portion of the endoscope. As with all other description herein of positions and position sensors herein, such positions can include position and orientation aspects/information. The control circuitry is further configured to estimate a surface of the target anatomical lumen based at least in part on the position data and determine an axis of the target anatomical lumen based at least in part on the estimated surface of the target anatomical lumen.

In some embodiments, the control circuitry is configured to estimate the surface of the target anatomical lumen at least in part by interpolating the position data. In some embodiments, the control circuitry is configured to determine the axis of the target anatomical lumen at least in part by determining a plurality of surface normal vectors associated with the estimated surface of the target anatomical lumen.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIGS. 5-1 and 5-2 provide a flow diagram illustrating a process for performing guided percutaneous nephrolithotomy in accordance with one or more embodiments.

FIGS. 6-1 and 6-2 show certain images corresponding to various blocks, states, and/or operations associated with the process of FIGS. 5-1 and 5-2, respectively, in accordance with one or more embodiments.

FIGS. 14-1 and 14-2 illustrate configurations of a scope camera view/window including one or more needle-trajectory features in accordance with one or more embodiments.

DETAILED DESCRIPTION

Figure 1:
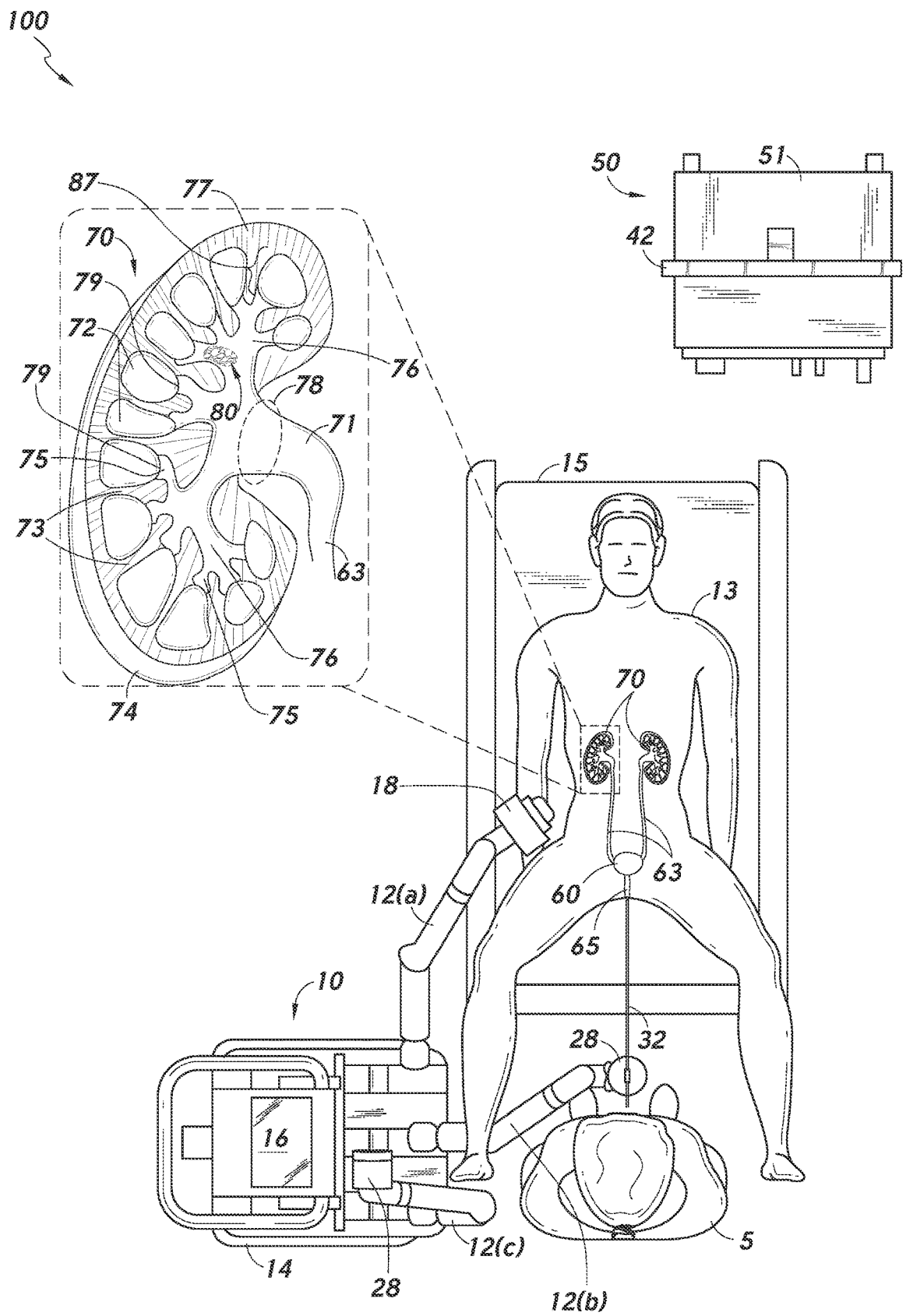
FIG. 1 illustrates an embodiment of a robotic medical system in accordance with one or more embodiments.

The headings provided herein are for convenience only and do not necessarily affect the scope or meaning of the claimed invention. Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Overview

The present disclosure relates to systems, devices, and methods for localizing and targeting target anatomical features of a patient to aid in certain medical procedures. Although certain aspects of the present disclosure are described in detail herein in the context of renal, urological, and/or nephrological procedures, such as kidney stone removal/treatment procedures, it should be understood that such context is provided for convenience and clarity, and anatomical feature localizing and targeting concepts disclosed herein are applicable to any suitable medical procedures. However, as mentioned, description of the renal/urinary anatomy and associated medical issues and procedures is presented below to aid in the description of the inventive concepts disclosed herein.

Kidney stone disease, also known as urolithiasis, is a relatively common medical condition involves the formation in the urinary tract of a solid piece of material, referred to as "kidney stones," "urinary stones," "renal calculi," "renal lithiasis," or "nephrolithiasis." Urinary stones may be formed and/or found in the kidneys, the ureters, and the bladder (referred to as "bladder stones"). Such urinary stones form as a result of concentrated minerals and can cause significant abdominal pain once they reach a size sufficient to impede urine flow through the ureter or urethra. Urinary stones may be formed from calcium, magnesium, ammonia, ur acid, cysteine, and/or other compounds.

To remove urinary stones from the bladder and ureter, surgeons may insert a ureteroscope into the urinary tract through the urethra. Typically, a ureteroscope includes an endoscope at its distal end configured to enable visualization of the urinary tract. The ureteroscope can also include a lithotomy mechanism to capture or break apart urinary stones. During a ureteroscopy procedure, one physician/technician may control the position of the ureteroscope, while another other physician/technician may control the lithotomy mechanism(s).

In order to remove relatively large stones from the kidneys (i.e., "kidney stones"), physicians may use a percutaneous nephrolithotomy ("PCNL") technique that involves inserting a nephroscope through the skin (i.e., percutaneously) to break up and/or remove the stone(s). In some implementations, locating the kidney stone(s) may be achieved using fluoroscopy to provide a target for insertion of the nephroscope. However, fluoroscopy generally increases the cost of the nephrolithotomy procedure due to the cost of the fluoroscope itself as well as the cost of a technician to operate the fluoroscope. Fluoroscopy also exposes the patient to radiation for a relatively prolonged period of time. Even with fluoroscopy, accurately making a percutaneous incision to access the kidney stone(s) can be difficult and undesirably imprecise. Furthermore, some nephrolithotomy techniques involve a two-day or three-day inpatient stay. In sum, certain nephrolithotomy solutions can be relatively costly and problematic for patients.

According to certain surgical procedures in accordance with aspects of the present disclosure, endoscopes (e.g., ureteroscopes) can be equipped with one or more position sensors, wherein the position of the sensor(s) is used as a target for percutaneous access, such as for PCNL. For example, an electromagnetic-sensor-equipped ureteroscope and/or an electromagnetic-sensor-equipped percutaneous access needle may be used to guide the percutaneous renal access for kidney stone removal and/or the like. In such procedures, the surgeon/physician can drive the ureteroscope to a target calyx of the kidney and use an electromagnetic sensor (e.g., beacon) associated with a distal end/tip of the ureteroscope as the percutaneous access target for the needle. Generally, the efficacy of percutaneous axis to a target calyx can depend at least in part on where the physician positions/parks the ureteroscope with respect to, for example, the position and/or heading of the target calyx and/or papilla through which percutaneous access may be made to the target calyx. For some procedures in which the distal end/tip of the ureteroscope is used as the percutaneous access target, it may be desirable for the distal tip of the ureteroscope to be as close as possible to the papilla/calyx interface during percutaneous access/approximation.

The terms "scope" and "endoscope" are used herein according to their broad and ordinary meanings, and may refer to any type of elongate medical instrument having image generating, viewing, and/or capturing functionality and configured to be introduced into any type of organ, cavity, lumen, chamber, or space of a body. For example, references herein to scopes or endoscopes may refer to a ureteroscope, cystoscope, nephroscope, bronchoscope, arthroscope, colonoscope, laparoscope, borescope, or the like. Scopes/endoscopes, in some instances, may comprise a rigid or flexible tube, and may be dimensioned to be passed within an outer sheath, catheter, introducer, or other lumen-type device, or may be used without such devices.

Robotic-assisted percutaneous procedures can be implemented in connection with various medical procedures, such as kidney stone removal procedures, wherein robotic tools can enable a physician/urologist to perform endoscopic (e.g., ureteroscopy) target access as well as percutaneous access/treatment. Advantageously, aspects of the present disclosure relate to real-time target tracking/localization in medical procedures, which may be utilized by the operating physician to direct a percutaneous-access instrument (e.g., needle or other rigid tool) and/or to guide robotic instrumentation, such as by adjusting endoscope position and/or alignment automatically in response to such real-time target-tracking information. To facilitate such functionality, embodiments of the present disclosure may advantageously provide mechanisms for anatomical feature target localizing, tracking, and/or three-dimensional position estimation to assist physicians (e.g., urologists) to achieve relatively efficient and accurate percutaneous access for various surgical operations, such as nephroscopy. Although aspects of the present disclosure are described herein for convenience in the context of ureteroscope-guided nephroscopy, it should be understood that inventive aspects of the present disclosure may be implemented in any suitable or desirable type of percutaneous and/or endoscopic medical procedure, whether robotic or not.

Medical System

FIG. 1 illustrates an example medical system 100 for performing various medical procedures in accordance with aspects of the present disclosure. The medical system 10 may be used for, for example, ureteroscopic procedures. As referenced and described above, certain ureteroscopic procedures involve the investigation of abnormalities of the ureter and/or the treatment/removal of kidney stones. In some implementations, kidney stone treatment can benefit from the assistance of certain robotic technologies/devices, such as may be similar to those shown in FIG. 1 and described in detail below. Robotic medical solutions can provide relatively higher precision, superior control, and/or superior hand-eye coordination with respect to certain instruments. For example, robotic-assisted percutaneous access to the kidney in accordance with some procedures can advantageously enable a urologist to perform both operating target endoscopic access and percutaneous access. However, according to some solutions, percutaneous kidney access can suffer from certain difficulties with respect to the proper alignment/positioning of a target ureteroscope and/or determining a target percutaneous access path that is substantially in-line with the target infundibula, calyx, and/or papilla. In some implementations, the present disclosure relates to systems (e.g., system 100), devices, and methods for providing intelligent guidance for ureteroscopes and/or percutaneous access instruments (e.g., needles). For example, embodiments the present disclosure relate to systems, devices, and methods incorporating certain automatic target localization, tracking, and/or 3D physician estimation functionality, which may advantageously assist urologists or other technicians in achieving efficient and accurate percutaneous access to the kidney. Although embodiments of the present disclosure are presented in the context of ureteroscopes and/or human renal anatomy, it should be understood that the principles disclosed herein may be implemented in any type of endoscopic procedure.

The medical system 100 includes a robotic system 10 configured to engage with and/or control a medical instrument 32 (e.g., ureteroscope) to perform a procedure on a patient 13. The medical system 10 also includes a control system 50 configured to interface with the robotic system 10, provide information regarding the procedure, and/or perform a variety of other operations. For example, the control system 50 can include one or more display(s) 42 configured to present certain information to assist the physician 5 and/or other technician(s) or individual(s). The medical system 10 can include a table 15 configured to hold the patient 13. The system 10 may further include an electromagnetic (EM) field generator 18, which may be held by one or more of the robotic arms 12 of the robotic system 10, or may be a stand-alone device.

In some implementations, the system 10 may be used to perform a percutaneous procedure, such as percutaneous nephrolithotomy (PCNL). To illustrate, if the patient 13 has a kidney stone 80 that is too large to be removed/passed through the urinary tract (60, 63, 65), the physician 5 can perform a procedure to remove the kidney stone 80 through a percutaneous access point/path associated with the flank/side of the patient 13. In some embodiments, the physician 5 can interact with the control system 50 and/or the robotic system 10 to cause/control the robotic system 10 to advance and navigate the medical instrument 32 (e.g., a scope) from the urethra 65, through the bladder 60, up the ureter 63, and into the calyx network of the kidney 70 where the stone 80 is located. The control system 50 can provide information via the display(s) 42 associated with the medical instrument 32, such as real-time endoscopic images captured therewith, to assist the physician 5 in navigating/controlling the medical instrument.

The renal anatomy is described herein for reference with respect to certain medical procedures relating to aspects of the present inventive concepts. The kidneys 70, shown roughly in typical anatomical position in FIG. 1, generally comprise two bean-shaped organs located on the left and right sides, respectively, in the retroperitoneal space. In adult humans, the kidneys are generally about 11 cm in height/length. The kidneys receive blood from the paired renal arteries; blood exits the kidney via the paired renal veins, neither of which is shown in FIG. 1 for visual clarity. Each kidney 70 is fluidly coupled with a ureter 63, which generally comprises a tube that carries excreted urine from the kidney 70 to the bladder 60.

The kidneys 70 are typically located relatively high in the abdominal cavity and lie in a retroperitoneal position at a slightly oblique angle. The asymmetry within the abdominal cavity, generally caused by the position of the liver, results in the right kidney (shown in detail in FIG. 1) typically being slightly lower and smaller than the left, and being placed slightly more to the middle than the left kidney. On top of each kidney is an adrenal gland (not shown). The upper parts of the kidneys are partially protected by the 11th and 12th ribs. Each kidney, with its adrenal gland, is generally surrounded by two layers of fat: the perirenal fat present between renal fascia and renal capsule and pararenal fat superior to the renal fascia.

The kidneys 70 participate in the control of the volume of various body fluid compartments, fluid osmolality, acid-base balance, various electrolyte concentrations, and removal of toxins. The kidneys 70 provide filtration functionality by secreting certain substances and reabsorbing others. Examples of substances secreted into the urine are hydrogen, ammonium, potassium and uric acid. In addition, the kidneys also carry out various other functions, such as hormone synthesis, and others.

A recessed area on the concave border of the kidney 70 is the renal hilum 78, where the renal artery (not shown) enters the kidney 70 and the renal vein (not shown) and ureter 63 leave. The kidney 70 is surrounded by tough fibrous tissue, the renal capsule 74, which is itself surrounded by perirenal fat, renal fascia, and pararenal fat. The anterior (front) surface of these tissues is the peritoneum, while the posterior (rear) surface is the transversalis fascia.

The functional substance, or parenchyma, of the kidney 70 is divided into two major structures: the outer renal cortex 77 and the inner renal medulla 87. These structures take the shape of a plurality of generally cone-shaped renal lobes, each containing renal cortex surrounding a portion of medulla called a renal pyramid 72. Between the renal pyramids 72 are projections of cortex called renal columns 73. Nephrons (not shown in detail in FIG. 1), the urine-producing functional structures of the kidney, span the cortex 77 and medulla 87. The initial filtering portion of a nephron is the renal corpuscle, which is located in the cortex and is followed by a renal tubule that passes from the cortex deep into the medullary pyramids. Part of the renal cortex, a medullary ray, is a collection of renal tubules that drain into a single collecting duct.

The tip/apex, or papilla 79, of each pyramid empties urine into a respective minor calyx 75; minor calyces 75 empty into major calyces 76, and major calyces 76 empty into the renal pelvis 71, which transitions to the ureter 63. At the hilum 78, the ureter 63 and renal vein exit the kidney and the renal artery enters. Hilar fat and lymphatic tissue with lymph nodes surrounds these structures. The hilar fat is contiguous with a fat-filled cavity called the renal sinus. The renal sinus collectively contains the renal pelvis 71 and calyces 75, 76 and separates these structures from the renal medullary tissue. The funnel/tubular-shaped anatomy associated with the calyces can be referred to as the infundibulum/infundibula. That is, an infundibulum generally leads to the termination of a calyx where a papilla is exposed within the calyx.

With further reference to the medical system 10, the medical instrument (e.g., scope) 32 can be advanced into the kidney 70 through the urinary tract. Once at the site of the kidney stone 80 (e.g., within a target calyx 75 of the kidney 70 through which the stone 80 is accessible), the medical instrument 32 can be used to designate/tag a target location for percutaneous access to the kidney 70. To minimize damage to the kidney and/or surrounding anatomy, the physician 5 can designate a particular papilla 79 of the kidney 70 as the target location/anatomical feature for entering into the kidney 70 with a percutaneous-access instrument (e.g., needle; not shown, see, e.g., FIG. 13). However, other target locations can be designated or determined. Once the percutaneous-access instrument has reached the target location (e.g., calyx 75), the utilized percutaneous access path may be used to extract the kidney stone 80 from the patient 13. The term "percutaneous access instrument" is used herein according to its broad and ordinary meaning and may refer to a surgical tool or device that is configured to puncture or to be inserted through human skin and/or other tissue/anatomy, such as a needle, a scalpel, a guidewire, and the like. However, it should be understood that a percutaneous access instrument can refer to other types of medical instruments in the context of the present disclosure.

In the example of FIG. 1, the medical instrument 32 is implemented as a scope. However, the medical instrument 32 can each be implemented as any suitable type of medical instrument, such as a catheter, a guidewire, a lithotripter, a basket retrieval device, and so on. In some embodiments, the medical instrument 32 is a steerable device.

A scope, such as the scope 32 of the system 100, can be configured to navigate within the human anatomy, such as within a natural orifice or lumen of the human anatomy. A scope can include, for example, a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), and so on.

Figure 2:
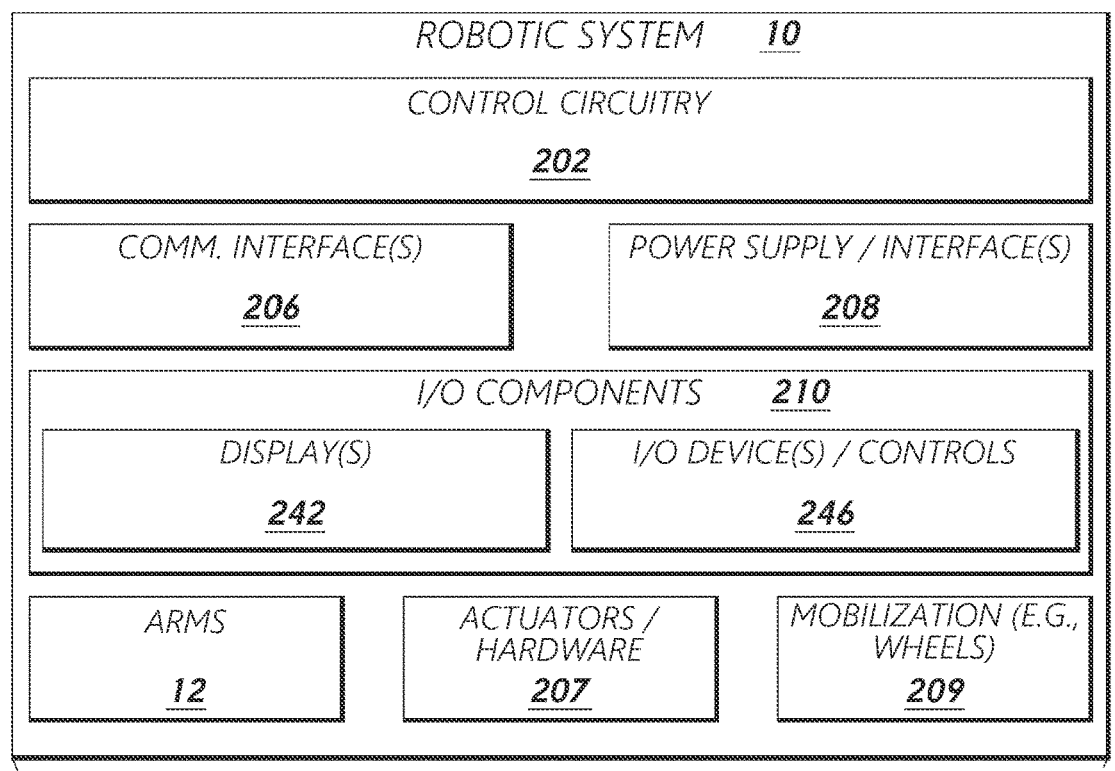
FIG. 2 illustrates an example robotic system that may be implemented in the medical system of FIG. 1 in accordance with one or more embodiments.
Figure 2:
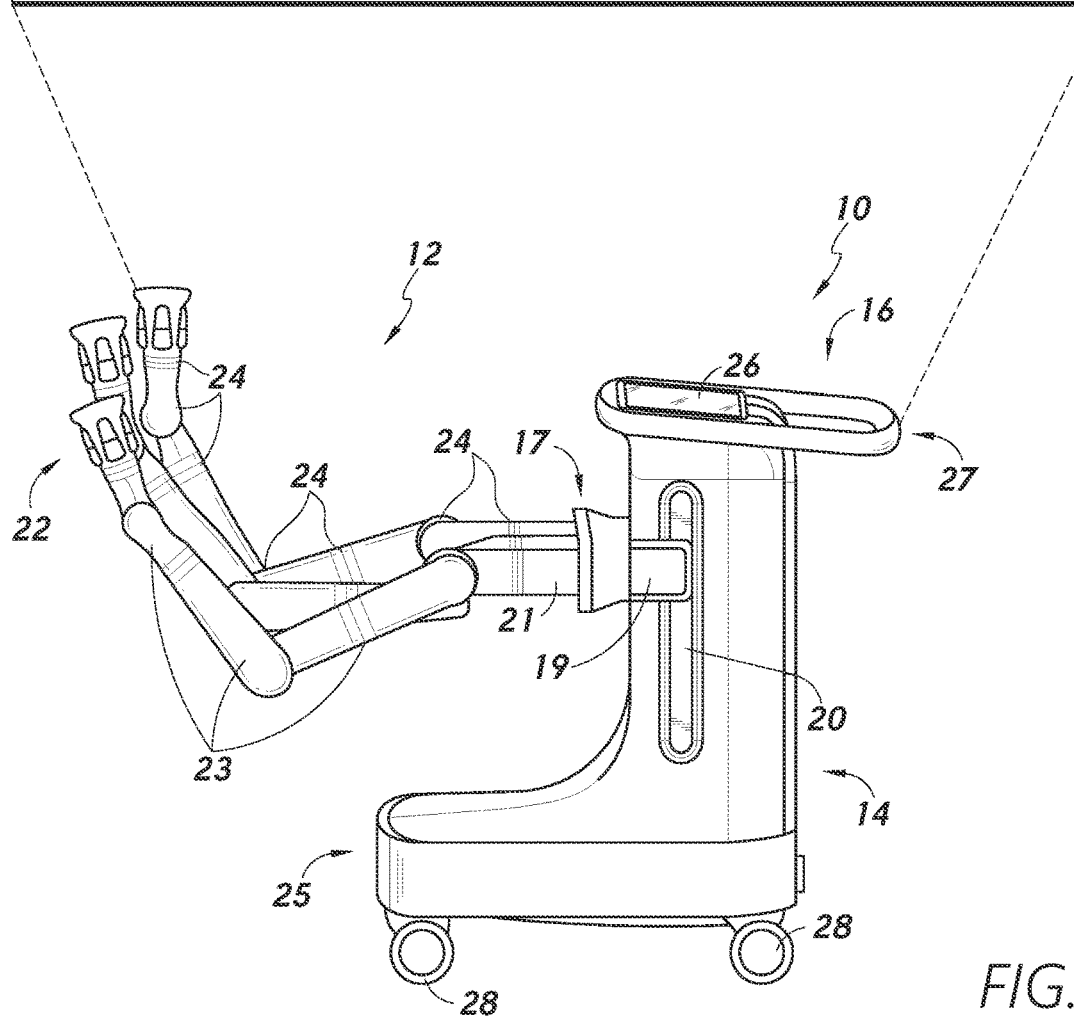

With reference to FIG. 1 and FIG. 2, which shows an example embodiment of the robotic system 10 of FIG. 1 in accordance with one or more embodiments of the present disclosure, the robotic system 10 can be configured to at least partly facilitate execution of a medical procedure. The robotic system 10 can be arranged in a variety of ways depending on the particular procedure. The robotic system 10 can include one or more robotic arms 12 configured to engage with and/or control, for example, the scope 32 (and/or a percutaneous access instrument; not shown) to perform one or more aspects of a procedure. As shown, each robotic arm 12 can include multiple arm segments 23 coupled to joints, which can provide multiple degrees of movement/freedom. In the example of FIG. 1, the robotic system 10 is positioned proximate to the patient's legs and the robotic arms 12 are actuated to engage with and position the scope 32 for access into an access point, such as the urethra 65 of the patient 13. When the robotic system 100 is properly positioned, the scope 32 can be inserted into the patient 13 robotically using the robotic arms 12, manually by the physician 5, or a combination thereof.

The robotic system 10 can be coupled to any component of the medical system 100, such as to the control system 50, the table 15, the EM field generator 18, the scope 32, and/or a percutaneous-access instrument (e.g., needle; see, e.g., FIG. 12). In some embodiments, the robotic system 10 is communicatively coupled to the control system 50. For example, the robotic system 10 may be configured to receive a control signal from the control system 50 to perform an operation, such as to position one or more of the robotic arms 12 in a particular manner, manipulate the scope 32, and so on. In response, the robotic system 10 can control, using certain control circuitry 202, actuators 207, and/or other components of the robotic system 10, a component of the robotic system 10 to perform the operation. In some embodiments, the robotic system 10 is configured to receive images and/or image data from the scope 32 representing internal anatomy of the patient 13, namely the urinary system with respect to the particular depiction of FIG. 1, and/or send images/image data to the control system 50 (which can then be displayed on the display 42 or other output device). Furthermore, in some embodiments, the robotic system 10 is coupled to a component of the medical system 10, such as the control system 50, in such a manner as to allow for fluids, optics, power, or the like to be received therefrom. The robotic system 10 can include one or more communication interfaces 206, power suppl(ies)/interface(s), electronic display(s) 242, and/or other input/output component(s) 210.

Figure 3:
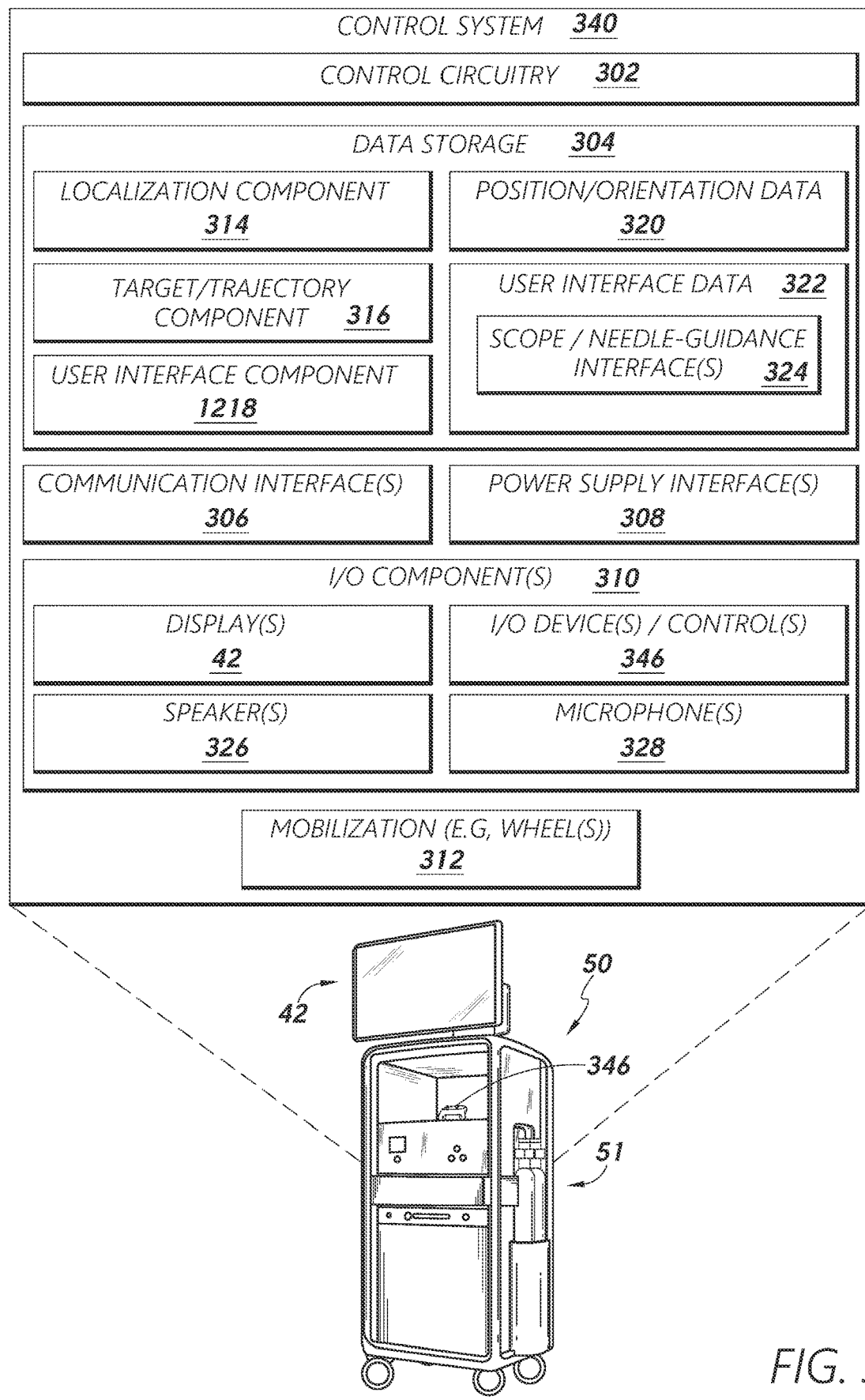
FIG. 3 illustrates an example control system that may be implemented in the medical system of FIG. 1 in accordance with one or more embodiments.

With reference to FIG. 1 and FIG. 3, which shows an example embodiment of the control system 50 of FIG. 1 in accordance with one or more embodiments of the present disclosure, the control system 50 can be configured to provide various functionality to assist in performing a medical procedure. In some embodiments, the control system 50 can be coupled to the robotic system 10 and operate in cooperation with the robotic system 10 to perform a medical procedure on the patient 13. For example, the control system 50 can communicate with the robotic system 10 via a wireless or wired connection (e.g., to control the robotic system 10 and/or the scope 32, receive images captured by the scope 32, etc.), provide fluids to the robotic system 10 via one or more fluid channels, provide power to the robotic system 10 via one or more electrical connections, provide optics to the robotic system 10 via one or more optical fibers or other components, and so on. Further, in some embodiments, the control system 50 can communicate with a needle and/or nephroscope to receive position data therefrom. Moreover, in some embodiments, the control system 50 can communicate with the table 15 to position the table 15 in a particular orientation or otherwise control the table 15. Further, in some embodiments, the control system 50 can communicate with the EM field generator 18 to control generation of an EM field in an area around the patient 13.

The system 10 can include certain control circuitry configured to perform certain of the functionality described herein, including the control circuitry 202 of the robotic system 10 and/or the control circuitry 302 of the control system 50. That is, the control circuitry of the system 10 may be part of the robotic system 10, the control system 50, or both. Therefore, any reference herein to control circuitry may refer to circuitry embodied in a robotic system, a control system, or any other component of a medical system, such as the medical system 100 shown in FIG. 1. The term "control circuitry" is used herein according to its broad and ordinary meaning, and may refer to any collection of processors, processing circuitry, processing modules/units, chips, dies (e.g., semiconductor dies including come or more active and/or passive devices and/or connectivity circuitry), microprocessors, micro-controllers, digital signal processors, microcomputers, central processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry referenced herein may further include one or more circuit substrates (e.g., printed circuit boards), conductive traces and vias, and/or mounting pads, connectors, and/or components. Control circuitry referenced herein may further comprise one or more, storage devices, which may be embodied in a single memory device, a plurality of memory devices, and/or embedded circuitry of a device. Such data storage may comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware and/or software state machine, analog circuitry, digital circuitry, and/or logic circuitry, data storage device(s)/register(s) storing any associated operational instructions may be embedded within, or external to, the circuitry comprising the state machine, analog circuitry, digital circuitry, and/or logic circuitry.

The control circuitry 202 and/or 302 may comprise a computer-readable medium storing, and/or configured to store, hard-coded and/or operational instructions corresponding to at least some of the steps and/or functions illustrated in one or more of the present figures and/or described herein. Such computer-readable medium can be included in an article of manufacture in some instances. The control circuitry 202/302 may be entirely locally maintained/disposed or may be remotely located at least in part (e.g., communicatively coupled indirectly via a local area network and/or a wide area network).

With respect to the robotic system 10, at least a portion of the control circuitry 202 may be integrated with the base 25, column 14, and/or console 16 of the robotic system 10, and/or another system communicatively coupled to the robotic system 10. With respect to the control system 50, at least a portion of the control circuitry 302 may be integrated with the console base 51 and/or display unit 42 of the control system 50. It should be understood that any description of functional control circuitry or associated functionality herein may be understood to be embodied in either the robotic system 10, the control system 50, or both, and/or at least in part in one or more other local or remote systems/devices.

With reference to FIG. 2, the robotic system 10 generally includes an elongated support structure 14 (also referred to as a "column"), a robotic system base 25, and a console 16 at the top of the column 14. The column 14 may include one or more arm supports 17 (also referred to as a "carriage") for supporting the deployment of one or more robotic arms 12 (three shown in FIG. 2). The arm support 17 may include individually-configurable arm mounts that rotate along a perpendicular axis to adjust the base of the robotic arms 12 for better positioning relative to the patient. The arm support 17 also includes a column interface 19 that allows the arm support 17 to vertically translate along the column 14.

In some embodiments, the column interface 19 can be connected to the column 14 through slots, such as slot 20, that are positioned on opposite sides of the column 14 to guide the vertical translation of the arm support 17. The slot 20 contains a vertical translation interface to position and hold the arm support 17 at various vertical heights relative to the robotic system base 25. Vertical translation of the arm support 17 allows the robotic system 10 to adjust the reach of the robotic arms 12 to meet a variety of table heights, patient sizes, and physician preferences. Similarly, the individually-configurable arm mounts on the arm support 17 can allow the robotic arm base 21 of robotic arms 12 to be angled in a variety of configurations.

The robotic arms 12 may generally comprise robotic arm bases 21 and end effectors 22, separated by a series of linkages 23 that are connected by a series of joints 24, each joint comprising one or more independent actuators 207. Each actuator may comprise an independently-controllable motor. Each independently-controllable joint 24 can provide or represent an independent degree of freedom available to the robotic arm. In some embodiments, each of the arms 12 has seven joints, and thus provides seven degrees of freedom, including "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The robotic system base 25 balances the weight of the column 14, arm support 17, and arms 12 over the floor. Accordingly, the robotic system base 25 may house heavier components, such as electronics, motors, power supply, as well as components that selectively enable movement or immobilize the robotic system. For example, the robotic system base 25 includes wheel-shaped casters 28 that allow for the robotic system to easily move around the room prior to a procedure. After reaching the appropriate position, the casters 28 may be immobilized using wheel locks to hold the robotic system 10 in place during the procedure.

Positioned at the upper end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite arm support 17. From this position, the physician may view the console 16, robotic arms 12, and patient while operating the console 16 from behind the robotic system 10. As shown, the console 16 can also include a handle 27 to assist with maneuvering and stabilizing robotic system 10.

The end effector 22 of each of the robotic arms 12 may comprise an instrument device manipulator (IDM), which may be attached using a mechanism changer interface (MCI). In some embodiments, the IDM can be removed and replaced with a different type of IDM, for example, a first type of IDM may manipulate an endoscope, while a second type of IDM may manipulate a laparoscope. The MCI can include connectors to transfer pneumatic pressure, electrical power, electrical signals, and/or optical signals from the robotic arm 12 to the IDM. The IDMs may be configured to manipulate medical instruments (e.g., surgical tools/instruments), such as the scope 32 using techniques including, for example, direct drive, harmonic drive, geared drives, belts and pulleys, magnetic drives, and the like.

With reference to FIG. 3, the control system 50 can include various I/O components 310 configured to assist the physician 5 or others in performing a medical procedure. For example, the input/output (I/O) components 310 can be configured to allow for user input to control the scope 32, such as to navigate the scope 32 within the patient 13. In some embodiments, for example, the physician 5 can provide input to the control system 50 and/or robotic system 10, wherein in response to such input, control signals can be sent to the robotic system 10 to manipulate the scope 32. As also shown in FIG. 1, the control system 50 can include one or more display devices 42 to provide various information regarding a procedure. For example, the display(s) 42 can provide information regarding the scope 32. For example, the control system 50 can receive real-time images that are captured by the scope 32 and display the real-time images via the display(s) 42. Additionally or alternatively, the control system 50 can receive signals (e.g., analog, digital, electrical, acoustic/sonic, pneumatic, tactile, hydraulic, etc.) from a medical monitor and/or a sensor associated with the patient 13, and the display(s) 42 can present information regarding the health or environment of the patient 13. Such information can include information that is displayed via a medical monitor including, for example, information relating to heart rate (e.g., ECG, HRV, etc.), blood pressure/rate, muscle bio-signals (e.g., EMG), body temperature, blood oxygen saturation (e.g., $SpO_2$), $CO_2$, brainwaves (e.g., EEG), environmental and/or local or core body temperature, and so on.

To facilitate the functionality of the control system 50, the control system can include various components (sometimes referred to as "subsystems"). For example, the control system 50 can include the control electronics/circuitry 302, as well as one or more power supplies/interfaces 308, pneumatic devices, optical sources, actuators, data storage devices 304, and/or communication interfaces 306. In some embodiments, the control system 50 includes control circuitry comprising a computer-based control system that is configured to store executable instructions, that when executed, cause various operations to be implemented relating to the functionality described herein. In some embodiments, the control system 50 is movable, while in other embodiments, the control system 50 is a substantially stationary system. Although various functionality and components are discussed as being implemented by the control system 50, any of such functionality and/or components can be integrated into and/or performed by other systems and/or devices, such as the robotic system 10, the table 15, or others, for example.

With further reference to FIG. 1, the medical system 10 can provide a variety of benefits, such as providing guidance to assist a physician in performing a procedure (e.g., instrument tracking, instrument alignment information, etc.), enabling a physician to perform a procedure from an ergonomic position without the need for awkward arm motions and/or positions, enabling a single physician to perform a procedure with one or more medical instruments, avoiding radiation exposure (e.g., associated with fluoroscopy techniques), enabling a procedure to be performed in a single-operative setting, providing continuous suction to remove an object more efficiently (e.g., to remove a kidney stone), and so on. For example, the medical system 100 can provide guidance information to assist a physician in using various medical instruments to access a target anatomical feature while minimizing bleeding and/or damage to anatomy (e.g., critical organs, blood vessels, etc.). Further, the medical system 100 can provide non-radiation-based navigational and/or localization techniques to reduce physician and patient exposure to radiation and/or reduce the amount of equipment in the operating room. Moreover, the medical system 100 can provide functionality that is distributed between at least the control system 50 and the robotic system 10, which may be independently movable. Such distribution of functionality and/or mobility can enable the control system 50 and/or the robotic system 10 to be placed at locations that are optimal for a particular medical procedure, which can maximize working area around the patient and/or provide an optimized location for a physician to perform a procedure.

The various components of the system 100 can be communicatively coupled to each other over a network, which can include a wireless and/or wired network. Example networks include one or more personal area networks (PANs), local area networks (LANs), wide area networks (WANs), Internet area networks (IANs), cellular networks, the Internet, etc. Furthermore, in some embodiments, the various components of the system 10 can be connected for data communication, fluid/gas exchange, power exchange, and so on via one or more support cables, tubes, or the like.

The robotic system 10 and/or the control system 50 includes certain user controls 246, 346, which may comprise any type of user input (and/or output) devices or device interfaces, such as one or more buttons, keys, joysticks, handheld controllers (e.g., video-game-type controllers), computer mice, trackpads, trackballs, control pads, and/or sensors (e.g., motion sensors or cameras) that capture hand gestures and finger gestures, touchscreens, and/or interfaces/connectors therefore. The user controls 246, 346 are communicatively and/or physically coupled to at least some of the control circuitry 202, 302, respectively.

In some embodiments, the user controls 246, 346 and/or associated control circuitry are configured to receive user input to allow a user to control a medical instrument, such as an instrument manipulatable at least in part by a robotic system (e.g., endoscope or nephroscope) to control pitch and yaw motion of a distal end of the instrument using the controls. For example, movement on a joystick may be mapped to yaw and pitch movement in the distal end of the scope/device. In some embodiments, user controls are configured to provide haptic feedback to the user. For example, a joystick or other control mechanism may vibrate to indicate an invalid or potentially problematic input. In some embodiments, the control system 50 and/or robotic system 10 can also provide visual feedback (e.g., pop-up messages) and/or audio feedback (e.g., beeping) to indicate issues associated with robotic operation.

In some implementations, the control circuitry 202/302 may use a three-dimensional (3D) map of patient anatomy and/or pre-determined computer models of the patient to control a medical instrument (e.g., endoscope). For example, the control circuitry 202 can be configured to provide control signals to the robotic arms 12 of the robotic system 10 to manipulate the relevant instrument to position the same at a target location, position, and/or orientation/alignment. For embodiments implementing 3D mapping, position control mode may require sufficiently accurate mapping of the anatomy of the patient.

In some embodiments, a user can manually manipulate a robotic arm 12 of the robotic system 10 without using electronic user controls. For example, during setup in a surgical operating room, a user may move the robotic arms 12 and/or any other medical instruments to provide desired access to a patient. The robotic system 10 may rely on force feedback and inertia control from the user to determine appropriate configuration of the robotic arms 12 and associated instrumentation.

The display device(s) 42 of the control system 50 may be integrated with the user controls 346, for example, as a tablet device with a touchscreen providing for user input. The display device(s) 42 can be configured to provide data and input commands to the robotic system 10 using integrated display touch controls. The display device(s) 42 can be configured to display graphical user interfaces showing information about the position and orientation of various instruments operating within the patient and/or system based on information provided by one or more position sensors. In some embodiments, position sensors associated with medical instruments (e.g., an endoscope) may be configured to generate signals indicative of position and transmit the same on wires and/or transmitters coupled to the sensors. Such connectivity components may be configured to transmit the position information to the console base 51 for processing thereof by the control circuitry 302 and for presentation via the display device(s).

In the example of FIG. 3, the control system 50 is illustrated as a cart-based system that is movable with the one or more wheels 312. However, the control system 50 can be implemented as a stationary system, integrated into another system/device, and so on. Although certain components of the control system 50 are illustrated in FIG. 3, it should be understood that additional components not shown can be included in embodiments in accordance with the present disclosure. Furthermore, certain of the illustrated components can be omitted in some embodiments. Although the control circuitry 302 is illustrated as a separate component in the diagram of FIG. 3, it should be understood that any or all of the remaining components of the control system 50 can be embodied at least in part in the control circuitry 302.

The localization component 314 can comprise instructions and/or control circuitry configured to cause one or more localization techniques to be performed to determine and/or track a position and/or an orientation of an object, such as a medical instrument, and/or a target anatomical feature (e.g., papilla). For example, the localization component 314 can process input data (e.g., sensor data from a medical instrument, model data regarding anatomy of a patient, position data of a patient, pre-operative data, robotic command and/or kinematics data, etc.) to generate position/orientation data 320 for one or more medical instruments. The position/orientation data 320 can indicate a location and/or an orientation of one or more medical instruments relative to a frame of reference. The frame of reference can be a frame of reference relative to anatomy of a patient, a known object (e.g., an EM field generator), a coordinate system/space, a coordinate frame defined on a robotic system/cart, and so on.

In some embodiments, the localization component 314 can process pre-operative data to determine a position and/or an orientation of an object. The pre-operative data (sometimes referred to as "mapping data") can be generated by performing computed tomography (CT) scans, such as low dose CT scans. In some embodiments, the present disclosure provides mechanisms for determining/generating mapping data based on electromagnetic field position data recorded using an endoscope electromagnetic sensor disposed within the target anatomy (e.g., calyx network of a kidney of a patient). Further, in some embodiments, the localization component 314 can direct vision-based technique(s) to determine a position and/or an orientation of a target anatomical feature. For example, a medical instrument can be equipped with a camera, a range sensor (sometimes referred to as "a depth sensor"), a radar device, etc., to provide sensor data in the form of vision data.

The localization component 314 can direct the processing of the vision data to facilitate vision-based location tracking of the medical instrument. For example, a pre-operative model data can be used in conjunction with vision data to enable computer vision-based tracking of a medical instrument (e.g., an endoscope). Moreover, in some embodiments, other types of vision-based techniques can be performed to determine a position and/or an orientation of an object. For example, the medical system 10 can be configured to track to determine motion of an image sensor (e.g., a camera or other sensor), and thus, a medical instrument associated with the image sensor. Use of mapping data can also enhance vision-based algorithms or techniques. Furthermore, the localization component 314 can direct the use of optical flow processing, another computer vision-based technique, to analyze displacement and/or translation of image pixels in a video sequence in vision data to infer camera movement. Examples of optical flow techniques can include motion detection, object segmentation calculations, luminance, motion compensated encoding, stereo disparity measurement, etc.

In some embodiments, the localization component 314 and control circuitry 302 can use electromagnetic tracking to determine a position and/or an orientation of an object. For example, the localization component 314 can use real-time EM tracking to determine a real-time location of a medical instrument in a coordinate system/space that can be registered to the patient's anatomy, which can be represented by a pre-operative model or other model. In EM tracking, an EM sensor (or tracker) including one or more sensor coils can be embedded in one or more locations and/or orientations in a medical instrument (e.g., a scope, a needle, etc.). The EM sensor can measure a variation in an EM field created by one or more static EM field generators positioned at a known location. The location information detected by the EM sensors can be stored as EM data. The localization component 314 can process the EM data to determine a position and/or orientation of an object, such as a medical instrument. An EM field generator (or transmitter) can be placed close to the patient (e.g., within a predetermined distance) to create a low intensity magnetic field that an EM sensor can detect. The magnetic field can induce small currents in the sensor coils of the EM sensor, which can be analyzed to determine a distance and/or angle between the EM sensor and the EM field generator. These distances and/or orientations can be intra-operatively "registered" to patient anatomy (e.g., a pre-operative model) in order to determine a geometric transformation that aligns a single location in a coordinate system with a position in the pre-operative model of the patient's anatomy. Once registered, an EM sensor (e.g., an embedded EM tracker) in one or more positions of a medical instrument (e.g., the distal tip of an endoscope, a needle, etc.) can provide real-time indications of a position and/or an orientation the medical instrument through the patient's anatomy.

In some embodiments, the localization component 314 and control circuitry 302 can use input data in combination. For example, the control circuitry 302 can use a probabilistic approach where a confidence weight is assigned to a position/orientation determined from multiple forms of input data. To illustrate, if EM data is not as reliable (as may be the case where there is EM interference), the EM data can be associated with a relatively low confidence value and other forms of input data can be relied on, such as vision data, robotic command and kinematics data, and so on.

The target/trajectory component 316 can be configured to determine a position of a target location within the human anatomy and/or a coordinate space/system. It should be understood that a "target," as described in the present disclosure, can also be a reference to an anatomical region/feature, such as surface of the papilla. For example, in some embodiments, both the position of the target and the uncertainty associated with the position of the target can be captured based on sources of error, such as sensor calibration. A target location can represent a point/point set within the human anatomy and/or a coordinate space/system. For example, the target/trajectory component 316 can identify one or more points for a target location within a coordinate system, identify coordinates for the one or more points (e.g., X, Y, Z coordinates for each point), and associate the coordinates with the target location. In some embodiments, the target/trajectory component 316 can use a position and/or orientation of a medical instrument to determine a position of a target location. For example, a scope can be navigated to contact or be within proximity to a target location (e.g., parked in-front of the target location).

A target location can represent a fixed or movable point(s) within the human anatomy and/or a coordinate space/system. For example, if a papilla is initially designated as a target location, coordinates for the target location can be determined and updated as the procedure proceeds and the papilla moves (e.g., due to insertion of a medical instrument). Here, a location of a scope (which can be within proximity to the papilla) can be tracked over time and used to update the coordinates of the target location. In some embodiments, the target/trajectory component 316 can estimate/determine a position of a target location (e.g., target anatomical feature).

In some embodiments, a target trajectory and/or a trajectory of a medical instrument can be defined/represented with respect to one or more anatomical planes/axes. For example, a trajectory can be defined/represented as an angle with respect to the coronal/sagittal/transverse plane(s) or another plane/axis (e.g., a 20 degree cranial-caudal angle, 10 degree medial-lateral angle, etc.). To illustrate, the control system 50 can determine a pose of a medical instrument with respect to an EM field generator and/or a location of a target with respect to the EM field generator. The control system 50 can also determine, based on robotic kinematics, a pose of the EM field generator with respect to a robotic system. In some cases, the control system 50 can infer/determine that the robotics system is parallel to the bed. Based on such information, the control system 50 can determine a target trajectory and/or a trajectory of the medical instrument within respect to an anatomical plane, such as an angle with respect to an anatomical plane for the patient on the bed.

The target/trajectory component 316 can also be configured to determine a target trajectory for a medical instrument or another object. A target trajectory can represent a desired path for accessing a target location and/or anatomical feature. A target trajectory can be determined based on a variety of information, such as a position of a medical instrument(s) (e.g., a needle, a scope, etc.), a target location within the human anatomy, a position and/or orientation of a patient, the anatomy of the patient (e.g., the location of organs within the patient relative to the target location), and so on. For example, a target trajectory can include a line that extends from a position of a medical instrument and/or a location on the skin of a patient to/through a position of a target location within the patient. In examples, a physician can analyze images or models of the human anatomy and provide input to designate a target trajectory, such as by drawing a line on an image of the internal anatomy of a patient. In some embodiments, the target/trajectory component 316 can calculate a target trajectory initially and/or update the target trajectory throughout the procedure. For example, as a target location moves during the procedure, a target trajectory can be updated due to the change in position of the target location. In examples where a target location is estimated, a target trajectory can represent an estimated path to reach the target location.

The user interface component 318 can be configured to facilitate one or more user interfaces (also referred to as "one or more graphical user interfaces (GUI)"). For example, the user interface component 318 can generate user interface data 322 representing scope- and/or needle-guidance interface(s) 324 that include one or more visualizations to indicate an orientation and/or position of a medical instrument. The user interface component 318 can use the position/orientation data 320 regarding one or more medical instruments, information regarding a target location, and/or information regarding a target trajectory to present, as represented by the interface data 322, one or more visual features/icons indicative target scope position, needle trajectory, and/or the like. Such Further, such icons/features can be presented/represented relative and/or overlain on scope vision/image data/representations. For example, needle- and/or scope-guidance features can be overlain on a scope image window to provide an augmented scope image view/window. The user interface component 318 can provide the user interface data 322 or other data to the one or more displays 42 and/or other display(s) for presentation of representations thereof.

The one or more communication interfaces 306 can be configured to communicate with one or more device/sensors/systems, such as over a wireless and/or wired network connection. A network in accordance with embodiments of the present disclosure can include a local area network (LAN), wide area network (WAN) (e.g., the Internet), personal area network (PAN), body area network (BAN), etc. In some embodiments, the one or more communication interfaces 1206 can implement a wireless technology such as Bluetooth, Wi-Fi, near field communication (NFC), or the like.

Although not shown in FIG. 3, the control system 50 can include and/or control other components, such as one or more pumps, flow meters, valve controls, and/or fluid access components in order to provide controlled irrigation and/or aspiration capabilities to a medical instrument (e.g., a scope), a device that can be deployed through a medical instrument, and so on. In some embodiments, irrigation and aspiration capabilities can be delivered directly to a medical instrument through separate cable(s). In some embodiments, the control system 50 can be coupled to the robotic system 10, the table 15, and/or a medical instrument, such as the scope 32 and/or a needle or other percutaneous-access instrument (not shown), through one or more cables or connections (not shown).

Figure 4:
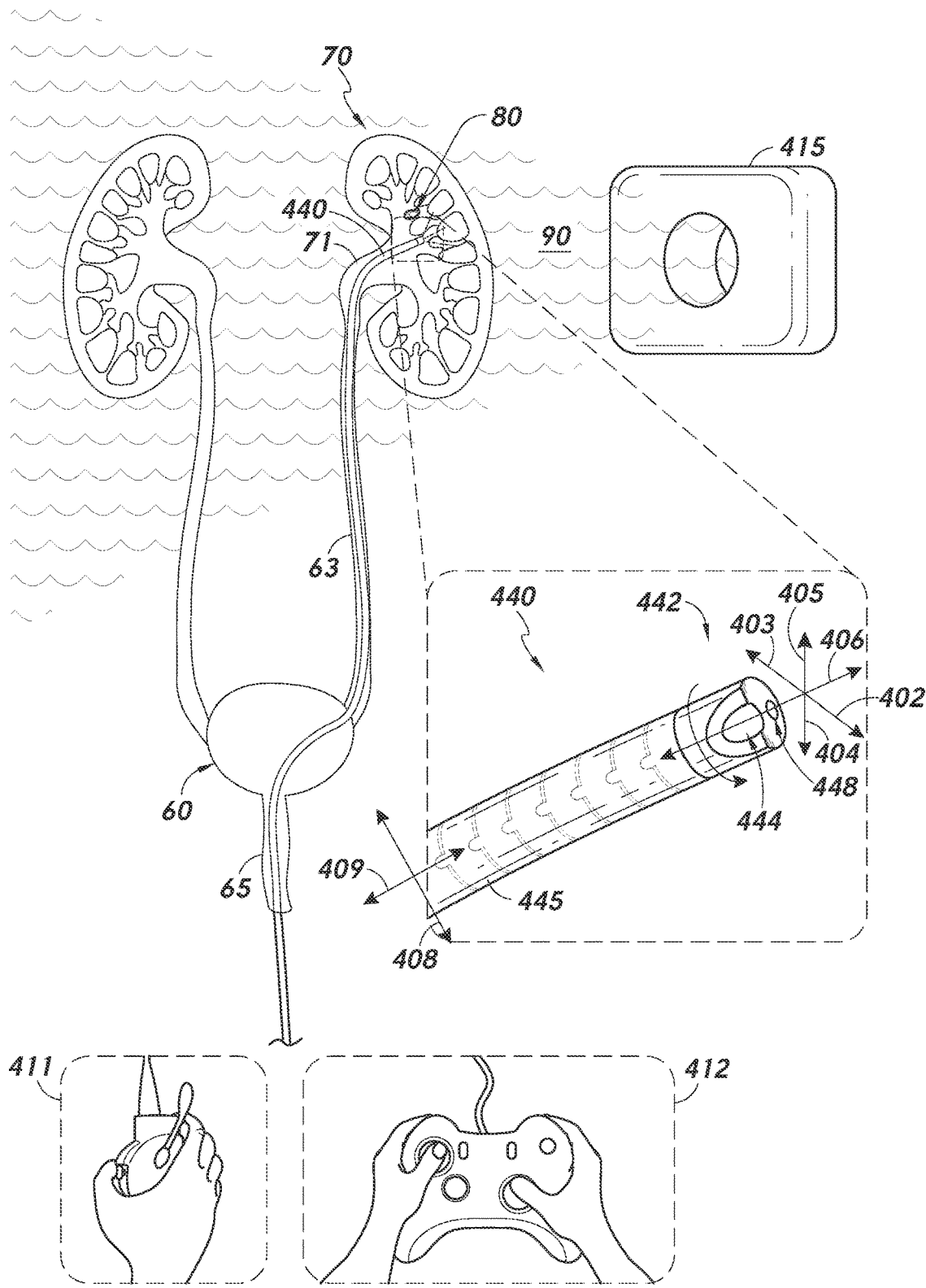
FIG. 4 illustrates a ureteroscope disposed in portions of the urinary system of a patient in accordance with one or more embodiments.

FIG. 4 illustrates a ureteroscope 440 disposed in portions of the urinary system of a patient in accordance with one or more embodiments of the present disclosure. As referenced above, ureteroscope procedures can be implemented for investigating abnormalities in human ureters and/or treating the same. For example, ureteroscope procedures can be implemented to treat and/or remove kidney stones. Such procedures may be implemented manually at least in part and/or may be performed using robotic technologies at least in part, such as the robotic system 10 shown in FIG. 1. For example, use of robotic devices and/or systems for certain endoscopic procedures can provide relatively greater precision, control, and/or coordination compared to strictly manual procedures. In some embodiments, the scope 440 includes a working channel 444 for deploying medical instruments (e.g., lithotripters, basketing devices, forceps, etc.), irrigation, and/or aspiration to an operative region at a distal end of the scope.

The scope 440 can be articulable, such as with respect to at least a distal portion of the scope, so that the scope can be steered within the human anatomy. In some embodiments, the scope 440 is configured to be articulated with, for example, five degrees of freedom, including XYZ coordinate movement, as well as pitch and yaw. In some embodiments, the needle sensor provides six degrees of freedom, including X, Y, and Z ordinate positions, as well as pitch, law, and yaw. Position sensor(s) of the scope 440 may likewise have similar degrees of freedom with respect to the position information they produce/provide. Figure illustrates multiple degrees of motion of the scope 440 according to some embodiments. As shown in FIG. 4, the tip 442 of the scope 440 can be oriented with zero deflection relative to a longitudinal axis 406 thereof (also referred to as a "roll axis").

To capture images at different orientations of the tip 442, a robotic system may be configured to deflect the tip 442 on a positive yaw axis 402, negative yaw axis 403, positive pitch axis 404, negative pitch axis 405, or roll axis 406. The tip 442 or body 445 of the scope 442 may be elongated or translated in the longitudinal axis 406, x-axis 408, or y-axis 409. The scope 440 may include a reference structure (not shown) to calibrate the position of the scope. For example, a robotic system may measure deflection of the scope 440 relative to the reference structure. The reference structure can be located, for example, on a proximal end of the endoscope 440 and may include a key, slot, or flange. The reference structure can be coupled to a first drive mechanism for initial calibration and coupled to a second drive mechanism to perform a surgical procedure.

For robotic implementations, robotic arms of a robotic system can be configured/configurable to manipulate the scope 440 using elongate movement members. The elongate movement members may include one or more pull wires (e.g., pull or push wires), cables, fibers, and/or flexible shafts. For example, the robotic arms may be configured to actuate multiple pull wires (not shown) coupled to the scope 440 to deflect the tip 442 of the scope 440. Pull wires may include any suitable or desirable materials, such as metallic and non-metallic materials such as stainless steel, Kevlar, tungsten, carbon fiber, and the like. In some embodiments, the scope 440 is configured to exhibit nonlinear behavior in response to forces applied by the elongate movement members. The nonlinear behavior may be based on stiffness and compressibility of the scope, as well as variability in slack or stiffness between different elongate movement members.

The scope (e.g., endoscope/ureteroscope) 440 may comprise a tubular and flexible medical instrument that is configured to be inserted into the anatomy of a patient to capture images of the anatomy. In some embodiments, the scope 440 can accommodate wires and/or optical fibers to transfer signals to/from an optical assembly and a distal end 442 of the scope 440, which can include an imaging device 448, such as an optical camera.

The camera/imaging device 448 can be used to capture images of an internal anatomical space, such as a target calyx/papilla of the kidney 70. The scope 440 may further be configured to accommodate optical fibers to carry light from proximately-located light sources, such as light-emitting diodes, to the distal end 442 of the scope. The distal end 442 of the scope 440 can include ports for light sources to illuminate an anatomical space when using the camera/imaging device. In some embodiments, the scope 440 is configured to be controlled by a robotic system similar in one or more respects to the robotic system 10 shown in FIGS. 1 and 2. The imaging device may comprise an optical fiber, fiber array, and/or lens. The optical components move along with the tip of the scope 440 such that movement of the tip of the scope results in changes to the images captured by the imaging device(s) 448.

For percutaneous nephrolithotomy (PCNL) procedure, access is made into the target calyx through the skin and intervening tissue of the patient. Generally, the preferred access to the calyces of the kidney is through the soft-tissue papilla structures, wherein access through such tissue may be generally associated with reduced risks of bleeding and/or other complications. Where a needle is inserted through a papilla structure, in addition to freedom from bleeding, such pathway can provide full access to the interconnected internal channels (e.g., calyces) of the kidney.

Although PCNL represents a relatively effective method for treating large renal calculi, many physicians choose other procedures due in part to the difficulty of accurately targeting the target papilla/calyx. More particularly, performing a PCNL involves using a needle to gain percutaneous access to a target calyx of the kidney through a patient's flank. This step can be considered extremely important to the ultimate success of the procedure because the physician must select a needle path to the kidney that does not traverse surrounding organs and also allows for a rigid instrument to reach and treat the urinary stone. If the physician fails to do so effectively, they risk causing a visceral or pleural injury or not being able to completely treat the stone. Due to these challenges, the learning curve associated with gaining percutaneous needle access to perform a PCNL a suitable patient position (e.g., the modified supine position) is very high.

In some procedures, the physician(s) study a patient's preoperative computed tomography (CT) images to determine the location of the urinary stone, the location of surrounding organs and bony structures, and examine the morphometry of the calyces. With this knowledge, the physician(s) may mentally generate a pre-operative plan for the percutaneous needle path. Typically, physicians must identify a posterior calyx to puncture to accommodate a rigid instrument. Specifically, a posterior calyx generally provides a relatively straight shot into the renal pelvis. Physicians must try to insert the needle into the kidney through the papilla to avoid damaging renal vasculature and cause bleeding. Intraoperatively, physicians in some procedures rely on fluoroscopy or ultrasound to guide the alignment and insertion of the needle to the target calyx. However, the resolution and interpretation difficulty associated with such imaging techniques can result in a relatively high degree of difficulty in satisfactorily executing the needle puncture. Therefore, embodiments of the present disclosure that provide improved tracking and visualization of target anatomical features, such as papillas and calyces, can improve operational results and appeal to a larger subset of physicians than other PCNL methodologies.

In some embodiments, the medical instrument (e.g., scope) 440 includes a sensor that is configured to generate and/or send sensor position data to another device. The sensor position data can indicate a position and/or orientation of the medical instrument 440 (e.g., the distal end 442 thereof) and/or can be used to determine/infer a position/orientation of the medical instrument. For example, a sensor (sometimes referred to as a "position sensor") can include an electromagnetic (EM) sensor with a coil of conductive material, or other form/embodiment of an antenna.

FIG. 4 shows an EM field generator 415, which is configured to broadcast an EM field 90 that is detected by the EM sensor on the medical instrument. The magnetic field 90 can induce small currents in coils of the EM position sensor, which may be analyzed to determine a distance and/or angle/orientation between the EM sensor and the EM field generator 415. Further, the medical instrument/scope 440 can include other types of sensors, such as a shape sensing fiber, accelerometer(s), gyroscope(s), satellite-based positioning sensor(s) (e.g., global positioning system (GPS) sensors), radio-frequency transceiver(s), and so on. In some embodiments, a sensor on a medical instrument can provide sensor data to a control system, which is then used to determine a position and/or an orientation of the medical instrument. In some embodiments, the position sensor is positioned on the distal end 442 of the medical instrument 440, while in other embodiments the sensor is positioned at another location on the medical instrument. the ureteroscope may be driven to a position in proximity to the target papilla.

In some implementations, as described in further detail below, the distal end of the ureteroscope 440 may be advanced to contact the target anatomical feature (e.g., papilla). With the position sensor associated with the distal end of the scope 440 in contact and/or proximity to the target anatomical feature, the position of the distal end of the scope 440 may be recorded as the target percutaneous access position to which the percutaneous-access instrument (e.g., needle) may be directed to access target calyx through the papilla.

Certain embodiments of the present disclosure advantageously help to automate and guide physicians through the process for gaining percutaneous to target anatomical features. For example, electromagnetic positioning and scope images can be used together to guide the insertion of a needle into a patient. Such solutions can allow non-expert physicians to gain access into the kidney in, for example, the modified supine position and to be able to perform PCNL.

Certain embodiments of the present disclosure involve position-sensor-guided percutaneous access to a target treatment site, such as a target location in the kidney. For example, where the scope 440 is fitted with one or more electromagnetic sensors, and the nehproscope access needle further includes one or more electromagnetic sensors, and such sensors are subjected to the electromagnetic field 90 created by the field generator 415, associated system control circuitry can be configured to detect and track their locations. In some embodiments, the tip of the ureteroscope 440 acts as a guiding beacon while the user inserts the percutaneous access needle. Such solutions can allow the user to hit the target from a variety of approaches, thereby obviating the need to rely on fluoroscopic or ultrasound imaging modalities.

In some embodiments, a control system (not shown in FIG. 4) associated with the scope 440 is configured to implement localization/positioning techniques to determine and/or track a location/position of a medical instrument, such as the scope 440 and/or percutaneous access needle (not shown). In some examples, as noted above, the EM field generator 415 is configured to provide an EM field 90 within the environment of the patient. The scope 440 and/or the percutaneous access needle can include an EM sensor that is configured to detect EM signals and send sensor data regarding the detected EM signals to the control system. The control system can analyze the sensor data to determine a position and/or orientation of the scope 440 (e.g., a distance and/or angle/orientation between the EM sensor and the EM field generator 415). Alternatively or additionally, in some examples, the control system can use other techniques to determine a position and/or an orientation of the scope 440. For instance, the scope 440 (and/or needle) can include a shape-sensing fiber, an accelerometer, a gyroscope, an accelerometer, a satellite-based positioning sensor (e.g., a global positioning system (GPS)), a radio-frequency transceiver, and so on. The control system can receive sensor data from the scope 440 and determine a position and/or an orientation thereof. In some embodiments, the control system can track a position and/or an orientation of the scope 440 in real-time with respect to a coordinate system and/or the anatomy of the patient.

The scope 440 may be controllable in any suitable or desirable way, either based on user input or automatically. The controls 411, 412 provide examples that may be used to receive user input. In some embodiments, the controls of the scope 440 are located on a proximal handle of the scope, which may be relatively difficult to grasp in some procedural postures/positions as the orientation of the ureteroscope changes. In some embodiments, the scope 440 is controlled using a two-handed controller, as in image 412. Although the controllers 411, 412 are shown as hand-held controllers, user input may be received using any type of I/O device, such as a touchscreen/pad, a mouse, a keyboard, a microphone, etc.

FIG. 5 (represented in parts 5-1 and 5-2) is a flow diagram illustrating a process 500 for accessing a target calyx or other organ of a patient in accordance with one or more embodiments of the present disclosure. FIG. 6 (represented in parts 6-1 and 6-2) shows certain images corresponding to various blocks, states, and/or operations associated with the process of FIG. 5 in accordance with one or more embodiments. The process 500 may involve percutaneous access to the kidney 70 for kidney stone removal (e.g., PCNL). Such percutaneous access may be desirable for extraction of stones that are sufficiently large that removal via ureteroscope is impractical or undesirable. For example, stones can be greater than 2 cm in diameter, whereas certain ureteroscopes have a working channel through which a stone or fragment can be removed that has a diameter of about 1.2 mm. Although breaking stones into smaller fragments for removal via ureteroscopy does work in many instances, studies have shown that leftover stone debris is often the source of new stone formation, necessitating future similar treatments. The processes described herein, although described in the context of ureteroscope, may apply to any other type of surgical procedure utilizing a position sensor (e.g., electromagnetic field sensor) and/or camera to track a target anatomical feature, such as a papilla or urinary stone.

At block 502, the process 500 involves accessing the kidney through the ureter of the patient using a ureteroscope 540, as described above. In particular, the operation of block 502 may involve advancing the scope 540 through the ureter 63, past the renal pelvis 71, and into an area at or near one or more calyces.

At block 504, the process 500 involves locating, using an image-capturing device (e.g. camera) associated with the distal end 542 of the endoscope, a kidney stone 580, for which the patient is to be treated. For example, the kidney stone 580 may be extracted at least in part as an objective of the process 500.

At block 506, the process 500 involves identifying a target papilla 579 that is exposed within a target calyx 575 through which access to the kidney stone 580 may be achieved. Identifying the target papilla 579 may be important for creating a workable tract through which access to the kidney stone 580 can be made via percutaneous access. For example, it may be necessary to determine an angle that is appropriate for access by a relatively rigid nephroscope in such a way as to access a calyx (e.g., minor calyx 575) through which the kidney stone 580 can be reached. In some implementations, it may be desirable or necessary to reach the kidney stone(s) 580 through a posterior calyx in order to provide a sufficiently straight access to the ureteropelvic junction 71. Generally, target minor calyces may be considered relatively small targets. For example, such calyces may be approximately 5-8 mm in diameter. Therefore, precise targeting can be critical in order to effectively extract the kidney stone(s).

The path through which needle/nephroscope access to the target calyx 575 is achieved may advantageously be as straight as possible in order to avoid hitting blood vessels around the renal pyramid 576 associated with the papilla 579 through which the needle/nephroscope may be positioned. Furthermore, the position of various critical anatomy of the patient may necessitate navigation through a constrained window of tissue/anatomy of the patient. For example, the lower pole calyces, below the $12^{th}$ rib, may provide a suitable access to avoid the pulmonary pleura. Furthermore, the access path may advantageously be medial to the posterior axillary line (e.g. approximately 1 cm below and 1 cm medial to the tip of the $12^{th}$ rib) to avoid the colon and/or paraspinal muscle. In addition, the access path may advantageously avoid coming within close proximity to the rib to avoid the intercostal nerves. Furthermore, by targeting entry in the area of the axial center of the calyx 575, major arteries and/or other blood vessels can be avoided in some instances.

At block 508, the process 500 involves tagging/recording the position of the exposed papilla 579 within the target calyx 579 through which the desired access is to be achieved. For example, position information/data may be represented/identifiable in a three-dimensional space, such as an electromagnetic field space, or a robot space (e.g., coordinate frame).

In order to record the position of the papilla 579, the scope 540 may be advanced to physically touch/contact the target papilla 579, as shown by the advanced scope tip 543, in connection with which such contact position may be identified and/or otherwise indicated as the target position by the scope 540 and/or operator. In some implementations, an electromagnetic beacon or other sensor device associated with the distal end/tip 542 of the ureteroscope may indicate the target position, thereby registering the target position in the electromagnetic field space. After contacting/touching the papilla 579 and recording the position, the end 542 of the scope may be retracted, and the depth of such retraction measured in some manner. In some implementations, the operator may be informed that the distal end 543 of the scope 540 has contacted the papilla 579 by monitoring the camera images generated thereby, which may generally become obstructed/blacked-out when contact is made. In some implementations, a user input device (e.g., pendant) can be used to inform the system that contact has been made with the target anatomical feature.

At block 510, the process 500 involves percutaneously introducing a medical instrument 550, such as a needle, into the patient. For example, such access may be made via the flank of the patients in some implementations. At block 512, the process 500 involves directing the percutaneously advanced medical instrument 550 towards the target position to ultimately traverse the target papilla 579 and access the target calyx 575 therethrough.

In some embodiments, visual confirmation of the entry of the tip of the needle 550 into the target calyx 575 may be provided by the camera of the scope 540. For example, the scope 540 may be backed-off from the target position, as described above, to thereby provide a field of view including the papilla 579 within the calyx 575, such that the tip of the needle 550 may be seen as it protrudes through the surface of the papilla 579.

With the target location recorded, a percutaneously-inserted medical instrument (e.g., the needle 550) may be directed towards the recorded position. However, where such recorded position is static, anatomical motion occurring after recordation of the target position may result in the target position not accurately reflecting the real-time position associated with the target anatomical feature through which access desired. For example, the act of inserting the needle 550 into the patient may cause certain anatomy around the target organ (e.g., the kidney 70) and/or the target organ itself to migrate and/or become distorted/misshaped in some manner, thereby causing the target anatomical feature (e.g., papilla 579) to assume a position/shape different than at the time at which the target access position was recorded. With respect to renal procedures, the ureteroscope 540 may be fixed to the position of the renal pelvis 71, such that deformation and/or motion of the kidney 70 relative to the ureteroscope may result in such target position corruption. Therefore, the papilla 579 may not be accurately tracked once anatomical motion is introduced into the system.

Once needle access has been made to the calyx 575, a larger-diameter device may be exchanged for the needle 550 to provide a larger port for stone removal. In some implementations, the needle 550 comprises a stylet and a cannula. With the needle tip advanced into the calyx 575, the stylet may be removed, leaving the cannula to form an open port to the location of the kidney stone. Through the cannula, a guide wire may be placed and used to perform the remainder of the process to remove the stone 580. for example, the guide wire can be used to pass a deflated balloon or dilator along the wire. The balloon or dilator can be expanded to create a port large enough introduce a hollow suction tube, such as a nephrostomy tube, directly into the calyx 575. At this point, a nephroscope or any one of a number of other instruments may be introduced into the suction tube to assist in removing the stone 580. For example, a stone breaker, laser, ultrasound, basket, grasper, drainage tube, etc. may be used to remove the stone or fragments thereof, and/or drainage tubes, such as nephrostomy catheters, may be deployed down the suction tube to reduce intra-renal pressure. Any combination of such functionality may be embodied in the nephroscope (not shown) and/or the ureteroscope 540.

Target Localization

Various aspects of the present disclosure relate to systems, devices, and methods for target (e.g., target anatomical feature) localization in connection with medical procedures. In particular, target localization in accordance with the present disclosure can involve various steps and/or functionality, including recording/tagging a position of a target anatomical feature (e.g., papilla) using an endoscope (e.g., ureteroscope), determining/registering a positional offset/translation between the target anatomical feature and the endoscope (e.g., position sensor associated therewith) for the purpose of determining the position of the target anatomical feature based on the position of an endoscope that is not in physical contact with the target anatomical feature, and/or dynamically updating a target position associated with the target anatomical feature based on electromagnetic sensor and/or camera data associated with the ureteroscope. As described, a static position marker may be registered/recorded to identify a target position associated with a target anatomical feature/landmark. In some embodiments, the present disclosure provides systems, devices, and methods for guiding and/or automating endoscope and/or percutaneous-access instruments based at least in part a static position marker in view of certain target localization techniques. Target localization in accordance with embodiments of the present disclosure can apply to any type of robotic endoscopy procedure.

Figure 7:
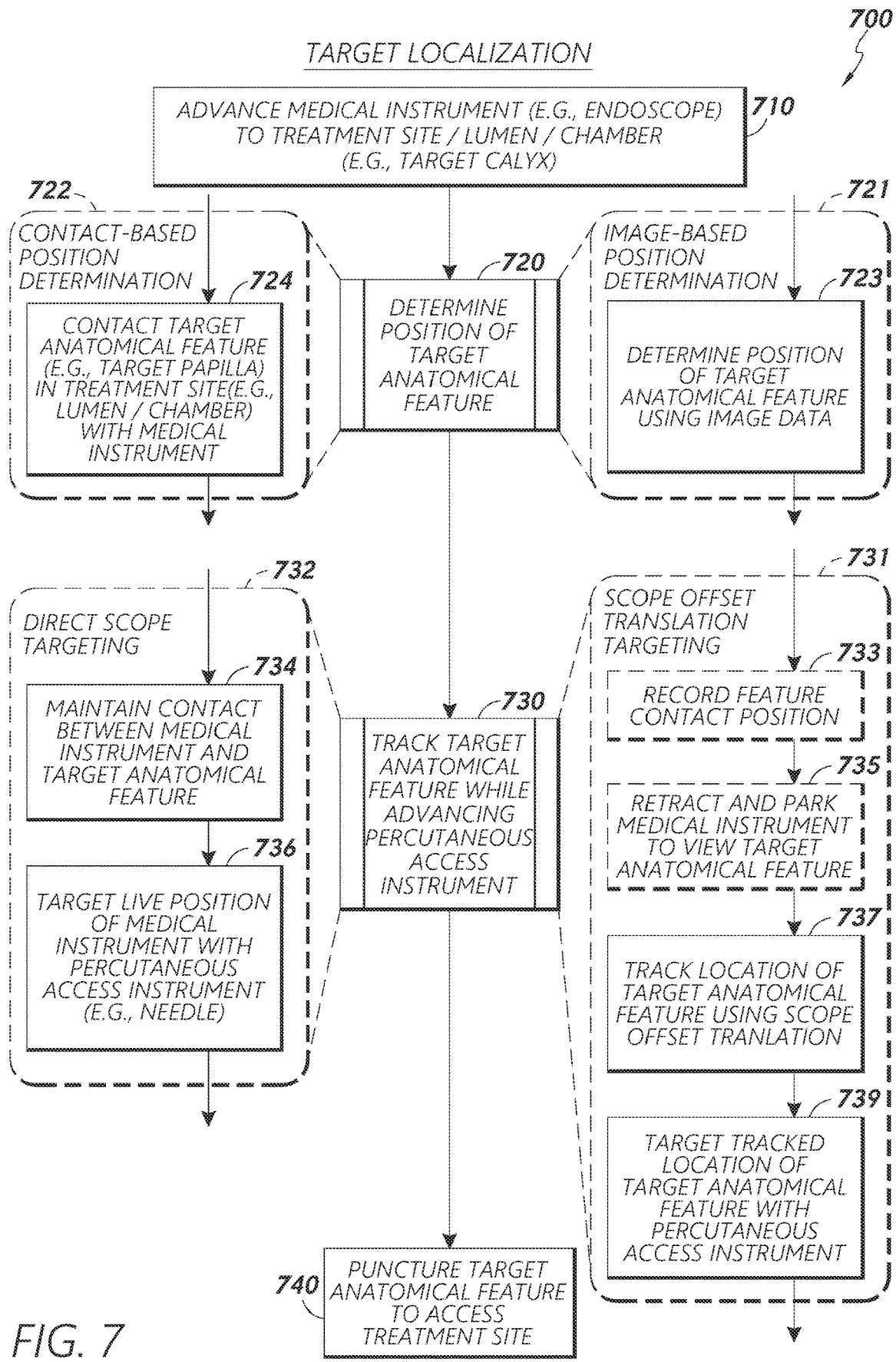
FIG. 7 is a flow diagram illustrating a process for localizing a target anatomical feature in accordance with one or more embodiments.

FIG. 7 is a flow diagram illustrating a process 700 for localizing a target anatomical feature in accordance with one or more embodiments. Generally, target localization may be implemented to locate the position of a target anatomical feature (e.g., papilla) with respect to a ureteroscope. The target position may be recorded/saved with respect to an electromagnetic field generator/space, a robot coordinate frame, and/or an anatomical coordinate frame defined by, for example, kidney mapping. At block 710, the process 700 involves advancing a medical instrument, such as a scope (e.g., ureteroscope), to the treatment site, such as a lumen or chamber disposed at least partially within a target organ. For example, the operation of block 710 may involve advancing the medical instrument to a target calyx of the kidney of a patient.

As referenced above, robotic endoscope-guided percutaneous access in accordance with aspects of the present disclosure can utilize target localization technology with respect to the target anatomical feature to guide/determine a percutaneous access path for accessing the target anatomical feature/site. For example, position-tracking mechanisms/sensors associated with the distal end of the medical instruments (e.g., scope) and/or a percutaneous-access instrument (e.g., needle) can be implemented in order to guide the physician/technician in aligning the percutaneous-access instruments with the treatment site (e.g., target calyx). Accurate, real-time target localization/tracking, as enabled by aspects of the present disclosure, can enable relatively precise single-stick access to the treatment site.

At block 720, the process 700 involves determining a position of the target anatomical feature. For example, determining the position of the target anatomical feature can be performed in any suitable or desirable way, such as using an at least partially contact-based position-determination subprocess 722 or an at least partially image-based position-determination subprocess 721, which are described below in connection with blocks 724 and 723, respectively.

With respect to certain contact-based position determination processes, at block 722, the process 700 involves contacting the target anatomical feature in the treatment site with the distal end of the medical instrument. For example, the medical instrument may comprise a sensor device, such as an electromagnetic sensor/beacon that may indicate a position of the distal end of the medical instrument, and therefore, with the distal end of the medical instrument disposed against and/or adjacent to the target anatomical feature, such position reading can be relied upon as indicating the present position of the target anatomical feature. Contact-based position determination may not be needed when an image-processing approach is implemented to provide the 3D location/position of the target. For example, at block 723, the process 700 involves determining the position of the target anatomical feature using image data input from the endoscope camera.

The process 700 proceeds to subprocesses 730, which may involve tracking/localizing the target anatomical feature over an operative period while advancing a percutaneous-access instrument, such as a needle or the like, over/along an access path in the direction of the target anatomical feature. In some implementations, electromagnetic (EM) position-sensing technology is used to track/localize the target anatomical feature. For example, as described above, the target anatomical feature (e.g., papilla) may be contacted by the distal end portion of the scope at one or more positions/areas, wherein the local position and orientation of the target feature(s) (e.g., infundibular axis) may be determined based thereon with respect to position(s) of the scope. In some embodiments, as described in greater detail below with respect to FIGS. 15-17, a mapping of the target site (e.g., target calyx/papilla and associated infundibula) may be generated based on a plurality of recorded positions from EM sensor data.

The subprocess 730 may be implemented in various ways. For example, as shown as the subprocess 732, live direct instrument (e.g., scope) targeting/tracking may be implemented to provide operational tracking of the target anatomical feature. For example, throughout the relevant operative period, the distal end of the medical instrument may be maintained in contact with the target anatomical feature (block 734), such that position sensor data indicated by the medical instruments may provide a real-time accurate location of the target anatomical feature. Therefore, as shown at block 736, the live position of the medical instrument may be targeted to provide the desired percutaneous access path. However, with the distal end of the medical instrument in close proximity/contact with the target anatomical feature, real-time visualization of the target anatomical feature may not be possible or sufficiently clear due to the obstruction of the target anatomical feature by the feature itself in the field of view of the camera(s). That is, the camera associated with the local instruments may be sufficiently blocked or obscured by the mass of the target anatomical feature, thereby preventing the physician/user from having visual confirmation of penetration of the target anatomical feature by the percutaneous-access instrument (e.g., needle).

An alternative subprocess 731 is shown for tracking the target anatomical feature while still maintaining a clear visual of the target anatomical feature during approximation of the percutaneous-access instrument. The subprocess 731 involves localizing the target anatomical feature using a determined position offset/translation between the position of the scope and the position of the target anatomical feature and determining live/present position(s) of the target anatomical feature by applying the offset/translation to the present position of the scope.

At block 733, the subprocess 731 may involve recording the determined position of the target feature contact position associated with the contact with the target anatomical feature implemented in connection with the operation of block 720, described above. As an example, the user may provide input to notify the relevant control/medical system of the feature-contact position of the target anatomical feature by tagging/registering the position of the exposed face of the target anatomical feature (e.g., papilla face exposed within the target calyx) in some manner. Such tagging may be implemented through provision of user input in some manner or may be substantially automatic based on perceived tissue contact, or the like. The position data may be captured in volatile and/or non-volatile data storage of certain control circuitry as shown and described herein.

After determining the location/position of the target anatomical feature, the scope may be retracted and/or parked in a manner such that it faces the target anatomical feature (e.g., papilla) to provide visualization thereof, as indicated at block 735. Such parking may be performed with the aid of certain scope-guidance feature(s)/overlay(s) presented on or around/near a camera view interface window, described in detail below with respect to FIGS. 9-13.

Rather than continuing to maintain the medical instrument (e.g., scope) in contact/proximity with the target anatomical feature to provide live operational tracking as with subprocess 732, the subprocess 731 may involve determining the position of the target anatomical feature based on a determined positional offset/translation between the position/orientation of the parked scope and the position/orientation of the target anatomical feature. When parking the scope, the scope may be retracted a distance away (e.g., in the proximal direction) from the target anatomical feature to thereby allow the medical instrument to clearly capture the target anatomical feature in a field of view of the camera(s) associated therewith. For example, in some implementations, the physician/user may inform the system in some manner when the medical instrument has been parked a desired distance away from the target anatomical feature.

By way of clarification, it is noted that the subprocesses 731, 732 represent alternative implementations of the subprocess 730. That is, the process 700 may generally involve implementation of either the subprocess 732 or the subprocess 731, but not both.

In some cases, it may be assumed that as the scope remains inside of the target calyx, the papilla-to-scope offset/translation is generally preserved over time. In the absence of relative movement of the target anatomical feature with respect to the scope position sensor(s), the target position can be continuously updated based on determined current scope position. The position data (e.g., EM data) collected in connection with retraction/reorientation of the scope can be used to determine the offset/translation of the papilla location/orientation with respect to the scope. For example, according to one use case, the retraction/positioning of the scope could be approximately 5 mm in front of the papilla and 2 mm to the left. Such position offset may be used to determine the position of the target as relative to a current position of the scope. The translation/offset information may further incorporate orientation information, which may be enabled in any suitable or desirable way. In the event of relative movement between the target anatomical feature and the scope, the determined offset/translation may become unreliable. In some implementations, relative movement compensation may be implemented to compensate for, and/or adjust, the offset/translation when the relative position/orientation between the scope and target anatomical feature changes.

The subprocess 731 may or may not include/involve the contacting 724 and retracting 735 steps, wherein the user physically contacts the target papilla location and retracts the scope to show the papilla in the field of view of the scope. For example, where image-based tagging 721 is implemented in connection with block 720, it may not be necessary to physically contact the target anatomical feature to determine the position/location thereof. Rather, the position/location may be determined using target-identification mechanism(s) based on image data captured/generated by one or more cameras of the scope/instrument. For example, in some embodiments, the target is identified and tracked using multiple frames of image/vision and/or position (e.g., EM) data. Examples of such target position determination are described below in connection with FIG. 18. In some implementations, by looking at the target anatomical feature (e.g., papilla) from two distinct positions and/or alignments, the target position can be estimated/determined with respect to three-dimensional space, as described below with respect to FIG. 18.

At block 739, the subprocess 731 involves targeting the tracked location of the target anatomical feature with the percutaneous-access instrument. For example, the centroid of an identified papilla shape or form in a real-time image of the treatment site may be used as the target position for a percutaneous-access instrument. At block 740, the process 700 involves puncturing the target anatomical feature, either without visual confirmation of the target anatomical feature with respect to the subprocess 732 or with visual confirmation in accordance with the subprocess 731, depending on the particular implementation of the process 700.

The various position sensors used in connection with embodiments of the present disclosure, such as for determining/recording the feature-contact position at block 733 or targeting the live instrument position at block 736, may be any type of position sensors. As an example, such sensor(s) may be electromagnetic (EM) sensors/probes. With respect to the scope, the position sensor may be attached or integrated with, proximal to, the tip thereof. The sensor(s) may comprise a coil connected to an electrical wire running the length of the scope, which is connected to external control circuitry configured to interpret electrical signals generated at the coil and passed down the wire. Examples of types of position sensor devices that may be implemented in connection with embodiments of the present disclosure include, but are not limited to, accelerometers, gyroscopes, magnetometers, fiber optic shape sensing (e.g., via Bragg gratings, Rayleigh scattering, interferometry, or related techniques), etc. Depending on the implementation, registration to a separate form of patient imagery, such as a CT scan, may or may not be necessary to provide a frame of reference for locating a urinary stone within the patient.

With respect to EM-type sensors, such as coils or other antennas, such sensor devices can be configured detect changes in EM fields as the EM sensor moves within the field (e.g., within the kidney). Therefore, certain embodiments are implemented using one or more EM generators configured to emit EM fields that are picked-up and/or affected by the EM sensor(s). The EM generator(s) may be modulated in any suitable or desirable way, such that when their emitted fields are captured/affected by the EM sensor(s) and are processed by appropriate control circuitry, signals from different EM generators are separable to provide additional dimensions/degrees-of-freedom of position information. EM generators may be modulated in time or in frequency, and may use orthogonal modulations so that each signal is fully separable from each other signal despite possibly overlapping in time. Further, separate EM generators may be oriented relative to each other in Cartesian space at non-zero, non-orthogonal angles so that changes in orientation of the EM sensor(s) will result in the EM sensor(s) receiving at least some signal from at least one of the EM generators at any instant in time.

With further reference to the recording of the feature-contact position at block 733 of FIG. 7, EM position data may be registered to an image of the patient captured with a different technique other than EM (or whatever mechanism is used to capture the alignment sensor's data), such as a CT scan, in order to establish a reference frame/space for the EM data. In addition to the scope, the percutaneous-access needle may include one or more position/alignment sensors, such as an EM sensor. Position/alignment data received from the needle EM sensor may be received and processed similarly to scope position data as describe above. It should be understood that the various processes described herein may be performed wholly or partially manually and/or wholly or partially using robotics.

The processes disclosed herein may be implemented in connection with procedures other than kidney stone removal procedures, such as gallbladder stone removal, lung (pulmonary/transthoracic) tumor biopsy, and others. Generally, any type of percutaneous procedure may be performed by using an endoscope configured to capture image data for feature identification and tracking using neural network processing in accordance with embodiments of the present disclosure. Additional examples include stomach operations, esophagus and lung operations, etc. Further, the objects to be removed do not necessarily need to be urinary stones, they may be any object, such as a foreign body or object created within the human body.

The process 700 can be implemented to localize the target anatomical feature based at least in part on the determination of scope offset/translation from the target anatomical feature, as may be implemented in connection with any of the embodiments disclosed herein. Electromagnetic sensor(s) incorporated in the distal end portion of the ureteroscope may have any suitable or desirable form and/or configuration, including one or more conductor coils, rings, cylinders, and/or the like, wherein local distortion in the broadcast electromagnetic field caused by such conductive element(s) can provide information relating to the position thereof.

Using an electromagnetic positioning system, including an electromagnetic field generator and one or more electromagnetic sensors/beacons, the present location of the papilla can be tracked to facilitate real-time targeting of the papilla by the percutaneous access instrument (e.g., needle). For example, the targeting position of the papilla may be updated in real-time based on electromagnetic sensor data, such as real-time electromagnetic sensor data relating to one or more sensors/beacons associated with the distal end of the endoscope. In some implementations, even in the absence of real-time visual confirmation and/or other image data associated with the scope and target anatomical feature, the position and/or orientation of the scope may be relied upon to determine the real-time tracking location for the target anatomical feature.

Endoscope and Target Feature Position Translation

Figure 8:
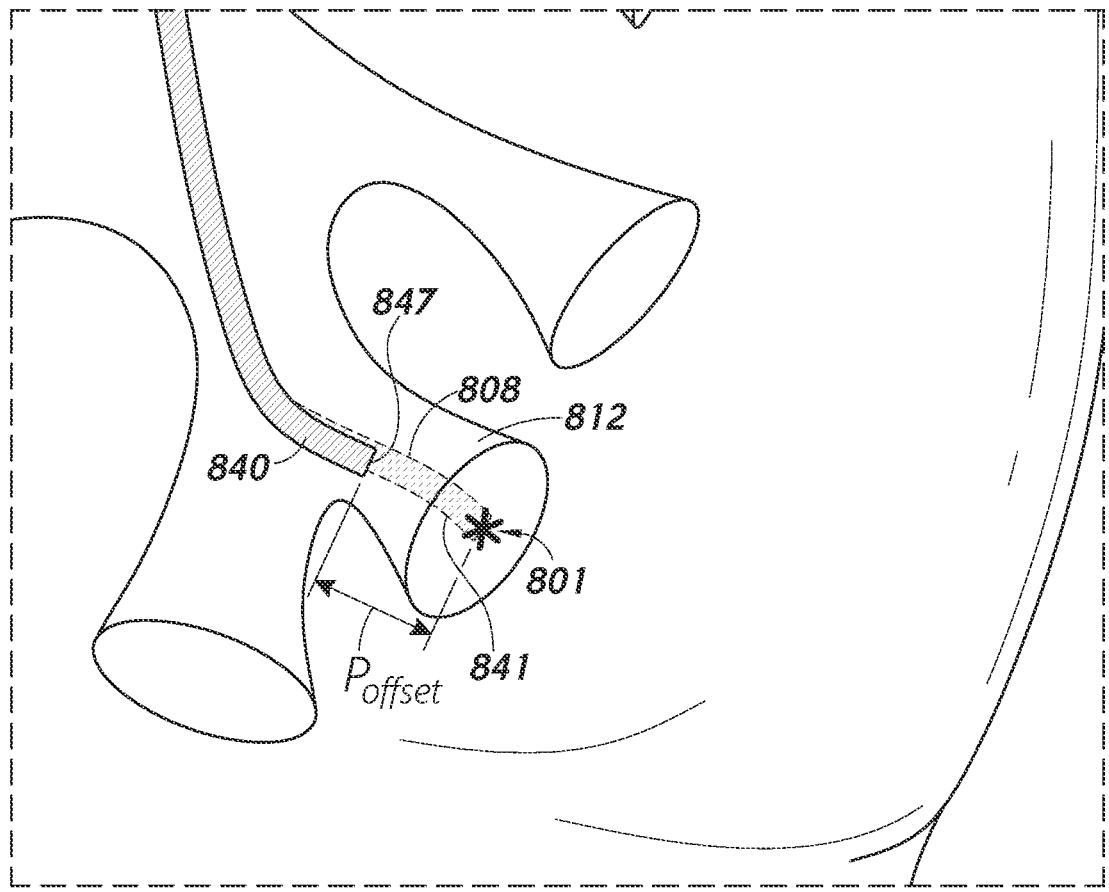
FIG. 8 shows a scope device disposed within a target calyx for target localization in accordance with one or more embodiments.

FIG. 8 shows a scope device 840 disposed within a target calyx 812 for target localization in accordance with one or more embodiments. Certain process(es) may be implemented to determine and/or maintain a known offset $P_{offset}$ between a recorded papilla contact position 801 and a present position of the distal end 847 of the endoscope 840. The position sensor(s)/beacon(s) of the scope 840 may be configured to provide sensor data indicating five or six degrees-of-freedom (DOF) with respect to the position of the scope 840. For example, coil or other type of sensor device(s) may have a cylinder-type shape, or any other shape allowing for three-dimensional position data as well as yaw and/or pitch data. In some embodiments, the position sensor(s)/beacon(s) do not provide roll information, such as in embodiments including five-DOF sensor(s). In some embodiments, multiple five-DOF sensors may be used/combined and disposed at a relative axial angle with respect to one another, wherein the combined data provided/generated based on such position sensor(s)/beacon(s) can define a plane that can be used to construct six DOF providing scope roll information.

In some implementations, a breath-hold may be executed for the patient during at least a portion of the scope offset determination/maintenance process(es), which may allow for such operations to be executed without the necessity of accounting for anatomical motion associated with the pulmonary cycle. For example, the patient may be subject to a breath-hold during at least the tagging and retracting portions of the process(es). In some implementations, it may not be necessary to update the determined translation $P_{offset}$ in real time if it is assumed that any anatomical motion experienced after determination of the offset may affect the parked endoscope and the target anatomical feature (e.g., papilla) in a like manner, such that the transform/translation between the two positions can be assumed to be substantially constant irrespective of anatomical motion and/or other factors.

Determination of the relative transform $P_{offset}$ between the parked scope end 847 and the previously-recorded papilla contact position 801 can be determined using strictly electromagnetic position sensor data, or may be determined using image processing, as described herein. For example, calibration of the scope camera with respect to the electromagnetic field space may allow for visual determination of distance and/or position changes between the contact position 801 and the retracted position 847.

The path 808 of retraction between the position 841 of the scope and the position 840 of the scope may or may not be linear. In some implementations, such as with respect to lower-pole target calyces/papillas, the retraction path may be at least partially arc-like. Therefore, the translation $P_{offset}$ may be determined with respect to more than just straight-line distance, and may incorporate scope orientation and/or other position-related parameters. Therefore, the translation $P_{offset}$ may be considered a six-degrees-of-freedom translation/transform in some implementations. Such translation determination may account at least in part for cases in which the target calyx 812 and/or associated infundibulum may have a central axis/centroid that does not necessarily align with the retraction path taken by the scope 840. Therefore, translation with respect to six or more degrees of freedom may be desirable to produce a mapping translation/transform that sufficiently accurately represents the positional offset $P_{offset}$ between the position 801 and the position 847.

In some implementations, certain image data may be collected and used for identifying target anatomical features. For example, systems, devices, and methods of the present disclosure may provide for identification of target anatomical features in real-time endoscope images, wherein identification of a target anatomical feature in an image may prompt certain responsive action. For example, control circuitry communicatively coupled to robotic endoscopy and/or percutaneous-access device(s) may be configured to track movements of a target feature and take action, such as articulating one or more portions of the endoscope (e.g., distal end portion 847), or adjusting target position data. For example, the control circuitry may be configured to cause the endoscope to articulate so as to center the target position/points at or near a center of the field of view of an interface and/or image field of the endoscope camera and/or to maintain a desired positional offset (e.g., $P_{offset}$) between the scope and the target anatomical feature.

By utilizing robotic-assisted percutaneous access, a physician may be able to perform operating target access and treatment. Furthermore, percutaneous access can be further assisted utilizing automated target identification and tracking in accordance with aspects of the present disclosure described in greater detail below, which may be relied upon for accurately maintaining the target position for percutaneous access guidance. Percutaneous access guided by scope-enabled target tracking in accordance with aspects of the present disclosure can be relatively less skill-intensive. In some implementations, a single operator or robotic system may carry out the process. Furthermore, the need for fluoroscopy can be obviated.

Scope Offset/Parking Guidance

As described above, inventive features of the present disclosure may be utilized in endoscope/ureteroscope-based targeting for percutaneous kidney access, wherein an electromagnetic beacon-/sensor-equipped ureteroscope and/or an electromagnetic beacon-/sensor-equipped percutaneous access instrument (e.g., needle) are used to gain percutaneous renal access through a target papilla and into a target calyx. With respect to scope-targeting procedures, the efficacy of percutaneous access to the target location/site, such as to access a target calyx in which the scope is parked, can depend on where the physician/technician parks the distal end of the scope with respect to the target calyx/papilla. In particular, the parking of the distal end of an endoscope/ureteroscope, as described in accordance with embodiments of the present disclosure, can relate to the position and/or heading of the distal end of the ureteroscope with respect to the target papilla through which percutaneous access is to be made. To provide further context to the various scope parking features disclosed herein, certain surgical systems and environments are described below relating to endoscope parking.

Figure 9:
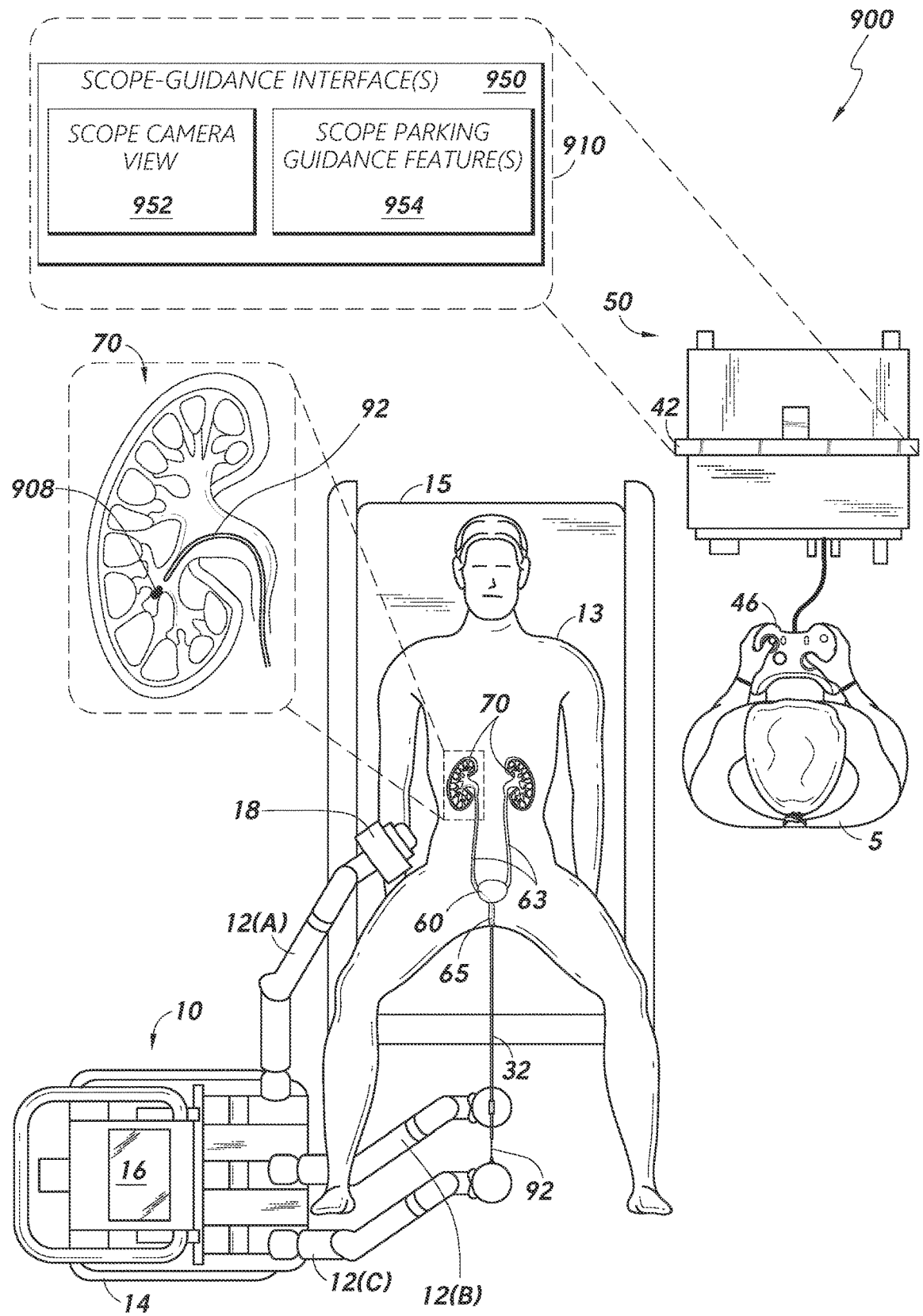
FIG. 9 illustrates a robotic medical system arranged to facilitate navigation of a scope within a patient in accordance with one or more embodiments.

FIG. 9 illustrates a robotic medical system 900 arranged to facilitate navigation of a scope within a patient in accordance with one or more embodiments. For example, the physician 5 can connect an endoscope 92 to a robotic arm 12(*c*) of a robotic system 10 and/or position the scope 92 at least partially within a medical instrument (e.g., catheter/sheath) and/or the patient 13. The scope 92 can be connected to the robotic arm 112(*c*) at any time, such as before the procedure or during the procedure (e.g., after positioning the robotic system 10). The physician 5 can then interact with a control system 50, such as with the I/O device(s) 46, to navigate the scope 92 within the patient 13. For example, the physician 5 can provide input via the I/O device(s) 46 to control the robotic arm 112(*c*) to navigate the scope 92 through the urethra 65, the bladder 60, the ureter 63, and up to the kidney 70.

As shown, the control system 50 can present a screen 910 including one or more scope-guidance interfaces 950 via the display(s) 42 to view a real-time camera image/view 952 captured by the scope 92 to assist the physician 5 in controlling the scope 92. The physician 5 can navigate the scope 92 to locate, for example, a kidney stone, target anatomical feature(s), and/or the like. In some embodiment, the control system 50 can be configured to implement certain localization technique(s) to determine a position and/or an orientation of the scope 92, which can be viewed by the physician 5 through the display(s) 42 to also assist in controlling the scope 92. Further, in some embodiments, other types of information can be presented through the display(s) 42 to assist the physician 5 in controlling the scope 92, such as x-ray images of the internal anatomy of the patient 13.

The physician 5 can use the controls 46 to drive the scope 92 to find/identify the kidney stone 908 or other artifact targeted for removal/treatment. The physician 5 may further drive the scope to localize the target papilla and to occupy a desired parking position. Such scope driving can be guided at least in part by the scope parking guidance feature(s) 954 of the scope-guidance interface(s) 950, which are described in detail below.

Figure 10A:
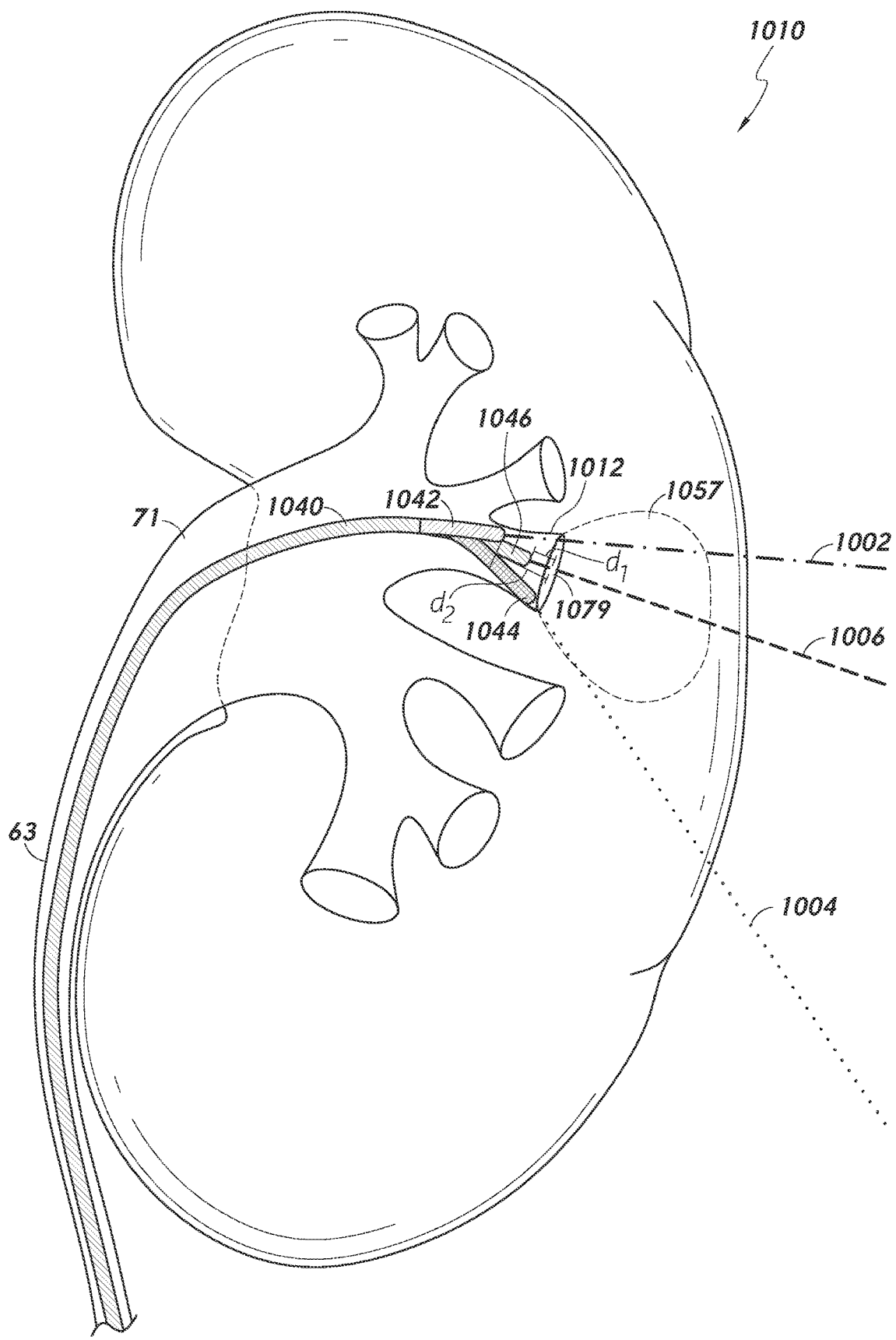
FIGS. 10A and 10B show renal anatomy with ureteroscope(s) parked at various positions in accordance with one or more embodiments.
Figure 10B:
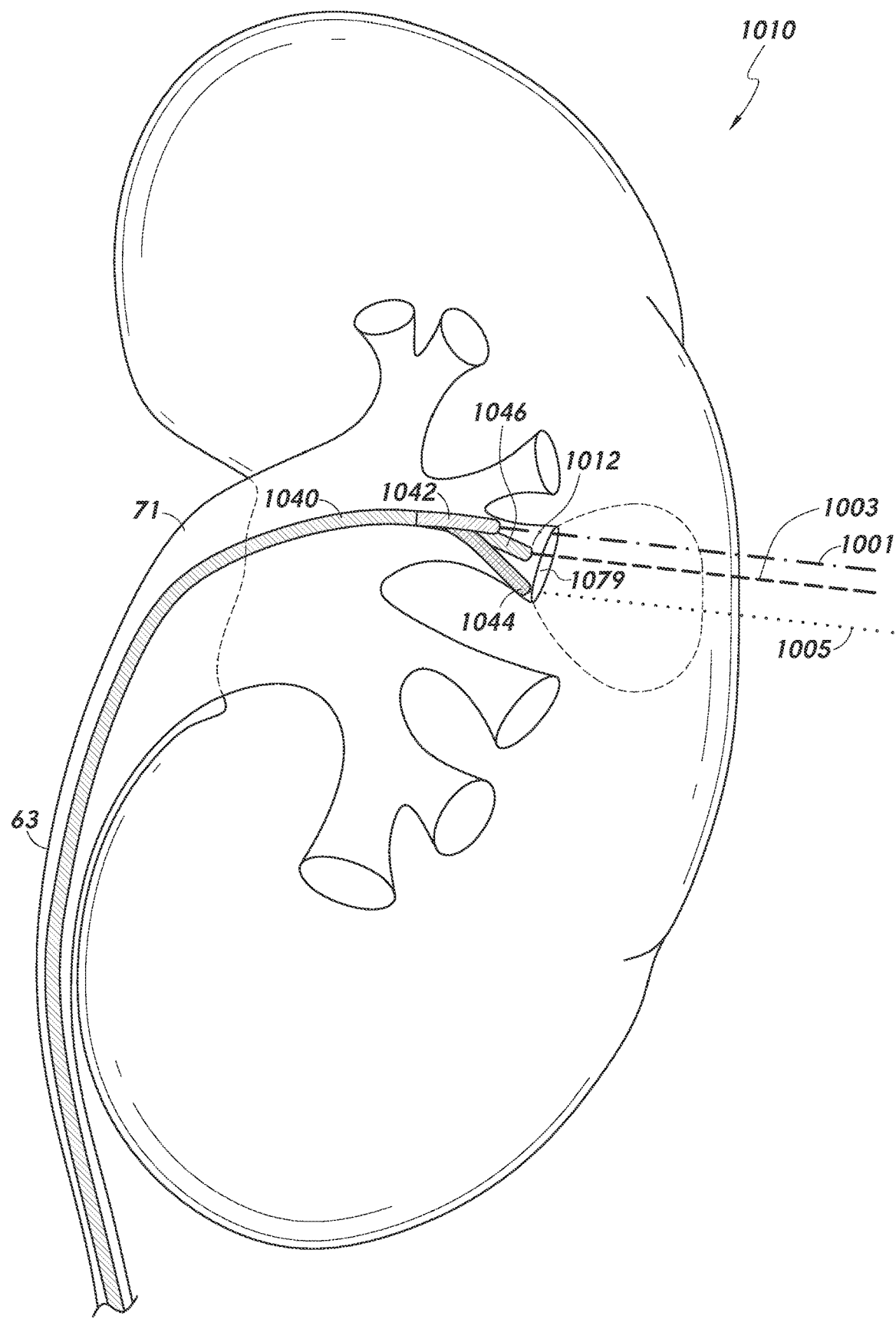

FIGS. 10A and 10B show renal anatomy with ureteroscope(s) parked at various positions in accordance with one or more embodiments. FIG. 10A shows a ureteroscope 1040 disposed within the ureter 63, renal pelvis 71, and/or calyces (e.g., major and/or minor calyces) of a kidney 1010. For example, an operator/physician may drive the scope 1040 to the calyx 1012 and use an electromagnetic beacon associated with a distal end/tip of the scope 1040 as a target to which a percutaneous access instrument (e.g., needle) may be directed. In some embodiments, the scope 1040 is used to register the position of the target papilla 1079, after which the scope 1040 is retracted some amount and parked a distance away from the papilla 1079 to provide a desired position of the scope for visualization of the percutaneous access using the camera of the scope 1040. In some implementations, the target position targeted by the percutaneous access instrument (not shown) may be determined based on a known offset distance, orientation, and/or position of the scope 1040 relative to the target papilla 1079 or other anatomical feature. Therefore, functionality disclosed herein can facilitate the proper/desired parking of a scope device that may be implemented and relied upon for dynamic targeting purposes, as described herein.

With respect to percutaneous access of the calyces, such as may be implemented in order to reach/treat a kidney stone, access through the renal pyramid/papilla 1057, 1079 may be necessary or desirable in order to access the target calyx 1012 without excessive bleeding. Furthermore, access through the papilla 1079 can give full access to the calyx network of the kidney 1010.

The target calyx 1012 surrounds the papilla 1079 (i.e., renal pyramid apex; shown in dashed-line form in FIGS. 10A and 10B for clarity) through which an appropriate percutaneous access to the target calyx 1012 may be gained. Generally, one or more points at or near the distal tip/end of the scope 1040 may be used as the target for percutaneous access. For example, as described above, the distal tip/end of the scope 1040 may have one or more electromagnetic sensors or beacons associated therewith for determining a position/orientation thereof in an electromagnetic field. The illustration of FIG. 10A shows three different possible example parking positions (1042, 1044, 1046) of the distal end of the scope 1040. FIG. 10A further shows a respective coaxial trajectory (1002, 1004, 1006) associated with each of the scope parking positions. Such trajectories may be determined based on the derived position and/or orientation/alignment information relating to each of the scope parking positions and may represents possible paths along which percutaneous renal access may be guided/achieved.

FIG. 10A shows a parking position 1046, in which the distal end of the scope 1040 is generally aligned with a center axis 1006 of the target calyx 1012 and/or associated infundibulum. FIG. 10A further shows another parking position 1042, wherein the distal end of the scope 1040 is positioned a distant $d_2$ that is undesirably far away from the papilla 1079 and/or misaligned with the central axis of the target calyx 1012 and/or associated infundibulum. For example, as shown as trajectory 1002, the parking position 1042 may generally produce a target trajectory 1002 that is not centered with the papilla 1079 and/or associated renal pyramid. FIG. 10 further shows another parking position 1044 that is misaligned with the axis of the target calyx 1012, papilla 1079, and/or associated infundibulum.

FIG. 10B shows minimum-tract percutaneous access paths corresponding to each of the illustrated example scope parking positions. Specifically, FIG. 10 shows a minimum-tract path 1001 associated with the parking position 1042, wherein the scope 1040 is parked undesirably far from the target papilla 1079 and/or in misalignment with the center thereof. FIG. 10B further shows a minimum-tract path 1005 associated with the misaligned parking position 1044. The access path 1003 associated with the parking position 1046 may generally be aligned with a central area of the calyx 1012. Based on the access paths shown in FIGS. 10A and 10B, the parking position 1046 may be considered a suitable or desirable parking position for viewing and/or accessing the calyx 1012.

Certain embodiments of the present disclosure advantageously provide various mechanisms and means for estimating or determining a target calyx/papilla location, as well as certain visualization mechanisms/means to facilitate the guidance of the operator to correctly park the ureteroscope at the target calyx in an effective position, alignment, and/or orientation for percutaneous access targeting. Embodiments of the present disclosure advantageously provide certain visual guidance/assistance features and/or functionality to facilitate the effective parking of an endoscope at a target site, such as a ureteroscope at or near a target calyx within a kidney of a patient.

FIGS. 11, 12A, 12B, 14-1, and 14-2 show certain scope-guidance features that may be used to guide an operator/physician in parking/positioning an endoscope at a desirable position with respect to a target papilla. Such features may be generated and/or displayed in any suitable or desirable manner or form. For example, one or more markers/icons may be generated and/or displayed on or around a camera view presented on a display device associated with a robotic control system, wherein such markers/icons direct a physician/operator with respect to how the endoscope should be manipulated or actuated to position the distal end of the endoscope in a suitable or most effective parking position. The scope parking guidance features can direct the user/operator to align, for example, the ureteroscope with a target papilla, such that the position of the distal end of the ureteroscope may be effectively targeted using a percutaneous access instrument (e.g., needle).

Figure 11:
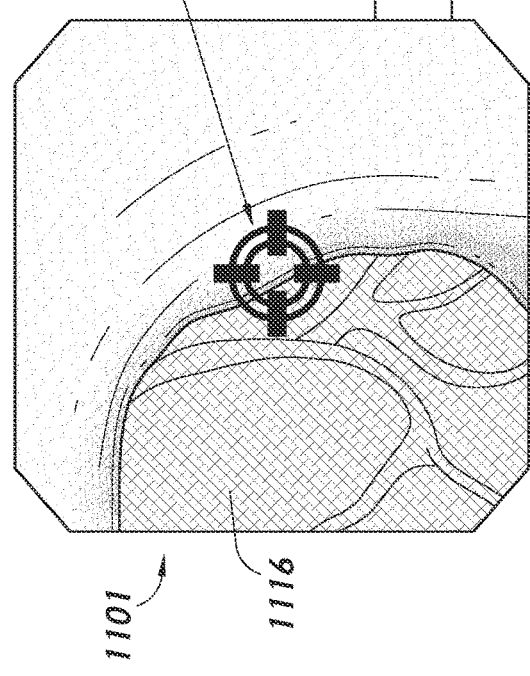
FIG. 11 illustrates configurations of a scope camera view/window including a scope-targeting feature in accordance with one or more embodiments.
Figure 11:
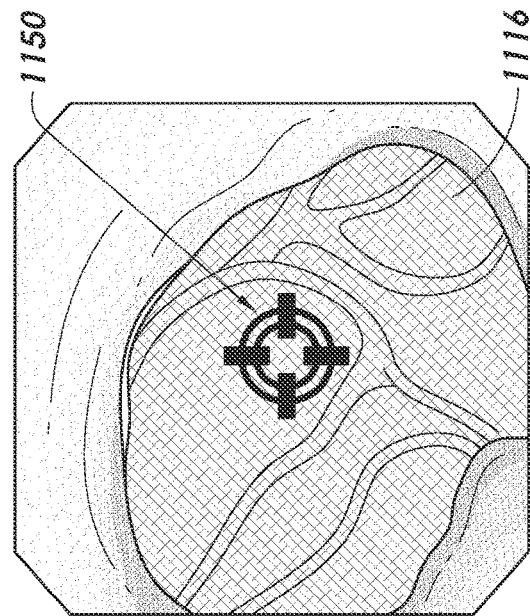
Figure 11:
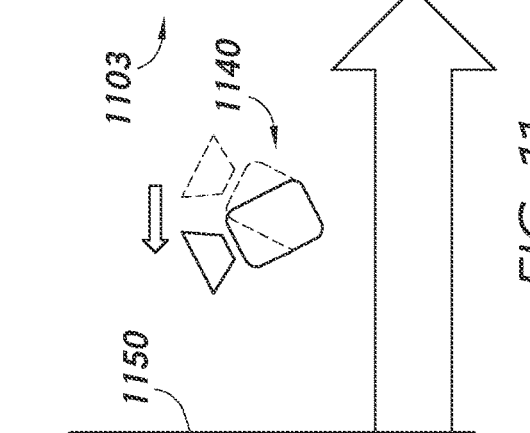

FIG. 11 shows an example image 1101 from a camera associated with the distal end of an endoscope, such as a ureteroscope, in accordance with one or more embodiments of the present disclosure. The image 1101 may be presented on a scope-guidance interface, such as is shown in FIG. 9 and described above. The image 1101 may represent a window, or portion of a window (e.g., sub-window) configured to display a camera view including at least a portion of a field of view of a camera associated with the endoscope.

In some embodiments, the camera view interface/window 1101 may have overlain thereon one or more icons or features 1150 indicating a target positioning of a target anatomical feature(s) within the camera view 1101. The target icon(s)/feature(s) 1150 may serve to guide the operator with respect to proper alignment of the distal end of the endoscope with the target anatomical feature (e.g. papilla). In some embodiments, the target anatomical feature alignment guidance icon(s)/feature(s) 1150 may be generated and/or displayed such that the icon(s)/feature(s) 1150 remain in substantially the same position in the window 1101 even as the camera image displayed therein moves or changes as the scope moves. That is, the operator of the scope may manipulate/actuate the distal end of the scope to thereby alter the field of view of the camera and/or the representative anatomy captured therein. As the field of view 1101 of the camera changes, the icon(s)/feature(s) 1150 can remain in an overlaid representation at or near the center of the window/image 1101, as shown in FIG. 11. Therefore, the operator may be able to move the field of view of the camera, such as by changing the position of the scope, in order to selectively position the icon(s)/feature(s) 1150 over the target anatomical feature of interest, such as a papilla or other anatomical feature.

The alignment icon(s)/feature(s) 1150 may direct the operator to position the field of view of the camera such that the icon(s)/feature(s) 1150 is/are positioned and/or centered over the anatomical feature of interest 1116 (e.g., papilla). For example, as shown in image 1103, which represents a changed field of view of the camera associated with the scope after movement of the scope by the operator, the icon(s)/feature(s) 1150 may be used to guide the operator to center the icon(s)/feature(s) 1150 over the target papilla 1116, whereas in the initial field-of-view 1101, the target papilla 1116 is not generally centered within the field of view of the camera or with respect to the targeting icon(s)/feature(s) 1150. In order to change the field-of-view to center the icon(s)/feature(s) 1150 as shown in image 1103, the distal end of the endoscope and/or camera associated therewith, as represented by the icon 1140, may be panned, for example, to the left to bring the target papilla/feature 1116 into the field-of-view of the camera to a greater degree, as shown in image 1103 as compared to the image 1101.

The icon(s)/feature(s) 1150 can have any suitable or desirable shape, form, configuration, and/or number of visual features. For example, some embodiments, such as the embodiments shown in FIG. 11, include crosshairs-type features, which indicate a center point defined by the extrapolated intersection of lines or other features oriented in two or more axes. The illustrated icon(s)/feature(s) 1150 can additionally or alternatively include one or more circle forms, as shown, wherein a central axis thereof represents a center point of the icon(s)/feature(s) 1150. Generally, the icon(s)/feature(s) 1150 indicate that the operator should bring the center point of the icon(s)/feature(s) 1152 into general alignment with a center (e.g., volumetric and/or geometric center) of the target anatomical feature 1116.

The icon(s)/feature(s) 1150 shown in FIG. 11 can facilitate proper alignment of an endoscope with respect to a target anatomical feature. In addition (or as an alternative) to alignment guidance, embodiments of the present disclosure relate to endoscope parking guidance feature(s) that facilitate proper positioning of an endoscope with respect to a distance/depth thereof from a target anatomical feature (e.g., the papilla 1116). In some embodiments, certain icon(s)/feature(s) are generated and/or displayed over a camera view, wherein the icon(s)/feature(s) is/are configured such that a relative size thereof compared to the size of a representation of the target anatomical feature in the camera view indicates whether the scope is positioned at the proper distance/depth and/or how the scope should be moved in order to arrive at the proper distance/depth from the target anatomical feature. Furthermore, in some embodiments, the depth-positioning icon(s)/feature(s) can further include icon(s)/feature(s) that indicate alignment guidance as well.

Figure 12A:
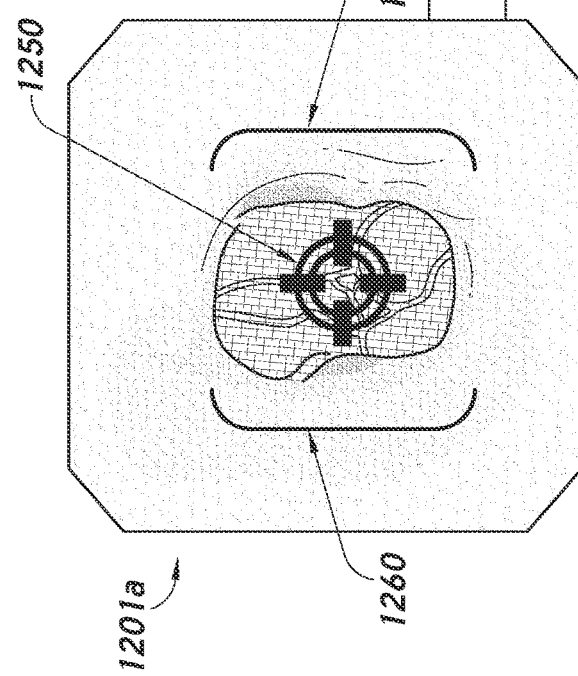
FIGS. 12A and 12B illustrate configurations of a scope camera view/window including a target-bounding feature in accordance with one or more embodiments.
Figure 12A:
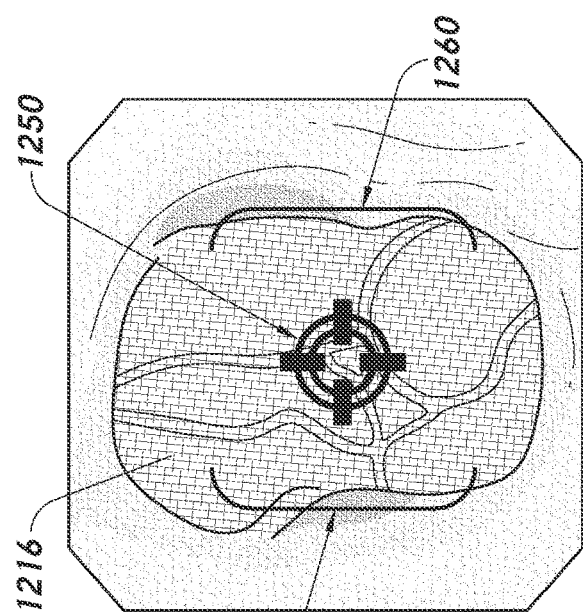
Figure 12A:
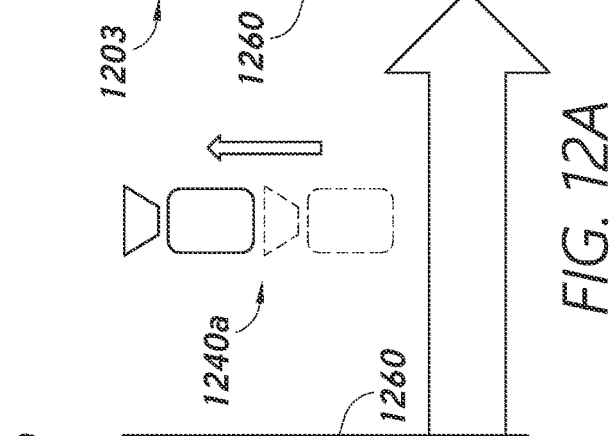
Figure 12B:
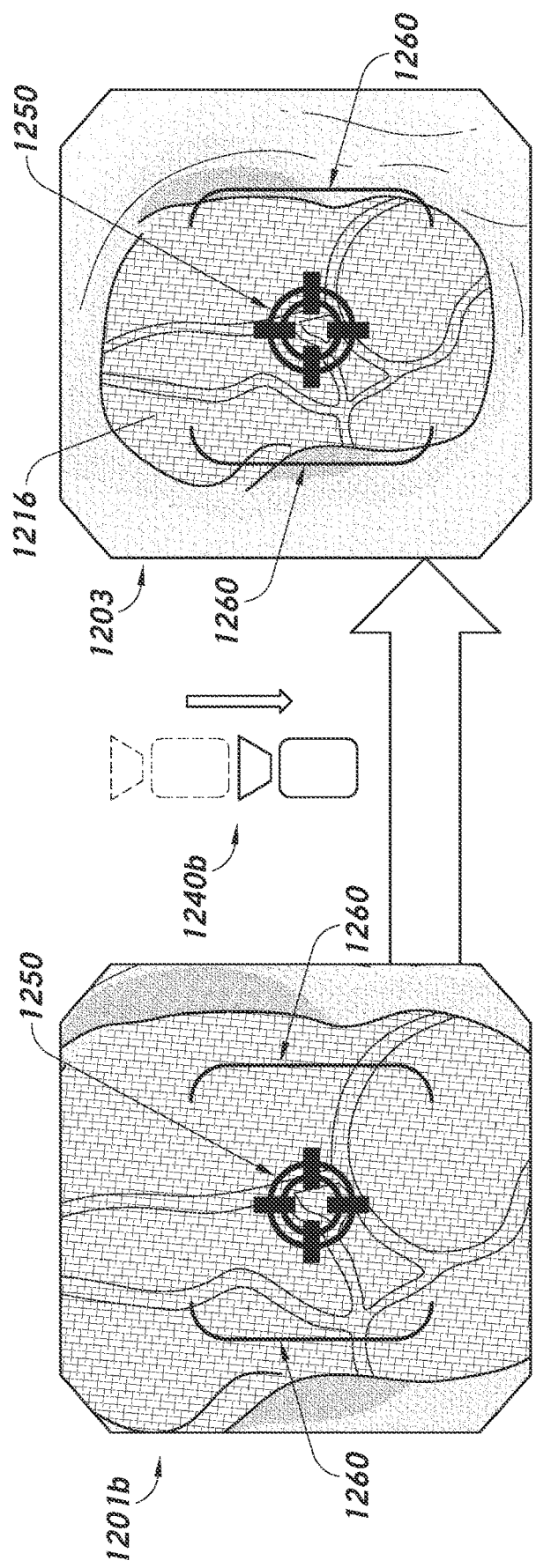

FIGS. 12A and 12B illustrate configurations of a scope camera view/window including a target-bounding feature 1260 in accordance with one or more embodiments, wherein the target-bounding feature 1260 guides the operator with respect to proper depth/offset positioning of the scope. FIGS. 12A and 12B show example images 1201a, 1201b from a camera associated with the distal end of an endoscope, such as a ureteroscope in accordance with one or more embodiments of the present disclosure. The images 1201a, 1201b may be presented on a scope-guidance interface, such as shown in FIG. 9 and described above. The images 1201a, 1201b may represent a window, or portion of a window (e.g., sub-window) configured to display a camera view including at least a portion of the field-of-view of a camera associated with the endoscope.

In some embodiments, the camera view interface/window 1201a, 1201b may have overlaid thereon one or more icons or features 1260 indicative of a target depth of the target anatomical feature 1216 within the camera view 1201a, 1201b. Offset icon(s)/feature(s) 1260 can include, for example, one or more brackets, bounding boxes, and/or other shapes or features representative of a containment of image content displayed between or within such icon(s)/feature(s). Bounding boxes or other similar-type features can be displayed at or around the center of the field-of-view of the camera and/or window showing the camera view, wherein such features can indicate or direct that the operator maintain all or at least a portion of the target anatomical feature (e.g., at least a center portion) within the bounding box form/feature to prevent the endoscope from being parked at a position too close to the target anatomical feature 1216. For example, in some embodiments, the bounding box feature(s) 1260 may direct the operator and/or indicate that the operator should maintain and/or fit at least a majority of the area of the anatomical feature 1216 represented on the camera image within the boundar(ies) defined and/or indicated by the offset-guidance feature(s) 1260 with respect to one or more axes (e.g., horizontally and/or vertically). In addition to reducing the likelihood that the endoscope will be parked too close to the target anatomical feature(s) 1216, by directing the operator to substantially fill the bounded area of the offset feature(s)/icon(s) 1260 with the target anatomical feature, or directing the operator to maintain the camera in a position such that a majority of the area bounded by the offset feature(s)/icon(s) 1260 is filled/covered with representative image of the target anatomical feature (e.g., papilla), the offset feature(s)/icon(s) 1260 can reduce the likelihood that the endoscope will be parked too far away from the target anatomical feature 1216.

With respect to the images 1201a, 1201b, and 1203 shown in FIGS. 12A and 12B, the images 1201a, 1201b show the offset feature(s)/icon(s) 1260 configured and/or positions about a center of the window 1201a, 1201b. As shown, in the image 1201a, the target anatomical feature (e.g., papilla) 1216 does not sufficiently fill the bounds of the offset future(s) 1260. Subsequent image 1203 can result from manipulation of the endoscope, as represented by the image

1240*a*, to bring the endoscope and/or associated camera closer to the target anatomical feature 1216, such that the resulting image 1203 shows the target anatomical features 1216 substantially filling the bounds of the offset feature(s)/icon(s) 1260.

With respect to FIG. 12B, the image 1201*b* shows the offset feature(s)/icon(s) 1260 with the representation of the target anatomical feature 1216 extending substantially outside of the bounds of the offset feature 1260 due to the endoscope camera being too close to the target anatomical feature 1216, thereby possibly resulting in obscuring of the visibility of the target anatomical feature 1216, such as when the target anatomical feature 1216 becomes deformed as a result of advancement of a percutaneous access instrument (e.g., needle) therein/therethrough.

Subsequent image 1203 can result from manipulation of the endoscope, as represented by the image 1240*b*, to withdraw the endoscope away from the target anatomical feature 1216, such that the target anatomical feature 1216, or a majority of the relevant portion thereof, is within the bounds of the offset feature(s)/icon(s) 1260 with respect to one or both dimensions/axes of the image 1204.

In certain embodiments, as shown in FIGS. 12A and 12B, bounded/bounding boxes 1260 can be displayed at or around the center of the view window (1201*a*, 1201*b*, 1203) to thereby direct/instruct the user to maintain the view representation of the target anatomical feature 1216 (e.g., papilla) wholly, or at least partially (e.g., more than half), within the bounds of the bounding box 1260, which may advantageously reduce occurrences and/or likelihood of the scope being parked either too far away, as in the image 1201*a* and/or relating to the scope position 1042 shown in FIGS. 10A and 10B, or too close, as in the image 1201*b* of FIG. 12B and/or relating to the scope position 1044 of FIGS. 10A and 10B.

The bounding box feature(s) 1260 can advantageously promote the standardization of how different users/physicians operate a scope with respect to target anatomical features of different sizes and across different patients, such that a suitable position is achieved for the scope with decreased dependence on the skill and/or experience of the physician and/or the particular anatomy of the patient. In some embodiments, the scope management system comprises devices configured to implement at least partially automatic positioning of the scope to position and/or maintain the target anatomical feature at least partially within the bounds of the bounding box feature(s). Therefore, anatomical motion resulting in a relative displacement of the target anatomical feature(s) with respect to the camera of the scope can be automatically compensated for using image processing functionality and/or other means or mechanism for automatically determining the relative position of the target anatomical feature with respect to the bounding box feature(s).

In some embodiments, the size and/or other features of the bounding box feature(s) 1260 may depend at least in part on certain anatomical specifications of the patient. For example, it may be desirable for a scope positioned in a relatively small calyx to be positioned relatively closer to the target papilla to reduce the risks of scope slippage/movement. For example, the guiding feature (e.g., bounding-box feature(s)) on superimposed/displayed on the endoscope view window may have fixed size (e.g., pixel size). This can enable the user to be guided to park closer for smaller calyces. That is, to fit a relatively smaller papilla in the bounding, offset-guidance icon(s), it may be necessary to park the scope relatively closer. If the calyx is small, the scope can have a tendency to fall out of the calyx, which is why closer parking may be desirable. Therefore, even in cases in which the size of the target calyx/papilla is unknown, by implemented a fixed-size targeting/bounding icon/feature and directing the user to park the scope such that the icon/feature is substantially (e.g., more than 50%, 60%, 75%, 80%, 90% or other percentage) filled with the target anatomical feature/region, an adaptive parking distance may be enabled for different calyces. It should be understood that such example is one of many possible examples in which the characteristics of the bounding box feature(s) is/are generated and/or presented dependent at least in part on particular determined characteristic(s) of the patient anatomy and/or parameter(s) manually entered by the technician. The various offset-guidance features described above with respect to FIGS. 12A and 12B may advantageously bound/limit the potential error of the percutaneous access targeting by controlling the range of distances and/or positions of the scope with respect to the target anatomical feature.

Figure 13:
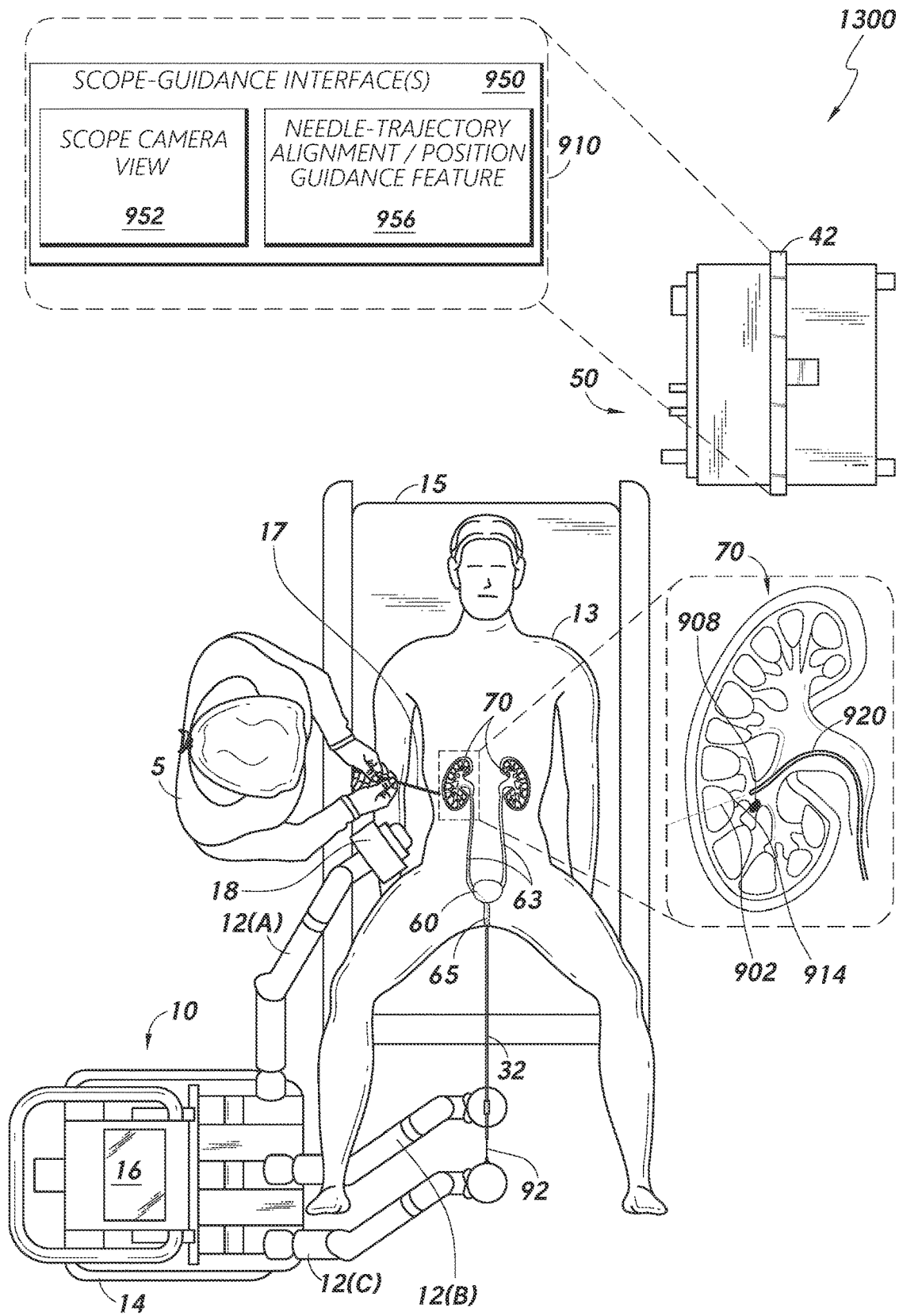
FIG. 13 illustrates a robotic medical system arranged to facilitate percutaneous accessing of renal anatomy of a patient in accordance with one or more embodiments.

FIG. 13 illustrates a robotic medical system arranged to facilitate percutaneous accessing of renal anatomy of a patient in accordance with one or more embodiments. As shown in FIG. 13, the physician 5 can implement percutaneous kidney access by positioning a needle 17 for insertion into the target location. In some embodiments, the physician 5 can use his/her best judgment to place the needle 17 on the patient 13 at an incision site based on knowledge regarding the anatomy of the patient 13, experience from previously performing the procedure, an analysis of CT/X-ray images or other pre-operative information of the patient 13, and so on. Further, in some embodiments, the control system 50 can provide information regarding a location to place the needle 17 on the patient 13. The physician 5 can attempt to avoid critical anatomy of the patient 13, such as the lungs, pleura, colon, paraspinal muscles, ribs, intercostal nerves, etc. In some examples, the control system 50 can use CT/X-ray/ultrasound image(s) to provide information regarding a location to place the needle 17 on the patient 13.

The control system 50 can include control circuitry configured to determine a target trajectory 902 for inserting the needle 17 to assist the physician 5 in reaching the target location (e.g., the papilla 914). The target trajectory 902 can represent a desired path for accessing the target location. The target trajectory 902 can be determined based on a position of one or more medical instruments (e.g., the needle 17, the scope 92, etc.), a target location within the patient anatomy, a position and/or orientation of the patient 13, the anatomy of the patient (e.g., the location of organs within the patient relative to the target location), and so on. In some implementations, the target trajectory 902 represents a straight line that passes through the papilla 914 and the point of the needle 17. The trajectory may be generally in-line with the axis of the infundibulum associated with the target calyx. However, the target trajectory 502 can take other forms, including a curved path, and/or can be defined in other manners. In some examples, the needle 17 is implemented an at least partially flexible and/or bevel-tipped needle. The control system 50 may be configured to provide information to guide the user/physician 5 in advancing the needle, such as to compensate for deviation in the needle trajectory or to maintain the user on the target trajectory.

Although the example of FIG. 13 illustrates the target trajectory 902 extending coaxially through the papilla 914, the target trajectory 902 can have another position, angle, and/or form. For example, a target trajectory can be implemented with a lower pole access point, such as through a papilla located below the kidney stone 908 shown in FIG.

13, with a non-coaxial angle through the papilla, which can be used to avoid the hip. In some implementations, a minimum-tract path/trajectory is taken in accessing the target calyx/papilla.

As described above, the control system 50 can present a screen 910 including one or more scope-guidance interfaces 950 via the display(s) 42 to view a real-time camera image/view 952 captured by the scope 92 to assist the physician 5 in controlling the scope 92. During percutaneous access, as shown in FIG. 13, the scope 92 may be parked in the target calyx and providing visibility of the target papilla 914. As the needle 17 is advanced in the direction of the target papilla 914, adjustment of the scope 92 may be guided at least in part by one or more needle trajectory alignment/position guidance feature(s) 956, which are described in detail below. Such feature(s) 956 can facilitate the positioning of the scope 92 in such a manner as to include an icon indicating the projected presentation of the needle 17 (e.g., needle tip position projected on the scope camera image window) in the target calyx within the field of view 952 of the scope camera. For example, where the projected needle entry point into the target calyx and/or through the target papilla 914 is outside of the field of view 952 of the scope camera, the interface feature(s) 956 can notify the physician 5 of the direction the scope 92 can be moved to bring the projected needle entry point into the camera view 952.

Once the target location has been reached with the needle 17, the physician 5 can insert another medical instrument, such as a catheter, vacuum, nephroscope, or the like, into the path created by the needle 17 and/or over the needle 17 and/or dilator (not shown) disposed in the access path. The physician 5 can use the other medical instrument and/or the scope 92 to fragment and remove pieces of a kidney stone from the kidney 70.

In some embodiments, a position of a medical instrument can be represented with a point/point-set and/or an orientation of the medical instrument can be represented as an angle/offset relative to an axis/plane. For example, a position of a medical instrument can be represented with coordinate(s) of a point/point-set within a coordinate system (e.g., one or more X, Y, Z coordinates) and/or an orientation of the medical instrument can be represented with an angle relative to an axis/plane for the coordinate system (e.g., angle with respect to the X-axis/plane, Y-axis/plane, and/or Z-axis/plane). Here, a change in orientation of the medical instrument can correspond to a change in an angle of the medical instrument relative to the axis/plane. Further, in some embodiments, an orientation of a medical instrument is represented with yaw, pitch, and/or roll information.

In some embodiments, a trajectory refers as a pose. For example, a trajectory of a medical instrument can refer to a pose of the medical instrument, including/indicating both a position and orientation of the medical instrument. Similarly, a target trajectory can refer to a target pose, including/indicating both a position and orientation of a desired path. However, in other embodiments, a trajectory refers to either an orientation or a position.

In some embodiments, the ureteroscope 92 and the needle or other percutaneous access instrument 17 have a common positioning coordinate system, such as in implementations in which the electromagnetic field generator 18 is utilized and each of the scope 92 and the needle 17 have respective electromagnetic sensor(s)/beacon(s) associated therewith that can be utilized determine the respective positions of the scope 92 and needle 17 in the common electromagnetic field space. For example, prior to a medical procedure involving the use of an endoscope and/or percutaneous access needle, the sensor(s)/beacon(s) associated with the distal end of the scope may be calibrated with the camera of the scope to determine a transform/relationship between the visual image space of the camera and the position in the electromagnetic field associated with images/features depicted and/or otherwise appearing in the image field of the camera. Such calibration may allow for position information to be determined and/or projected based on a position, size, and/or configuration/orientation of a feature/object representation within the image space (e.g., field of view) of the camera. Therefore, when a position of the percutaneous needle, as indicated by the electromagnetic sensor(s)/beacon(s) associated therewith, is determined and/or projected relative to the position of the camera and/or associated sensor(s)/beacon(s), such position may be determined/generated and/or displayed over the field-of-view image displayed on the scope camera view interface 952 based at least in part on the calibration of the camera, as described above. For example, as described in greater detail below, the camera calibration may be relied upon to overlay/present a needle-trajectory icon/feature on a camera view window, wherein such icon/feature indicates expected/projected position in the field of view at/through which the percutaneous needle is expected to project/appear as the needle is approximated to the target.

The scope-guidance interface(s) 950 may be configured to show certain needle-trajectory alignment/position guidance feature(s) 956, which may be presented in connection with (e.g., overlaid on or adjacent to) the scope camera view/window 952. For example, the needle-trajectory alignment/position guidance feature(s) 956 may comprise one or more icons or features displayed as part of the interface(s) 950 and indicating a position with respect to the camera view 952 at which the percutaneous access instrument (e.g. needle) is expected to enter the field-of-view of the camera and/or puncture the target anatomical feature/papilla. Such needle-trajectory alignment/position guidance feature(s) can facilitate maintenance by the scope operator of the projected entry point of the percutaneous access instrument within the field-of-view 952 of the camera. The feature(s) 956 indicating the projected position of the percutaneous access instrument may have any suitable or desirable shape, form, and/or representation, as with other interface icons/features disclosed herein.

FIGS. 14-1 and 14-2 illustrate configurations of a scope camera view/window including one or more needle-trajectory features in accordance with one or more embodiments. FIG. 14-1 shows an example image 1401 from a camera associated with the distal end of an endoscope, such as a ureteroscope in accordance with one or more embodiments of the present disclosure. The image 1401 may be presented on a needle-trajectory scope-guidance interface, such as shown in FIG. 13 and described above. The image 1401 may represent a window, or portion of a window (e.g., sub-window) configured to display a camera view including at least a portion of the field-of-view of a camera associated with an endoscope (e.g., ureteroscope).

The position of a target anatomical feature (e.g., papilla) 1416 may be tracked/localized and used as a target for percutaneous access to the chamber conduit, or other area (e.g., calyx) where the endoscope is disposed/parked. For example, in some implementations, the position of the target anatomical feature 1416 (e.g., papilla) may be determined based at least in part on one or more of the following: the recorded contact position of the papilla in accordance with implementations that involve contacting the papilla with the distal end of the endoscope and recording the position information associated with endoscope in connection with such contact; and the size, shape, and/or configuration/orientation of the target anatomical feature 1416 in the image/field-of-view of the camera, which may provide position information based on the calibration of the camera. With respect to embodiments relying on camera calibration information, the relative size, shape, and/or orientation/configuration of the target anatomical feature 1416 compared to the visual characteristics thereof at a subsequent point in time after which the scope has been retracted/withdrawn some amount from contact with the target anatomical feature may provide information indicating the present position of the target anatomical feature 1416. Calibration of the camera image and the electromagnetic field space may be achieved and/or performed in any suitable or desirable manner. For example, in some implementations, a checkerboard-type or other object/pattern of known shape, size, and/or configuration may be used to determine the position of object representations in the camera image.

In some implementations, the determination of the translation between three-dimensional electromagnetic space positioning and position/configuration in camera space can be leveraged to generate/display needle-trajectory icon(s)/feature(s) on a camera image window, such as the camera image window 1401, 1403 of FIG. 14. For example, the present position and/or projected position of the tip of the percutaneous needle (not shown) may be visualized/represented on the camera window 1401, 1403 to provide direction to the operator regarding where to position the scope camera to capture in the field-of-view thereof the needle when it punctures the anatomical feature 1416 and/or surrounding anatomy. Presentation of the needle-trajectory alignment/position guidance feature(s)/icon(s) 956 can facilitate confirmation of successful and/or unsuccessful access/puncturing of the percutaneous needle to access the target anatomical site.

The representation of the icon(s)/feature(s) (e.g., 1470, 1475, 1480) indicating the position of the needle can be helpful in situations in which the target anatomical feature/tissue becomes at least partially deformed as the percutaneous needle passes therein/therethrough, which may result in visual obstruction in some instances. That is, as the needle is advanced closer, the visibility of the target anatomical feature may become more uncertain, and therefore confirmation of successful and/or unsuccessful targeting by the percutaneous needle may be difficult to determine without needle-trajectory feature(s) in accordance with aspects of the present disclosure.

The image 1401 shows an example image and associated needle-trajectory/position feature(s) 1470, 1475 in a context where the projected and/or present needle position is outside of the camera field-of-view 1401. In such situations, the icon(s)/feature(s) 1470, 1475 may be generated and/or displayed to indicate a direction and/or positioned relative to the field of view 1401 where the projected or present position of the needle would be with respect to the present field-of-view of the image 1401. For example, an arrow or other icon 1470 may be displayed in an area outside of the window 1401 indicating a direction/position outside of the window 1401 associated with the needle trajectory. Alternatively or additionally, one or more icon(s)/feature(s) 1475 may be overlaid on the image 1401 to indicate the direction and/or position outside of the field-of-view of the image 1401 where the needle position would be projected if the field-of-view of the image 1401 were greater in size.

Image 1403 shows the camera view after certain articulation/movement of the distal end of the scope and/or associated camera. For example, in accordance with the indicated needle trajectory (e.g., 1470 or 1475) shown in image 1401, the camera represented by the icon 1440 may be panned in the direction of the indicated needle trajectory to bring the projected position of the needle into the field-of-view of the camera. The image 1403 may further reflect slight upward pitch of the scope/camera 1440 to bring the needle-trajectory icon/feature 1480 further into the field-of-view of the camera and/or generally in the direction of a center thereof. The icon/feature 1480 can represent or correspond to the position of the needle tip, or it can correspond to the projected needle entry point.

In some embodiments, the needle-trajectory icon 1480 may be configurable to change in size, color, shape, and/or with respect to one or more other features/characteristics thereof, to represent a distance, alignment, and/or other position-related characteristic of the tip of the needle. In some embodiments, the icon 1480 becomes larger (or smaller) as the needle tip comes closer to the scope/camera. In some embodiments, the icon 1480 may be larger when the needle is relatively farther away, to represent a range of error of position of the projected needle tip, whereas as the needle tip comes closer to the scope/camera, the certainty with respect to the particular position where the needle will appear when it has punctured the target anatomy may be greater, and thus the area of the icon 1480 may be smaller to reflect the area within which the needle may appear. Generally, some embodiments may include icons having certain visual characteristics representing three-dimensional alignment, orientation, shape, and/or position of the needle, as represented in the two-dimensional image space of the camera. For example, a cone icon or the other icon including an apex or other directional shape/feature may be generated and/or presented to indicate depth perception with respect to the projected or determined position of the needle. In some embodiments, certain shading features are incorporated with the needle-trajectory icon(s)/feature(s) (e.g., 1470, 1475, and/or 1480) to indicate additional positioning, alignment, and/or orientation information relating to the needle.

The needle alignment/position guidance feature(s) 956 can include the needle-trajectory icon(s) as represented in images 1401 and/or 1403 and may further include certain visual representations/interfaces providing direction for advancement of the percutaneous needle to direct the needle towards the tracked target anatomical feature(s). For example, one or more needle-perspective interface features may be provided to direct the alignment, orientation, and/or positioning of the needle to guide advancement thereof, whereas additional scope-perspective interface(s) and associated needle-trajectory icon(s)/feature(s) can be presented to provide additional confirmation and/or guidance indicating needle positioning relative to the scope's camera.

The size of the needle-projection icon 1480 can be changed/modified based on a determined needle projection/prediction accuracy. In cases where there is substantial anatomical motion, which may result in needle-projection error, the needle-projection icon can be presented with a relatively larger size to represent a relatively larger determined error with respect to the needle projection/trajectory.

FIG. 14-2 shows an image 1405 including a needle-trajectory projection feature 1483 visually projecting from the needle-projection icon 1480. The feature 1483 may have certain visual characteristics indicating a three-dimensional projection of the needle along the path that the needle 1475 is projected to travel. The image 1407 shows the needle 1475 puncturing through the anatomical feature 1416 and projection along the path indicated by the projection feature 1483. That is, whereas in the image 1405 the needle tip is inside/behind the anatomical feature 1416, the image 1407 shows the needle tip 1475 after it has pierced the anatomical feature 1416 and entered the treatment site. The image 1405 includes both a tip-location icon 1480 and the overlay 1483 on the needle shaft to indicate the needle pose. The image 1407 shows both the orientation indicator of where the tip is, as well as the overlay on the needle shaft to indicate a three-dimensional perception of the needle pose.

Calyx/Infundibulum Axis Estimation for Papilla Localization

Calyx and/or infundibulum axis estimation may be implemented in connection with any of the embodiments disclosed herein in order to provide papilla offset trajectory information for papilla localization/tracking. Axes of calyces and/or associated infundibula can be estimated/determined in various ways. For example, calyx mapping may be implemented as a step in determining an axis of a calyx/infundibulum, as described in detail below.

Kidney mapping can be used to localize the target papilla for the purpose of percutaneous access needle targeting and/or target localization in accordance with embodiments of the present disclosure. In some implementations, a kidney map, as may be generated using any of the methods disclosed herein, may be used to estimate/determine surface normals associated with the target calyx, which may in turn be used to determine the calyx/infundibulum axis. In some implementations, the percutaneous access path to the target anatomical site may be determined and/or aligned with the orientation of the target papilla/calyx, which may be generally in-line with the central axis of the associated infundibulum in some cases. In some implementations, the trajectory of the distal end portion of the endoscope leading up to a target calyx/papilla can be used to determine and/or estimate the axis of the infundibulum associated with the target calyx. For example, the path of the scope may be linearized in some manner to generate an axis path/estimation. Even in cases where the endoscope is not aligned with the target papilla/calyx, aspects of the present disclosure provide mechanisms for determining the orientation of the target calyx/papilla, which may be used as the target trajectory for percutaneous access and/or for target localization.

Figure 15:
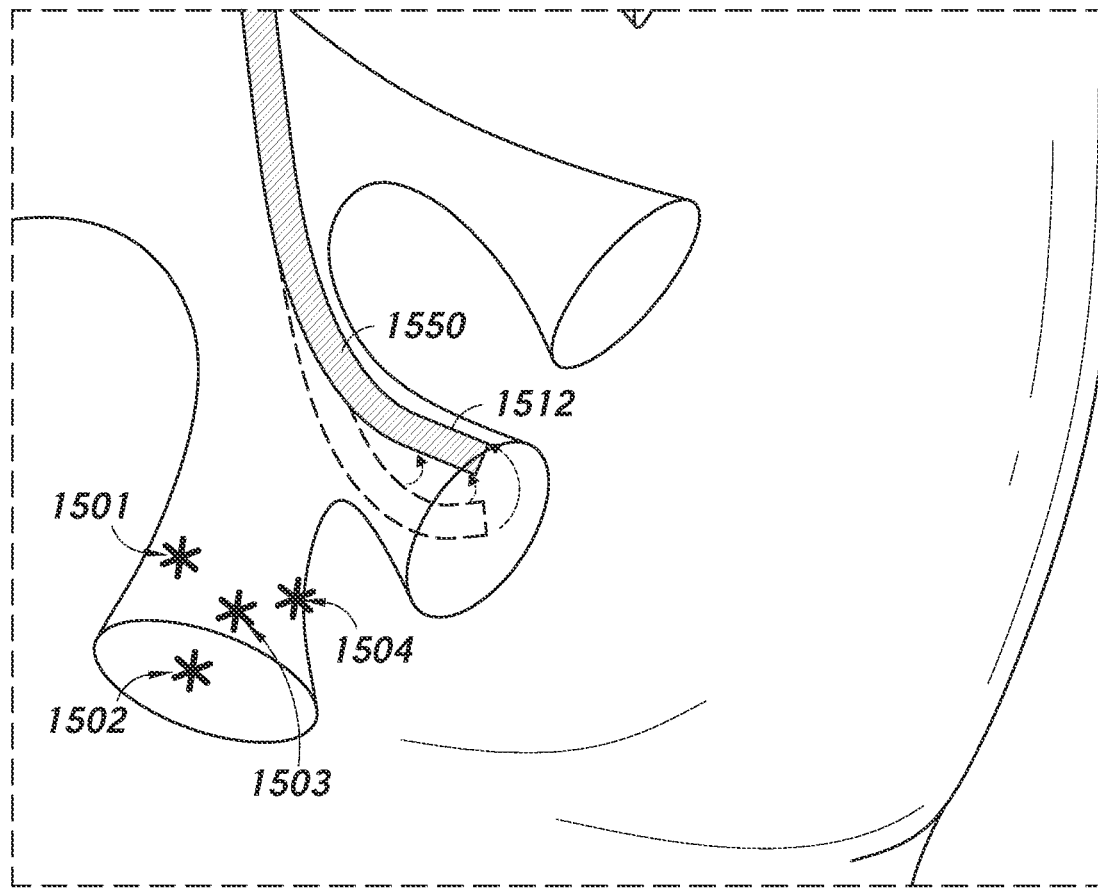
FIG. 15 shows a scope device disposed within target renal anatomy for calyx mapping in accordance with one or more embodiments.

FIG. 15 shows a scope device 1550 disposed within target renal anatomy for calyx mapping in accordance with one or more embodiments. With reference to FIG. 15, mapping of the calyces of the kidney can involve advancing and/or maneuvering a ureteroscope 1550 within the calyx network. For example, the ureteroscope 1550 may be advanced to the termination points (e.g., at the respective papillae) of one or more calyces and/or against the walls or other boundaries of the calyces, wherein periodic or sporadic position tagging/recording 1501-1504 may be implemented to generate a skeletal mapping of the traversed area of the calyces. For example, the operator of the ureteroscope 1540 may be directed to articulate the scope to tag multiple points 1501-1504 inside the target calyx. Such points 1501-1504 may be used to construct the shape of the calyx, wherein the center of the constructed calyx can be used as a percutaneous access target and/or can be followed when translating the present scope position by an offset distance/position to localize the papilla. In some implementations, the scope 1550 may be articulated in sweeping motions, as shown, to outline/cover the traversed area.

In some implementations, mapping of the calyces may be used to determine the infundibulum axis and/or orientation. For example, substantially all of the calyx network of the kidney, or a subset of the calyx network, may be mapped. In some implementations, only the target calyx and/or associated infundibulum may be mapped to determine the orientation/axis of the calyx and/or infundibulum. Papilla targeting trajectory and/or papilla offset localization may be determined based at least in part on the determined calyx/infundibulum axes and/or other local topology associated with the target calyx/papilla. For example, as discussed in detail above with respect to FIG. 8, target papilla localization may be achieved at least in part by implementing a papilla-scope offset translation (e.g., $P_{offset}$) and applying the translation/offset to the present position of the endoscope (e.g., within an electromagnetic field space). The determination of scope-to-papilla offset/translation may be based at least in part on the axis of the calyx and/or associated infundibulum. That is, determination of the trajectory in which the target calyx is pointing may be used to determine the target papilla offset from the distal end of the scope. For example, the determined offset of the scope may be added to the present position of the scope in the direction of calyx or infundibulum orientation/axis to determine the target position. In some cases, the target calyx may be oriented in generally the same direction/orientation as the associated infundibulum. However, with respect to fused calyces, which may generally be more common in the lower pole of the kidney and/or calyx network, the orientation of the calyx may be relied upon without regard to infundibular axis.

Figure 16:
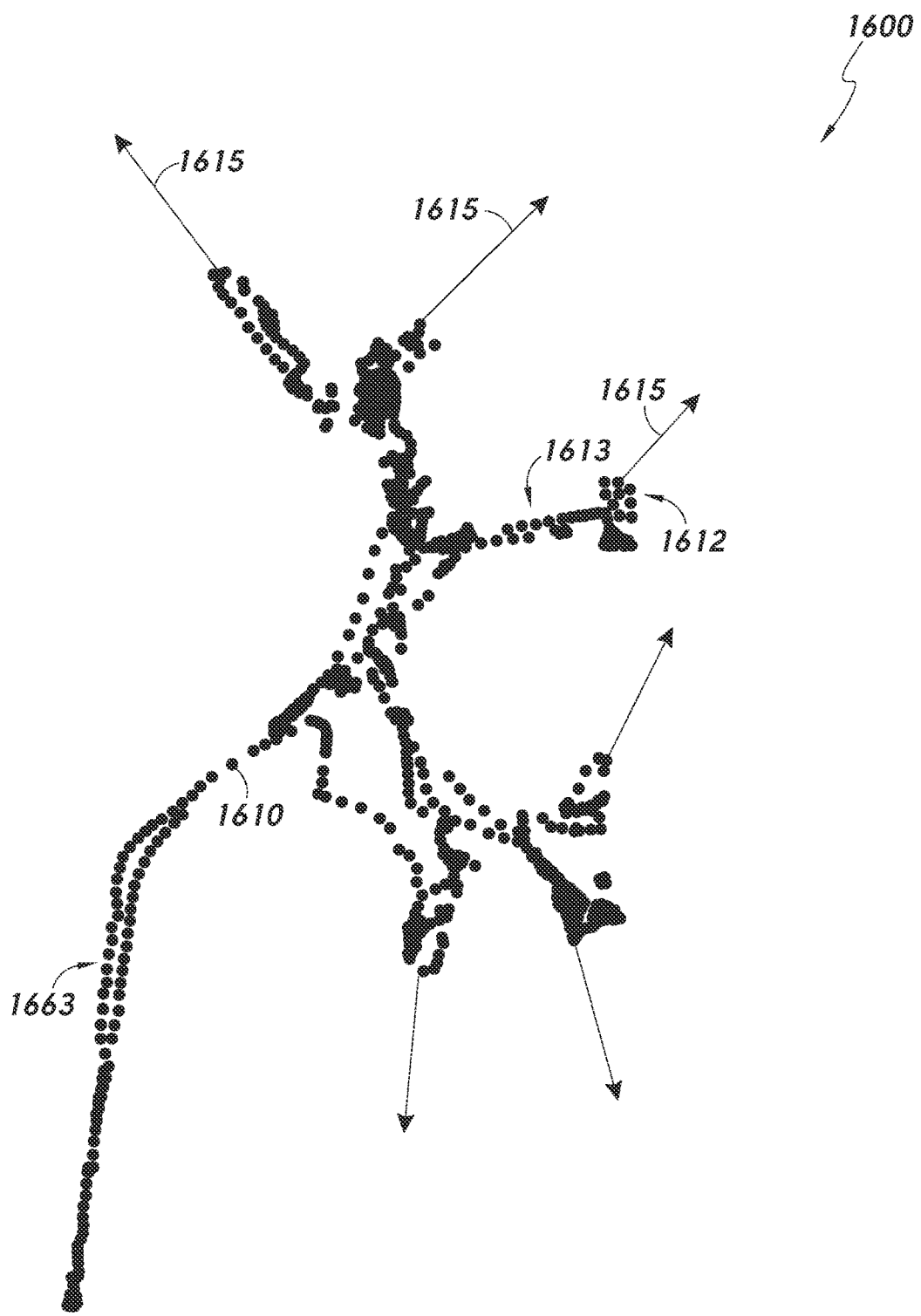
FIG. 16 shows images relating to an image-based target localization system in accordance with one or more embodiments.

While driving the scope to the target papilla/calyx, a plurality of positions associated with the distal end portion of the scope may be tagged/recorded along the path to provide a scatterplot-type mapping of at least a portion of the calyx network (e.g., the target calyx and/or associated infundibulum). For example, FIG. 16 shows a map 1600 of a calyx network including a plurality of calyces, both major and minor, leading from the ureter 1663. The various calyx axes 1615 illustrated in FIG. 16 may be determined based on the recorded scope positions along the travel path of the scope (not shown). Specifically, the individual illustrated circles (e.g., 1610) may represent tagged/recorded positions of the scope. In some implementations, a Gaussian interpolation may be implemented along the reported trajectory, or portion thereof, within a target calyx 1612 and/or associated infundibulum 1613, wherein such interpolation is used to generate a surface estimate with respect to at least a portion of the calyx network.

Figure 17:
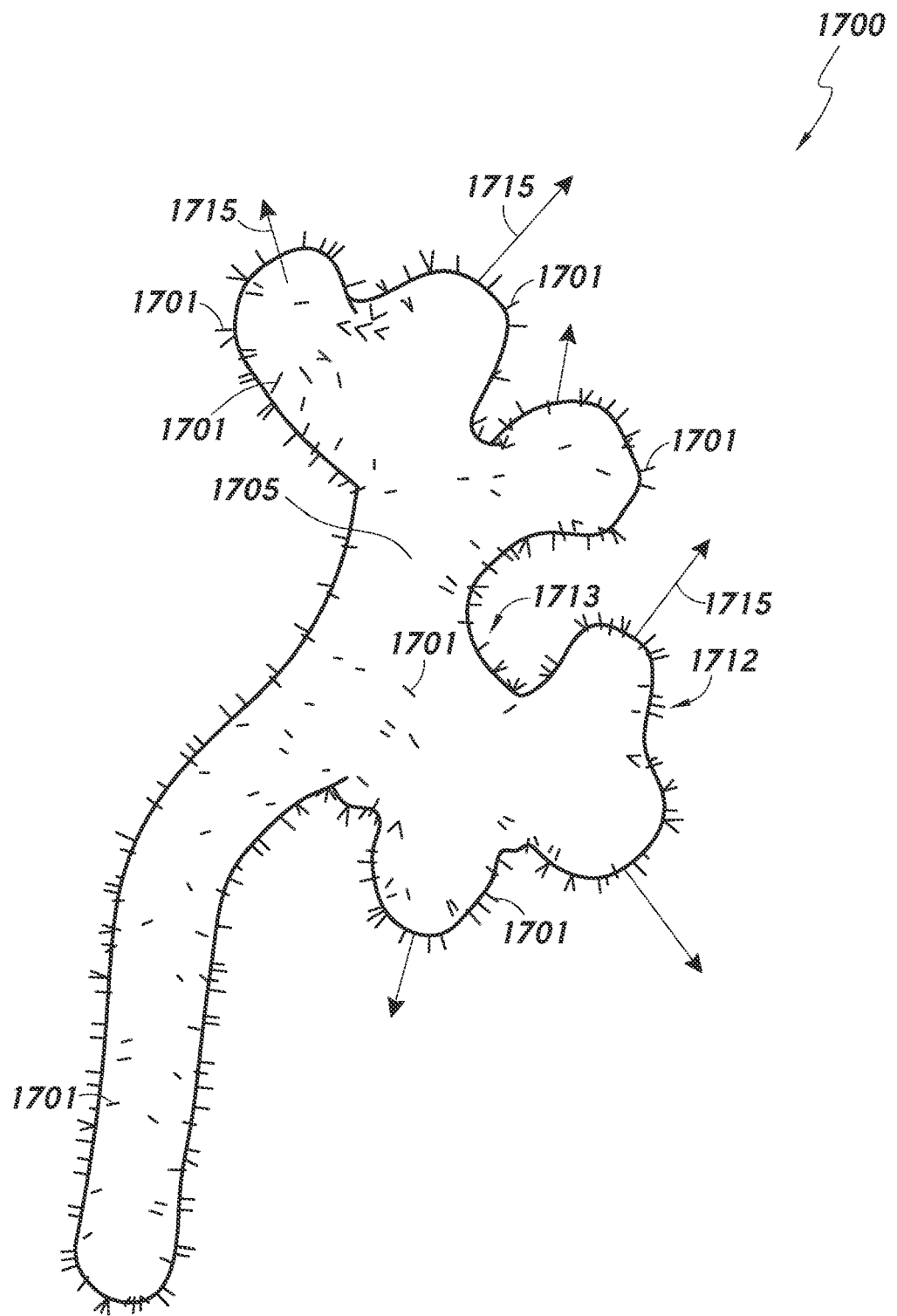
FIG. 17 shows a calyx map formed of recorded scope positions in accordance with one or more embodiments.

In some implementations, surface and/or volume estimation algorithms/mechanisms may be implemented to determine a center/axis of the target calyx and/or associated infundibulum. FIG. 17 shows a generated three-dimensional surface map 1700 generated in any suitable manner, such as using a Gaussian interpolation. For example, with the calyx and/or infundibulum surface determine/generated, the calyx/infundibulum axis 1715 can be determined based at least in part on the estimated surface(s). In some embodiments, a plurality of surface normals 1701 may be determined for the various areas of the surface 1705, wherein the surface normals 1701 are vectors/trajectories that are substantially orthogonal with respect to the surface 1705 at the origination point associated with the respective surface normal 1701. The internal axis of an infundibulum/calyx may be determined based at least in part on an averaging of surface normals extending around and/or on opposite sides of the form/structure 1700. For example, the surface normal vectors may be summed to determine the central axis for each respective portion of the calyx network 1700. Such axes can be extrapolated to provide calyx trajectories 1715. In some embodiments, determination of the calyx trajectories can be based at least in part on the summing of surface normal vectors and/or the determination of calyx/infundibulum axes.

In some embodiments, as shown in FIG. 15, circular motions may be effected in the scope to generate a sufficient position plot of the target calyx, wherein the calyx map to be formed therefrom. The calyx orientation 1715 can be estimated from the calyx map 1700, wherein such trajectories 1715 can provide a path along which scope/papilla offset may be projected/determined. This may allow the target position to be updated more robustly for cases where the scope heading changes with respect to the calyx, infundibulum, and/or papilla axis due to tissue deformation during needle insertion. Depending on the particular procedure, it may not be necessary to map out the entire calyx network of the kidney for the purpose of percutaneous access targeting. For example, only the calyx associated with the target papilla may be mapped in some implementations. In some implementations, multiple calyces may be mapped to provide increased spatial information/mapping.

Compared to solutions implementing fluoroscopy to find the position of the target calyx for targeting purposes, embodiments of the present disclosure can eliminate the need to obtain one or more fluoroscopy images of the collecting system at different angles to determine the location and orientation of the target papilla/calyx. Furthermore, embodiments of the present disclosure may advantageously provide for target anatomical feature targeting without the need for retrograde installation of contrast material or air to visualize the target anatomical feature. Therefore, embodiments of the present disclosure may be implemented without the need for prior cystoscopy and/or ureteric catheterization. Compared to solutions implementing ultrasound for the purpose of determining the decision of the target calyx for targeting purposes, ultrasounds may show only a 2-dimensional image of the collecting system and/or provide a relatively limited visualization of the ureter a scope and/or percutaneous access needle.

Vision-Based Target Localization

In some implementations, vision-based processes can be implemented to determine the direction/axis of the infundibulum/calyx, such as may be implemented while the scope is being driven to the target calyx/papilla. For example, multiple camera images and EM-based position data relating to the endoscope can be obtained at distinct positions/orientations with respect to the target papilla, wherein the three-dimensional (3D) location of the papilla with respect to the scope may be determined based on such data.

Figure 18:
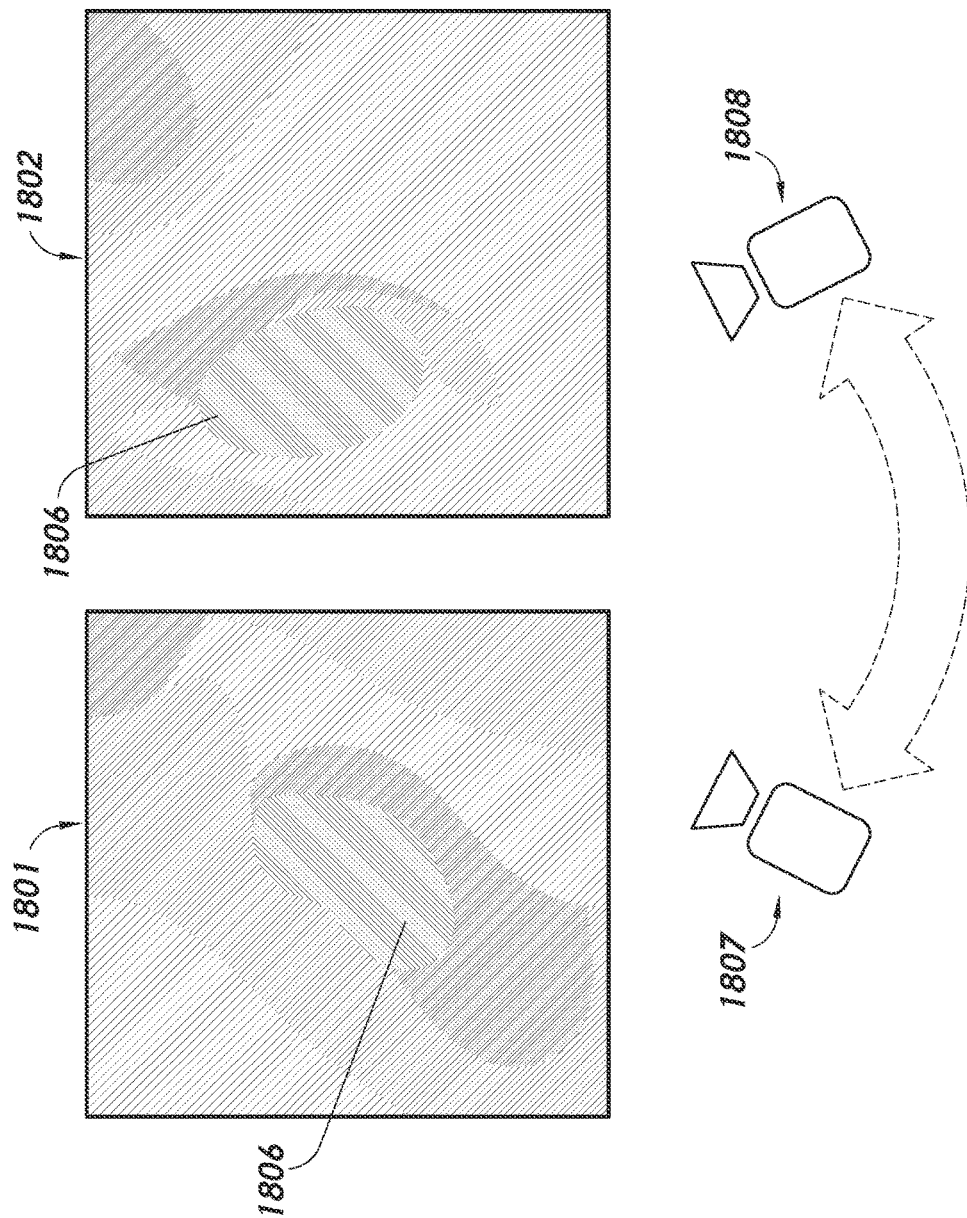
FIG. 18 shows a calyx surface map including surface-normal and calyx-trajectory indicators in accordance with one or more embodiments.

Localization of the target anatomical feature (e.g., target papilla) may be achieved using any suitable image processing mechanisms/functionality. For example, control circuitry of the medical system may receive image data from the scope camera and run certain image processing processes/functionality thereon to identify the target anatomical feature(s). In some implementations, at least two separate images of the target anatomical feature(s) are processed in order to track the position thereof. For example, as shown in FIG. 18, an image 1801 including a target anatomical feature(s) 1806 may be captured from a first perspective/position 1807 of the scope camera, wherein a second image 1802 may be captured by the scope camera either before or after capture of the first image 1801, wherein the second image 1802 is captured from a different perspective/position 1808 of the scope camera. In some implementations, structure-from-motion techniques can be implemented to determine the three-dimensional position of the target anatomical feature(s) 1806 based at least in part on the images 1801, 1802. The images 1801, 1802 may represent masked and/or otherwise parsed/processed feature-delineation images, wherein the target anatomical feature 1806 is demarcated, as shown in FIG. 18. Any computer vision algorithm or process may be implemented in connection with localization and targeting processes disclosed herein. For example, such image-processing processes may be relatively well-crafted contour-detection processes, black-box machine learning processes, and/or the like.

Three-dimensional (3D) position estimation for the purpose of target anatomical feature localization in accordance with aspects of the present disclosure may be implemented according to any suitable or desirable technique or mechanism. For example, in some embodiments, distance between an endoscope camera and a target anatomical feature may be estimated based on the representative size of the anatomical feature 1806 in an image.

In some embodiments, information relating to angle of movement of a scope and/or anatomical feature may be used to determine 3D position. For example, electromagnetic sensors/beacons in an electromagnetic field/space can provide such angle of movement information. By combining electromagnetic sensor data with image data, mappings between the distance from the target anatomical feature and size of the target anatomical feature in a resulting image captured after the movement of such distance can be used to estimate depth/distance of features in subsequent images. In some embodiments, when contacting the target anatomical feature (e.g., a papilla) and retracting the scope away from such feature to park the scope in a position to provide a desirable field-of-view, the distance traveled may be registered using, for example, electromagnetic sensor data. Furthermore, subsequent images can provide information relating to how large the anatomical feature appears in such images, and therefore the relationship/mapping between feature size and distance can be determined and used for future position determination; camera calibration, as described herein, may be implemented for such purposes. In some implementations, machine learning may be utilized to classify images and determine position information based on the size of features in such images.

In some embodiments, certain sensor(s) associated with medical instruments (e.g., scopes) can be utilized to obtain the 3D location of the target. For example, structured-lighting sensor(s) and/or time-of-flight sensor(s) can be used in determination of 3D positioning. According to some embodiments, a geometric translation approach may be implemented to detect the 3D position of a target anatomical feature. For example, as with certain other embodiments of the present disclosure, images 1801, 1802 may be captured that are associated with separate timestamps. In connection with such images, rotational translation information with respect to the camera (1807, 1808), which may be determined based on sensor information from any suitable or desirable sensor or device, may be used to triangulate and/or determine the positions of such images in 3D space, thereby providing information indicating 3D location of target anatomical feature(s) 1806 in the 3D space. The rotational translation information may be based on robotic actuator movement and/or position sensor information, such as from an electromagnetic beacon device associated with the camera and/or scope and indicating a position of the camera in the electromagnetic field space.

Given the intrinsic and extrinsic parameters (principle points, focal length and distortion factors, relative motion) of the camera (1807, 1808), the 3D location of the target anatomical feature 1806 can be calculated based at least in part on the tracked target two-dimensional (2D) locations on the images 1801, 1802. For intrinsic parameters, the camera principle point and focal length may be accounted for. Additional data that may be taken into account may include radial and tangential distortion factors. Based on the sensor readings (e.g., robotic- and/or EM-based), extrinsic parameters may also be obtained, including rotation R and translation T of the scope between the locations where the two images were taken. For convenience, K may be denoted as a matrix that contains the intrinsic parameters and H denoted as a 4-by-4 matrix that contains the extrinsic rotation and translation between the camera position of the first image ($C_t$) and the camera position of the second image ($C_{t+i}$).

For $C_t$, the 3D-to-2D projection relationship can be expressed as $x_t=KX$, where X is the 3D coordinate w.r.t. $C_t$ and $x_t$ is the 2D coordinate (detected centroid of a target) on image t. Here, K is a three-by-4 matrix that can be expressed as:

$$K = \begin{bmatrix} K_{(1)} \\ K_{(2)} \\ K_{(3)} \end{bmatrix},$$

with $K_{(n)}$ being the n-th row in K.

Similarly, for $C_{t+1}$, $x_{t+1}=K'X$, where:

$$K' = KH = \begin{bmatrix} K'_{(1)} \\ K'_{(2)} \\ K'_{(3)} \end{bmatrix}.$$

As $x_t$ and KX are parallel vectors, $x_t \times KX = 0$, and similarly, $x_{t+1} \times K'X = 0$. Here, 'x' is the cross-product operator. Hence:

$$x_t \times KX = 0 = > \det \begin{bmatrix} i & j & k \\ u_t & v_t & 1 \\ K_{(1)}X & K_{(2)}X & K_{(3)}X \end{bmatrix} = 0,$$

The above may produce: $i(v_t K_{(3)}X - K_{(2)}X) - j(u_t K_{(3)}X - K_{(1)}X) + k(u_t K_{(2)}X - v_t K_{(1)}X) = 0$, where $u_t$ and $v_t$ are the 2D coordinates of $x_t$. Hence:

$v_t K_{(3)}X - K_{(2)}X = 0$ $u_t K_{(3)}X - K_{(1)}X = 0$ $u_t K_{(2)}X - v_t K_{(1)}X = 0$

Here, only the first two equations may be needed, as the third equation is a linear combination of the first two. Similarly, for $C_{t+1}$, the following two equations can be obtained:

$v_{t+1} K'_{(3)}X - K'_{(2)}X = 0$ $u_{t+1} K'_{(3)}X - K'_{(1)}X = 0$

After stacking the equations of $C_t$ and $C_{t+1}$, the following may be produced:

$AX=0,$ where A is 4-by-4 matrix:

$$A = \begin{bmatrix} v_t K_{(3)} - K_{(2)} \\ u_t K_{(3)} - K_{(1)} \\ v_{t+1} K'_{(3)} - K'_{(2)} \\ u_{t+1} K'_{(3)} - K'_{(1)} \end{bmatrix}.$$

As the elements in A are known (detected 2D coordinates, intrinsic and extrinsic parameters), X can be calculated by performing singular value decomposition (SVD) on A:

$A = U\Sigma V^T,$ and the last column of V is the solution of X.

Therefore, in view of the foregoing disclosure, the various inventive concepts disclosed herein may be utilized to perform automatic target localization, including target detection, target tracking, and/or three-dimensional position estimation. In some embodiments, aspects of the present disclosure advantageously allow for target anatomical feature tracking without requiring physical contact with the target anatomical feature, which may facilitate improved ergonomics of the usage of the ureteroscope.

In some implementations, structured light and/or other non-contact optical sensing mechanisms may be utilized, such as optical coherence tomography, or other interferometry technology, may be used to determine depth/offset information. Such techniques may advantageously provide 3D papilla/calyx location information. However, structured-like devices may be relatively large and may increase the profile of the ureter scope configured there with. In some embodiments, the ureter scope comprises a time-of-flight camera configured to admit fight and receive reflections thereof, where in the time between the mission and reception of lights may be used to determine distance information within the kidney.

Distance/Angle Measuring Tools

Figure 19:
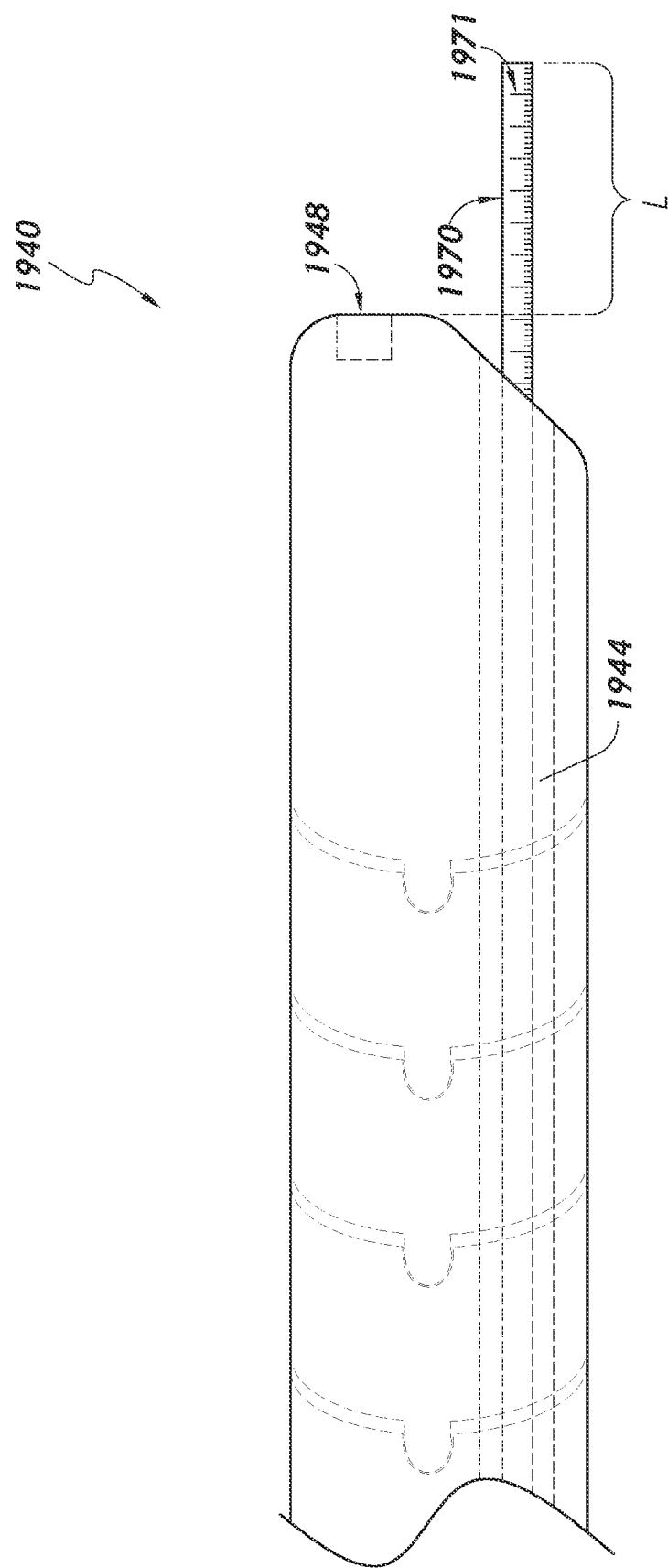
FIG. 19 shows a distal portion of an endoscope including a distance measurement tool in accordance with one or more embodiments.

FIG. 19 shows a distal end portion of an endoscope 1940, such as a ureteroscope, equipped with an offset distance measurement tool 1970 in accordance with one or more aspects of the present disclosure. For example, the offset distance measurement tool 1970 may be a ruler-type distance and/or angle measuring tool, which may be configured to be extended from a working channel 1944 of the scope 1940. Extension/projection of the measurement tool 1970 from the distal end of the scope 1940 can provide a mechanism for estimating the scope-to-papilla distance for the purposes of papilla localization when the measurement tool 1970 is projected far enough to contact and/or come in close proximity with the target papilla.

In some embodiments, the measurement tool 1970 comprises certain visual markings associated with a distal and/or proximal (not shown) portion of the measurement tool 1970. Such marking may indicate the amounts of distance/length L of the measurement tool 1970 that projects beyond the camera 1948 and/or distal end of the scope 1940. Although markings 1971, which may have any suitable or desirable form, are shown on the distal end portion of the tool 1970, in some embodiments, markings are not present on the distal end of the tool 1970, but rather are associated with a portion of the tool proximal to the illustrated portion of the scope 1940. For example, the markings may be associated with a portion of the tool 1970 that may be exposed proximally to the scope 1940, such that relative movement of the tool 1970 proximal to the scope 1940 can indicate the extent to which the tool 1970 is projected from the distal end of the scope 1940. In some embodiments, markings may be manually made on the proximal and/or distal portions of the measurement tool 1970 with respect to the position thereof prior to extension from the distal end of the scope 1940 and/or after contact of the tool 1970 with target anatomical feature.

In some implementations, electromagnetic sensors may be disposed on and/or otherwise attached or coupled to the target anatomical feature (e.g., papilla). For example, electromagnetic-visible wire may be guided through the scope 1940 (e.g., within the working channel 1944) and embedded at least partially in the target anatomical feature, such that the electromagnetic sensor/beacon feature(s) thereof can be maintained in contact or proximity with the target anatomical feature throughout the targeting/localization process, thereby providing an accurate real-time target for percutaneous access. In some embodiments, electromagnetic sensor/beacon device(s) may be coupled to the target anatomical features using an adhesive or other attachment means. In some embodiments, a conductive adhesive may be applied to the target anatomical feature, wherein the conductive adhesive itself serves as a visible electromagnetic material within the electromagnetic field space. In some embodiments, a balloon-type device may be implanted/embedded at least partially within the target anatomical feature (e.g., papilla), wherein the balloon may be configured to expand within the target anatomical feature to thereby secure itself thereto. Such balloon-type electromagnetic sensor(s)/beacon(s), or other expandable mechanical electromagnetic sensor/beacon devices, may advantageously provide a relatively large target for the percutaneous access instrument (e.g., needle) to target. Embodiments of electromagnetic sensor/beacon devices configured to be coupled to and/or embedded at least partially within the target anatomical feature can be permitted/inclined to move along with the movement and/or deformation of the target anatomical feature, thereby providing relatively robust localization/targeting solutions with respect to deformation and/or movement the target anatomical feature.

ADDITIONAL EMBODIMENTS

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A method of localizing a target anatomy, the method comprising:
   contacting a distal portion of an endoscope to an anatomical feature within an anatomy;
   determining a contact position of the distal portion of the endoscope in contact with the anatomical feature;
   determining a position of the anatomical feature based at least in part on the position of the distal portion of the endoscope;
   tracking the position of the anatomical feature over a period of time, wherein tracking the position of the anatomical feature includes:
   retracting the distal portion of the endoscope away from the contact position; and
   responsive to the retracting, determining a positional offset between the distal portion of the endoscope and the anatomical feature, wherein tracking the position of the anatomical feature is based at least in part on the contact position and the positional offset; and generating a real-time target for percutaneous access based on the tracked position.

2. The method of claim 1, further comprising:
   responsive to the retracting, determining a retracted position of the distal portion of the endoscope, wherein determining the positional offset is based at least in part on electromagnetic sensor data associated with the retracted position.

3. The method of claim 1, wherein determining the positional offset is based at least in part on one or more images captured using a camera of the endoscope responsive to the retracting.

4. The method of claim 1, wherein the positional offset indicates a pitch, a yaw, and a roll associated with the distal portion of the endoscope.

5. The method of claim 4, wherein the positional offset indicates at least five degrees of freedom associated with the distal portion of the endoscope.

6. The method of claim 1, wherein the endoscope is a ureteroscope advanced to an anatomical site through a urinary tract of the anatomy.

7. The method of claim 6, wherein the anatomical site is a calyx of a kidney within the anatomy, and wherein the anatomical feature is a papilla of the kidney that is at least partially exposed within the calyx.

8. The method of claim 1, further comprising:
   advancing a percutaneous access instrument along a path to the anatomical feature based at least in part on the real-time target.

9. The method of claim 8, further comprising:
   extracting an object from the anatomical feature through the path.

10. A system comprising:
    an endoscope configured to advance to an anatomical site within an anatomy; and
    a control system configured to:
    contact a distal portion of the endoscope to an anatomical feature within the anatomy;
    determine a contact position of the distal portion of the endoscope in contact with the anatomical feature;
    determine a position of the anatomical feature based at least in part on the position of the distal portion of the endoscope;
    track the position of the anatomical feature over a period of time, wherein tracking the position of the anatomical feature includes:
    retracting the distal portion of the endoscope away from the contact position; and
    responsive to the retracting, determining a positional offset between the distal portion of the endoscope and the anatomical feature, wherein tracking the position of the anatomical feature is based at least in part on the contact position and the positional offset; and generate a real-time target for percutaneous access based on the tracked position.

11. The system of claim 10, wherein the control system is further configured to:
    responsive to the retracting, determine a retracted position of the distal portion of the endoscope, wherein determining the positional offset is based at least in part on electromagnetic sensor data associated with the retracted position.

12. The system of claim 10, wherein determining the positional offset is based at least in part on one or more images captured using a camera of the endoscope responsive to the retracting.

13. The system of claim 10, wherein the positional offset indicates a pitch, a yaw, and a roll associated with the distal portion of the endoscope.

14. The system of claim 13, wherein the positional offset indicates at least five degrees of freedom associated with the distal portion of the endoscope.

15. The system of claim 10, wherein the endoscope is a ureteroscope advanced to an anatomical site through a urinary tract of the anatomy.

16. The system of claim 15, wherein the anatomical site is a calyx of a kidney within the anatomy, and wherein the anatomical feature is a papilla of the kidney that is at least partially exposed within the calyx.

17. The system of claim 10, wherein the control system is further configured to:
    advance a percutaneous access instrument along a path to the anatomical feature based at least in part on the real-time target.

18. The system of claim 17, wherein the control system is further configured to:
    extract an object from the anatomical feature through the path.

* * * * *